US007284900B2

(12) United States Patent
Mayer

(10) Patent No.: US 7,284,900 B2
(45) Date of Patent: *Oct. 23, 2007

(54) APPARATUS AND METHOD FOR MIXING SPECIMENS IN VIALS

(75) Inventor: William J. Mayer, South Barrington, IL (US)

(73) Assignee: Monogen, Inc., Vernon Hills, IL (US)

( * ) Notice: Subject to any disclaimer, the term of this patent is extended or adjusted under 35 U.S.C. 154(b) by 17 days.

This patent is subject to a terminal disclaimer.

(21) Appl. No.: 11/100,631

(22) Filed: Apr. 7, 2005

(65) Prior Publication Data

US 2005/0195684 A1 Sep. 8, 2005

Related U.S. Application Data

(63) Continuation of application No. 10/274,374, filed on Oct. 21, 2002, now Pat. No. 6,883,958.

(60) Provisional application No. 60/373,658, filed on Apr. 19, 2002, provisional application No. 60/372,080, filed on Apr. 15, 2002, provisional application No. 60/330,092, filed on Oct. 19, 2001.

(51) Int. Cl.
*B01L 3/00* (2006.01)
*B32B 5/02* (2006.01)
*B32B 27/04* (2006.01)

(52) U.S. Cl. ............... 366/197; 366/199; 366/279; 366/331; 422/99

(58) Field of Classification Search ........... 366/199, 366/197, 219, 220, 207, 203, 242, 244–248, 366/281–284, 331, 249–251; 422/63, 99
See application file for complete search history.

(56) References Cited

U.S. PATENT DOCUMENTS

| 4,070,854 A | * | 1/1978 | Marino ............ 53/381.4 |
| 4,577,973 A | | 3/1986 | Occelli |
| 4,781,468 A | | 11/1988 | Herfeld |
| 5,215,376 A | | 6/1993 | Schulte |
| 5,500,184 A | * | 3/1996 | Palmer ............ 422/2 |
| 5,846,489 A | | 12/1998 | Bienhaus et al. |

(Continued)

FOREIGN PATENT DOCUMENTS

JP 61-109693 11/1986

(Continued)

OTHER PUBLICATIONS

PCT search report, PCT/US02/33460, Feb. 4, 2003, 4 pages.*

*Primary Examiner*—Tony G. Soohoo
(74) *Attorney, Agent, or Firm*—Foley & Lardner LLP

(57) ABSTRACT

Method and apparatus for mixing a specimen (e.g., a biological fluid specimen) in an upstanding container having an internal mixer with a cavity defined by an upstanding annular wall. The annular wall of the mixer is engaged by a movable holder, which is elevated along with the engaged mixer sufficiently to prevent contact of the mixer with the container during mixing. The mixer is then moved to mix the specimen. The holder, which may include an expanding collet that fits within the cavity of the mixer, preferably rotates the mixer to stir the specimen. When mixing is complete, the holder is disengaged from the mixer. A controller coordinates all actions of the holder.

8 Claims, 51 Drawing Sheets

U.S. PATENT DOCUMENTS

| | | | |
|---|---|---|---|
| 5,865,538 A | 2/1999 | Walker et al. | |
| 6,149,871 A | 11/2000 | Guirguis et al. | |
| 6,296,764 B1 | 10/2001 | Guirguis et al. | |
| 6,883,958 B2* | 4/2005 | Mayer | 366/197 |
| 6,974,294 B2* | 12/2005 | Pressman et al. | 414/331.03 |
| 2003/0077838 A1* | 4/2003 | Pressman et al. | 436/177 |
| 2003/0087443 A1* | 5/2003 | Pressman et al. | 436/46 |
| 2003/0088963 A1* | 5/2003 | Mayer | 29/426.5 |
| 2003/0089731 A1* | 5/2003 | Mayer et al. | 221/279 |
| 2003/0092170 A1* | 5/2003 | Pressman et al. | 435/287.2 |
| 2003/0092186 A1* | 5/2003 | Pressman et al. | 436/46 |
| 2003/0097824 A1* | 5/2003 | Mayer et al. | 53/478 |
| 2003/0099580 A1* | 5/2003 | Pressman et al. | 422/104 |
| 2003/0100125 A1* | 5/2003 | Pressman et al. | 436/177 |
| 2003/0118487 A1* | 6/2003 | Pressman et al. | 422/104 |
| 2005/0195684 A1* | 9/2005 | Mayer | 366/197 |
| 2006/0120834 A1* | 6/2006 | Pressman et al. | 414/331.01 |
| 2006/0120835 A1* | 6/2006 | Pressman et al. | 414/331.01 |

FOREIGN PATENT DOCUMENTS

| | | |
|---|---|---|
| JP | 1-301087 | 5/1989 |
| JP | 4-166768 | 6/1992 |
| WO | WO99/10723 A1 | 3/1999 |
| WO | WO 01/67066 A2 | 3/2001 |

* cited by examiner

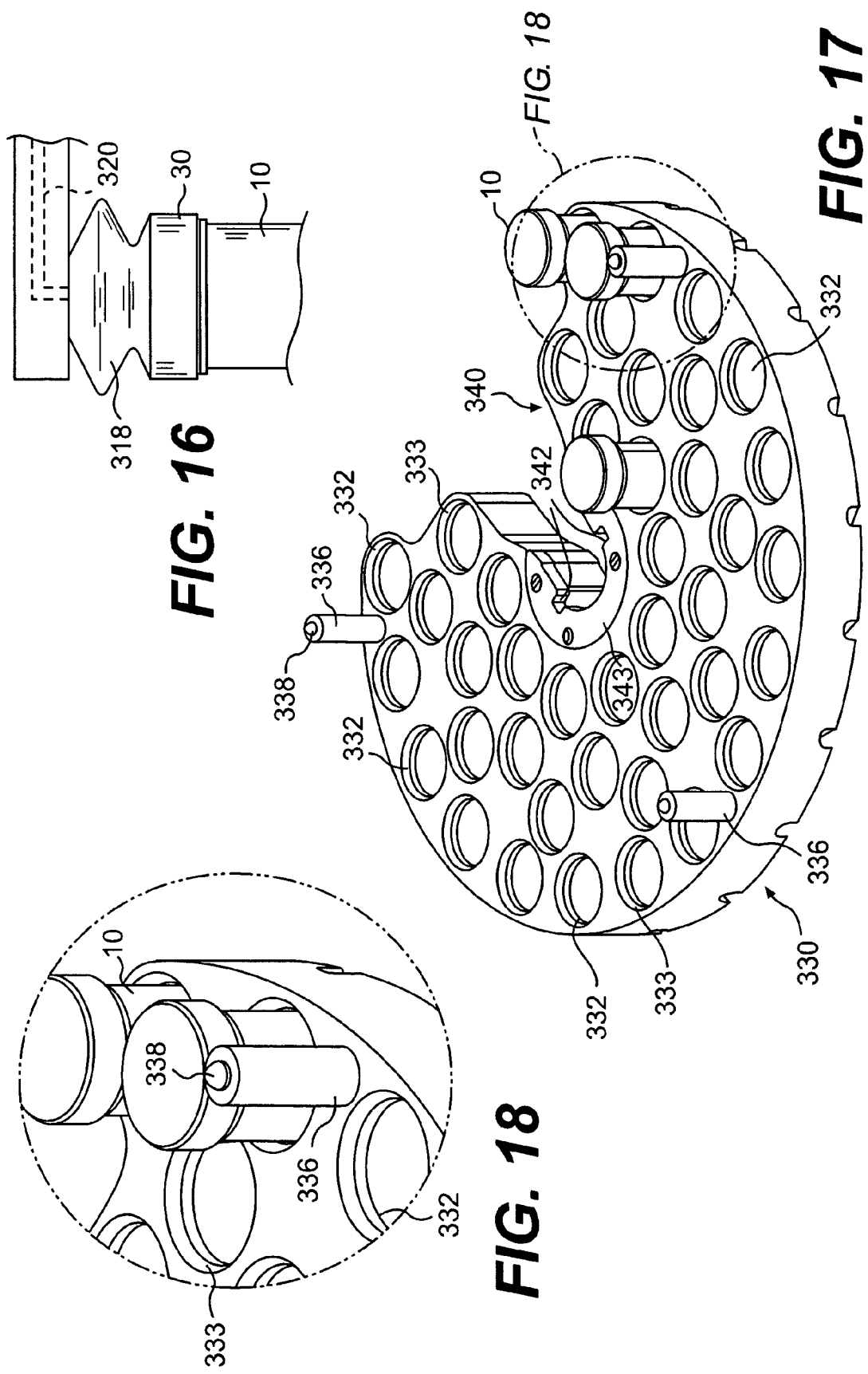

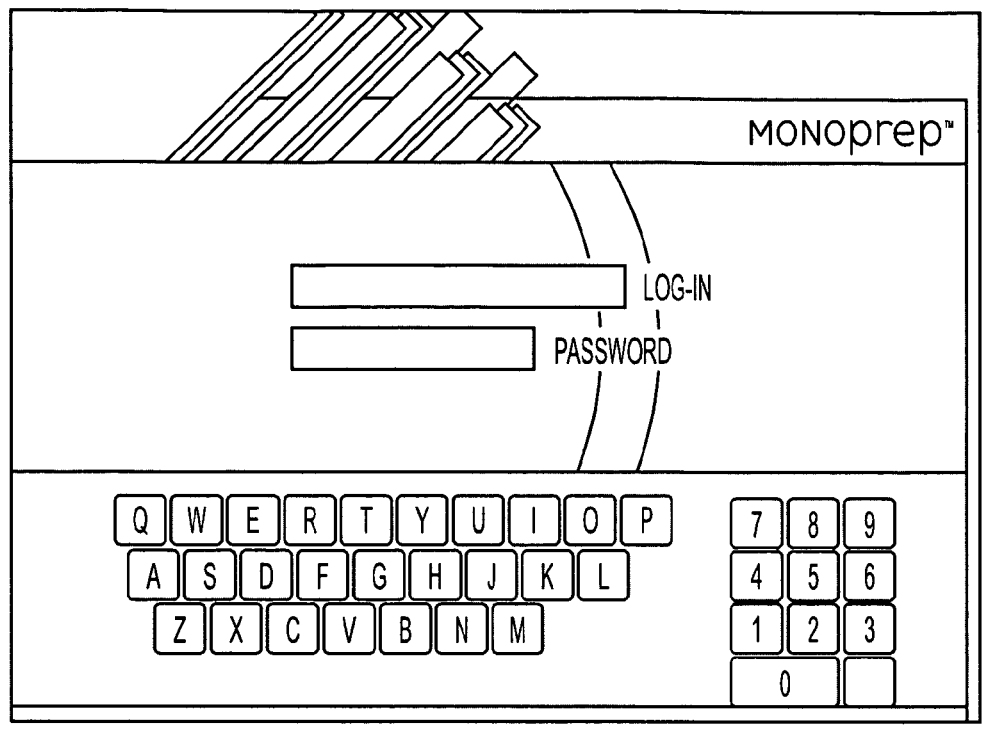
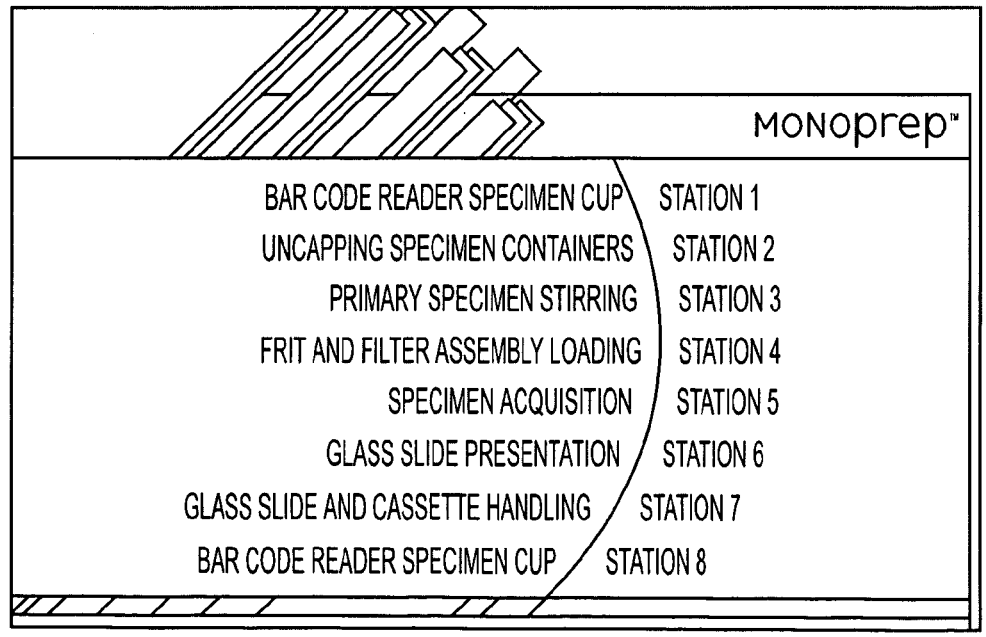
FIG. 25

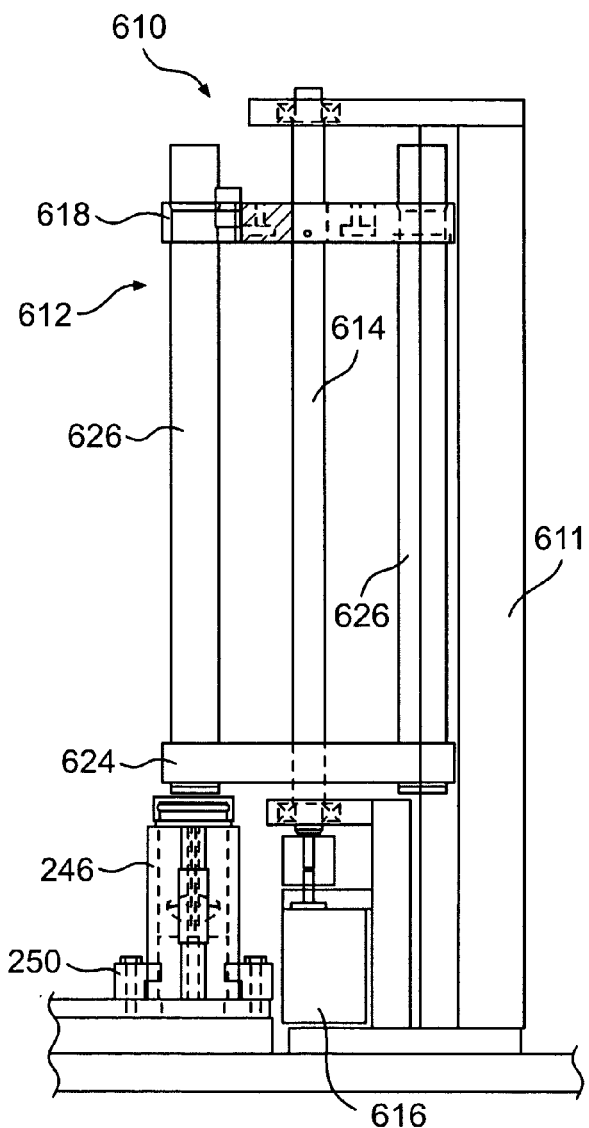 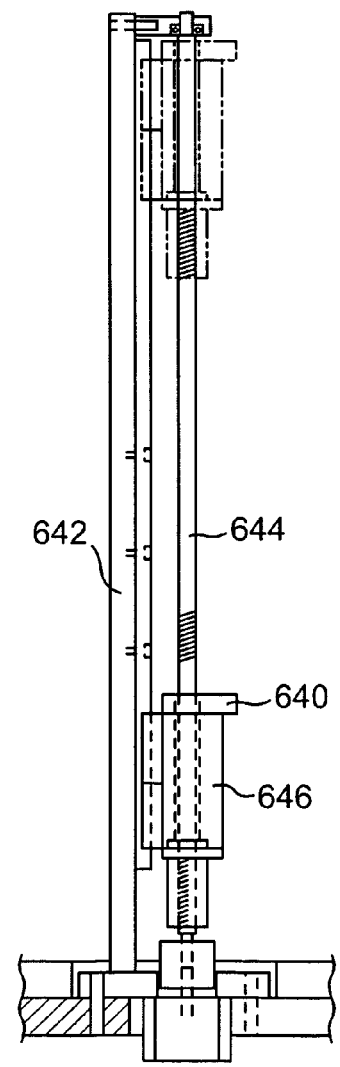
FIG. 37    FIG. 38

FLOW SENSOR OPERATION

SEQUENCE OF OPERATIONS

|  | V-1 | V-2 | V-3 | V-4 |
|---|---|---|---|---|
| #1 MEASURED PULL | ON | OFF | OFF | OFF |
| #2 TAMP PRINT | OFF | ON | OFF | OFF |
| #3 PURGE | OFF | OFF | ON | ON |

FIG. 49

APPARATUS AND METHOD FOR MIXING SPECIMENS IN VIALS

CROSS-REFERENCE TO RELATED APPLICATIONS

This application is a continuation of U.S. application Ser. No. 10/274,374, filed Oct. 21, 2002, now U.S. Pat. No. 6,883,958 which claims the benefit of commonly owned U.S. provisional application Nos. 60/330,092, filed Oct. 19, 2001, 60/372,080, filed Apr. 15, 2002, and 60/373,658, filed Apr. 19, 2002, all of which are incorporated herein by reference. This application also is related to commonly owned U.S. non-provisional application No. 10/122,151, filed Apr. 15, 2002, which is also incorporated herein by reference.

TECHNICAL FIELD

The present disclosure is directed to apparatus and methods for collecting and processing specimens of particulate matter-containing liquid, e.g., biological fluid, including collecting and depositing onto a microscope slide or other surface a uniform layer of particulates therefrom (e.g., cells) suitable for examination (e.g., use in cytology protocols).

BACKGROUND ART

Diagnostic cytology, particularly in the area of clinical pathology, bases cytological interpretations and diagnoses on examination of cells and other microscopic objects. The accuracy of the screening process and diagnosis, and the preparation of optimally interpretable samples from specimens typically depends upon adequate specimen and sample preparation. In this regard the ideal sample would consist of a monolayer of substantially evenly spaced cells, which enables cytotechnologists, cytopathologists, other medical professionals, and automated screening and diagnostic equipment to view or image the cells more clearly so that abnormalities can be identified more readily, more accurately and more reproducibly. Newer methodologies such as immunocytochemistry and cytometric image analysis require preparation apparatus and methods that are safe, effective, accurate, precise, reproducible, inexpensive, efficient, fast and convenient.

Cytological examination of a sample begins with obtaining specimens including a sample of cells from the patient, which can typically be done by scraping, swabbing or brushing an area, as in the case of cervical specimens, or by collecting body fluids, such as those obtained from the chest cavity, bladder, or spinal column, or by fine needle aspiration or fine needle biopsy. In a conventional manual cytological preparation, the cells in the fluid are then transferred directly or by centrifugation-based processing steps onto a glass microscope slide for viewing. In a typical automated cytological preparation, a filter assembly is placed in the liquid suspension and the filter assembly both disperses the cells and captures the cells on the filter. The filter is then removed and placed in contact with a microscope slide. In all of these endeavors, a limiting factor in the sample preparation protocol is adequately separating solid matter from its fluid carrier, and in easily and efficiently collecting and concentrating the solid matter in a form readily accessible to examination under a microscope.

Currently, biological specimens are collected for cytological examinations using special containers. These containers usually contain a preservative and transport solution for preserving the cytology specimen during shipment from the collection site to the diagnostic cytology laboratory. Further, cytology specimens collected from the body cavities using a swab, spatula or brush are also preserved in special containers with fixatives (e.g., alcohol or acetone fixatives) prior to transferring cells onto the slide or membrane for staining or examination. Specimen containers are known that allow a liquid-based biological specimen to be processed directly in the container so as to obtain a substantially uniform layer of cells on a collection site (in a filter housing defining a particulate matter separation chamber) that is associated with the container itself. See, for example, U.S. Pat. Nos. 5,301,685; 5,471,994; 6,296,764; and 6,309,362, of Raouf A. Guirguis, all of which are incorporated herein by reference.

The filtration techniques taught in these patents in practice have yielded fairly good results in terms of obtaining close to a monolayer of cells on slides, but there is room for improvement. Further, the types of specimen containers disclosed in these patents require specially configured apertured covers and adapters therefor that are designed to mate with the filter housing, and with suction equipment (e.g., a syringe or a mechanized vacuum source) used to aspirate liquid from the container and draw it through the filter. In addition, extraction of the filter so that it can be pressed against a microscope slide to transfer collected cells to the slide requires disassembly of the cooperating parts of the cover and/or adapters associated therewith. If the processing is done by automated equipment, special handling devices are required to carry out such disassembly. All of this complexity adds time, and material and labor cost to the processing required prior to the actual cytology examination.

In general, automated equipment thus far developed for processing liquid-based specimens have not performed with sufficient consistency, reliability, speed and automation to satisfy current and projected needs in cancer screening and other cytology-based medical, analytical, screening and diagnostic procedures. The vial-based automated processing system disclosed herein provides a safe, elegant and effective solution to these problems.

SUMMARY DISCLOSURE OF THE INVENTION

The specimen vial disclosed herein houses a complete processing assembly, typically one for mixing the liquid-based specimen therein and for holding a filter on which a uniform layer of cells can be collected from the specimen. It is expected that the specimen vial would be prepackaged with a liquid preservative solution, as is commonplace, and sent to the point-of-care site for specimen collection.

The processing assembly is coupled to a simple cover for the vial by means of a simple and inexpensive releasable coupling. When the cover is removed at the point-of-care site (physician's office, clinic, hospital, etc.), the processing assembly remains with the cover to allow medical personnel easy access to the container interior for insertion of a biological specimen into the vial. The cover, along with the attached processing assembly, is then replaced to seal the vial. The vial may then be sent to a laboratory for processing.

When the vial is manipulated in a simple way while still closed, the processing assembly detaches from the cover and remains in the vial for access by automated or manual laboratory equipment when the cover is subsequently removed. In a preferred embodiment, a downward force on the center of the cover is all that is required to detach the processing assembly from the cover. In contrast with the prior art specimen vials discussed above, the vial of the present invention requires no further interaction with the cover, which can be removed by a simple uncapping device and is discarded to avoid contamination. Ribs inside the vial support the processing assembly in the proper position for access during processing. This self-contained vial and processing assembly arrangement minimizes human operator exposure to biohazards, such as tuberculosis or other pathogens in sputum or in other specimens types, such as urine, spinal tap fluid, gastric washings, fine-needle aspirates, and gynecological samples.

The automated specimen processing apparatus disclosed herein is referred to as the "LBP" device (for liquid-based preparation), and is designed to produce slides of high quality and consistency. The LBP device also can be interfaced with a device for detecting and/or quantifying multiple morphologic, cytochemical, and/or molecular changes at the cellular level.

During the past two years or so, a review of the literature and reanalysis of existing data have led to the identification of a panel of molecular diagnostic reagents that are capable of detecting and characterizing lung cancer, which is the most common cancer, with high sensitivity and specificity. See, for instance, commonly owned U.S. patent application Ser. Nos. 10/095,297 and 10/095,298, both filed Mar. 12, 2002, and No. 10/241,753, filed Sep. 12, 2002. Here, the cells can be reacted with antibodies and or nucleic-acid "probes" that identify a pattern of changes that is consistent with a diagnosis of cancer. The molecular system can utilize algorithms fine tuned for that tumor heterogeneity.

Identifying molecular changes at the cellular level is one of the ways cancer can be detected early and at a more curable stage. Such molecular diagnostic devices can be used for early detection and diagnosis with the necessary sensitivity and specificity to justify their use as population-based screens for individuals who are at-risk for developing cancer. Such a molecular diagnostic device also can be used to characterize the tumor, thereby permitting the oncologist to stratify his/her patients, to customize therapy, and to monitor patients in order to assess therapeutic efficacy and disease regression, progression or recurrence. The availability of such tests will also foster the development of new and more effective therapeutic approaches for the treatment of early stage disease.

Such molecular diagnostics are designed to balance cost and test performance. While screening tests must exhibit high sensitivity and specificity, cost is always a critical factor, as the tests are typically directed to performing on a large number of individuals who, while at-risk, do not typically have symptomatic evidence of the disease. In this respect, the present LBP device can be interfaced with a molecular diagnostic device to develop a system for automatically diagnosing cancer, with a minimum or no human intervention. Alternatively, the present LBP device can be interfaced with a pathology work station, where medical professionals can observe individual slides prepared by the LBP device. The resulting diagnosing system, regardless whether an automated device or a manual observation device is interfaced, can be interfaced with an integrated data management system based on specialized software and a computer operating system to manage data entry and exchange of information, and network with the laboratory and hospital information systems.

The present LBP device transports multiple specimen vials of the novel type mentioned above sequentially through various processing stations and produces fixed specimens on slides, each slide being bar-coded and linked through a data management system to the vial and the patient from which it came. Fresh slides are automatically removed one at a time from a cassette, and each is returned to the same cassette after a specimen is fixed thereon. Multiple slide cassettes can be loaded into the LBP device, and the device will automatically draw fresh slides from the next cassette after all of the slides of the preceding one have been used. The slide cassettes preferably are configured for liquid immersion and interfacing with automated staining equipment that will stain the specimens without having to remove the slides from the cassette. In this regard the cassettes preferably have slots that allow for liquid drainage, and slots or other means that cooperate with the hooks normally used in the staining equipment to suspend other types of slide holders. The same slide cassettes are also configured to interface with automated diagnostic equipment and other devices that are part of an integrated system.

While specimen vials can be loaded into the transport manually, the full benefits of automation can be realized by using an optional vial handling system that automatically loads specimen vials for processing, and removes each one after its processing is complete. In one example of such a handling system the vials initially are loaded manually into special space-saving trays that hold up to forty-one vials each. Up to eight trays can be loaded into the LBP device, and the device will process all of them sequentially, removing one at a time from a tray and returning processed (and resealed) vials to a tray. The trays also can be used for storing and retrieving processed vials.

Each vial is transported through the LBP device on a computer-controlled conveyor, in its own receptacle. (In the example disclosed the conveyor has thirty receptacles.) The vials and the receptacles are keyed so that the vials proceed along the processing path in the proper orientation, and cannot rotate independently of its respective receptacle. They first pass a bar code reader (at a data acquisition station), where the vial bar code is read, and then proceed stepwise through the following processing stations of the LBP device: an uncapping station including a cap disposal operation; a primary mixing or dispersal station; a filter loading station; a specimen acquisition and filter disposal station; a cell deposition station; and a re-capping station. There is also a slide presentation station, at which a fresh microscope slide is presented to the specimen acquisition station for transfer of the specimen to the slide. Each of the stations operates independently on the vial presented to it by the conveyor, but the conveyor will not advance until all of the operating stations have completed their respective tasks.

The vial uncapping station has a rotary gripper that unscrews the cover from the vial, and discards it. Before doing so, however, the uncapping head presses on the center of the cover to detach the internal processing assembly from the cover. The primary mixing station has an expanding collet that grips the processing assembly, lifts it slightly and moves (e.g., spins) it in accordance with a specimen-specific stirring protocol (speed and duration). The filter loading station dispenses a specimen-specific filter type into a particulate matter separation chamber (manifold) at the top of the processing assembly. The specimen acquisition station has a suction head that seals to the filter at the top of the processing assembly and first moves the processing assembly slowly to re-suspend particulate matter in the liquid-based specimen. Then the suction head draws a vacuum on the filter to aspirate the liquid-based specimen from the vial and past the filter, leaving a monolayer of cells on the bottom surface of the filter. Thereafter the monolayer specimen is transferred to a fresh slide, and the vial moves to the re-capping station, where a foil seal is applied to the vial.

An improved filter system ensures that the highest quality monolayer specimens are produced. Specimen liquid flows through the filter as well as substantially across the front surface of the filter. Specifically, the specimen liquid is made to have a secondary flow component across the filter surface. The secondary flow is designed to flow radially outwardly or have a substantial radial component, which creates a shearing action that flushes or washes clusters of relatively weakly adhering particulates so that a more uniformly distributed and thinner layer can be formed on the front surface of the filter. In this respect, the present system includes a peripheral outlet through which specimen liquid can flow from the area adjacent the front surface of the filter.

The filter assembly preferably has a holder, a frit seated in the holder, and a membrane filter positioned over and in contact with the outer surface of the frit. The frit can extend beyond the end of the holder. The membrane filter can be attached to the holder. The sidewall portion extending beyond the holder forms an area through which the specimen liquid can flow, creating a secondary flow. The holder can be configured so that the frit is slightly bowed outwardly at the center so that when pressure is applied to a slide during the specimen transferring step, the central portion of the frit flattens to more evenly contact the membrane filter to the slide for more effective transfer.

The manifold at the upper end of the processing assembly seats the filter assembly with the membrane filter side facing down. The manifold preferably has a substantially conically configured bottom wall that rises from the central inlet (which communicates with the depending suction tube portion of the processing assembly). The filter assembly and the conically configured bottom wall form a manifold chamber that has a slight gap at its periphery, forming a peripheral outlet, by virtue of raised members or standoffs that act as spacers. The standoffs can have channels between them through which the specimen liquid can flow out of the manifold chamber.

Various preferred materials and possible alternatives are specified herein for several components of the system. It is to be understood that material choices are not limited to the specific materials mentioned, and that the choice of an alternate material is governed by many factors, among them functionality, molding accuracy, durability, chemical resistance, shelf life, cost, availability, and/or optical clarity (e.g., to address user requirements or marketing issues).

In its most basic aspect the invention claimed herein is directed to a method of mixing a specimen in an upstanding container having therein a mixer with a cavity defined by an upstanding annular wall. The method comprises the steps of engaging the annular wall of the mixer with a movable holder, elevating the holder and the engaged mixer sufficiently to prevent contact of the mixer with the container during mixing, moving the mixer to mix the specimen, and disengaging the holder from the mixer.

Another aspect of the claimed invention concerns apparatus for carrying out the above-described method. A clamping actuator selectively causes the holder to engage or release the annular wall of the mixer. The holder is mounted above the container for vertical movement relative thereto, and a vertical actuator effects vertical movement of the holder. A mixing actuator effects movement of the holder to cause the mixer to mix the specimen. A controller preferably coordinates operation of the actuators. The holder preferably fits within the cavity and is expanded into engagement with the annular wall. The holder preferably is an expanding collet having flexible fingers.

BRIEF DESCRIPTION OF THE DRAWING FIGURES

Preferred embodiments of the disclosed system and the invention, including the best mode for carrying out the invention, are described in detail below, purely by way of example, with reference to the accompanying drawing, in which:

FIG. 16 is an elevational view of an alternative embodiment of a gripper for the auto loader/unloader mechanism;

FIG. 17 is a perspective view of a specimen vial tray used in the auto loader/unloader mechanism;

FIG. 18 is an enlarged detail view taken at encircling line 18 in FIG. 17;

FIG. 23 is a facsimile of a computer screen;

FIG. 24 is a facsimile of another computer screen;

FIG. 25 is a facsimile of two computer screens;

FIG. 37 is a side elevational view of the magazine portion of the filter loading station of the LBP device;

FIG. 38 is a front elevational view of the pusher portion of the filter loading station;

FIG. 49 is an operation chart for the vacuum system of FIG. 48;

DETAILED DESCRIPTION OF BEST MODE

A full description of this vial-based specimen handling and processing system must begin with the vial itself, which consists of a container, a cover and a processing assembly (stirrer) in the vial.

Specimen Vial

Figure 1:
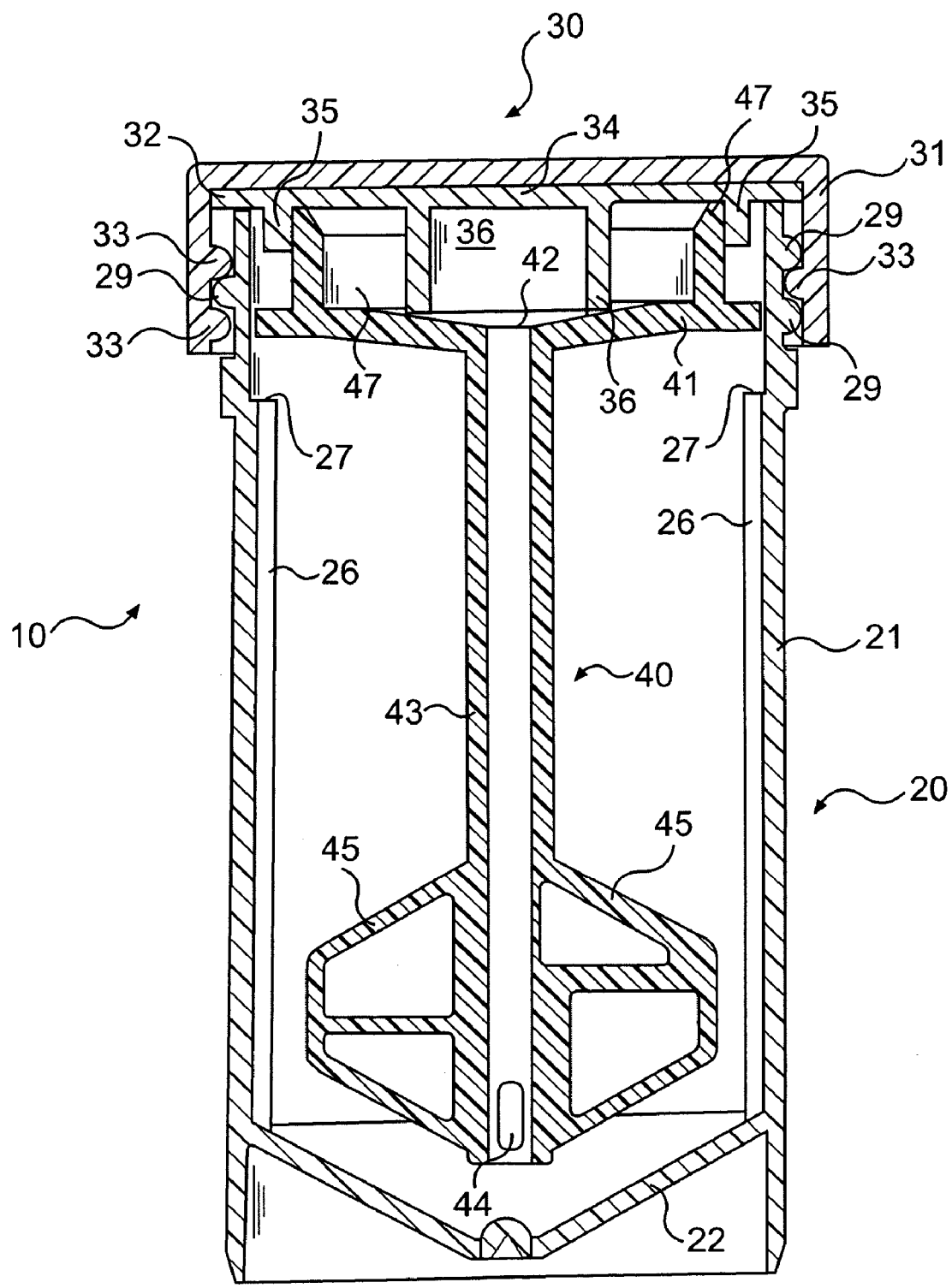
FIG. 1 is a vertical sectional view through a specimen vial for use with the LBP device, showing the processing assembly (stirrer) in the vial coupled to the cover.
Figure 2A:
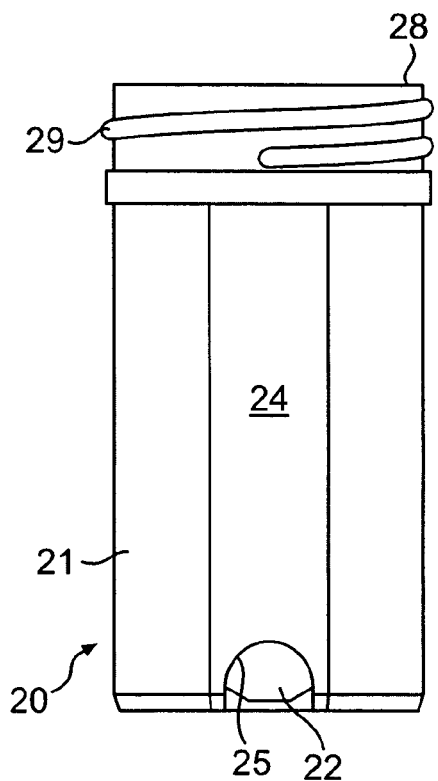
FIG. 2a is a front elevational view of the container portion of the vial.
Figure 2B:
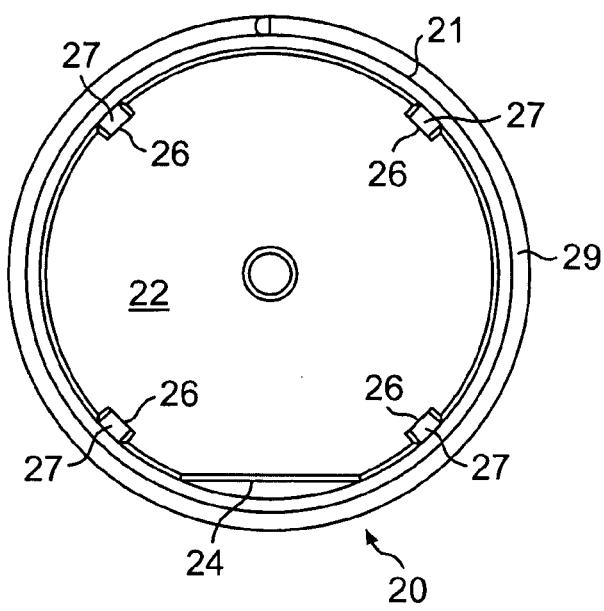
FIG. 2b is a top plan view of the container, shown with the stirrer removed.

Referring to FIGS. 1, 2a and 2b, the vial 10 comprises a container 20, a cover 30 and a processing assembly 40. Processing assembly 40 is designed to carry out several functions, among them mixing, and for this preferred rotary embodiment will be referred to as a stirrer for the sake of convenience. Container 20 preferably is molded of a translucent plastic, preferably polypropylene, and has a substantially cylindrical wall 21, surrounding its longitudinal axis, joined to a conical bottom wall 22. Possible alternative plastics include ABS and polycyclohexylenedimethylene terephthalate, glycol (commercially available from Eastman Kodak Co. under the name EASTAR7 DN004). A small portion 24 of wall 21 preferably is flat, the outer surface of the flat portion adapted to receive indicia, e.g., a bar code label, containing information concerning the specimen placed in the vial. Although only one flat portion is shown, the container could be configured without a flat portion, or with two or more flat portions, each adapted to receive indicia. Alternatively, the indicia could be located on a curved portion of wall 21. The bottom end of flat portion 24 has an arcuate notch 25 which acts to keep the container in a proper orientation when handled by the LBP device, which as noted is designed to cradle the container and move it through various processing stations. A differently shaped notch (e.g., V-shaped) can be used as long as the notch properly mates with the LBP device. Other suitable mating structures can be used instead.

Figure 10:
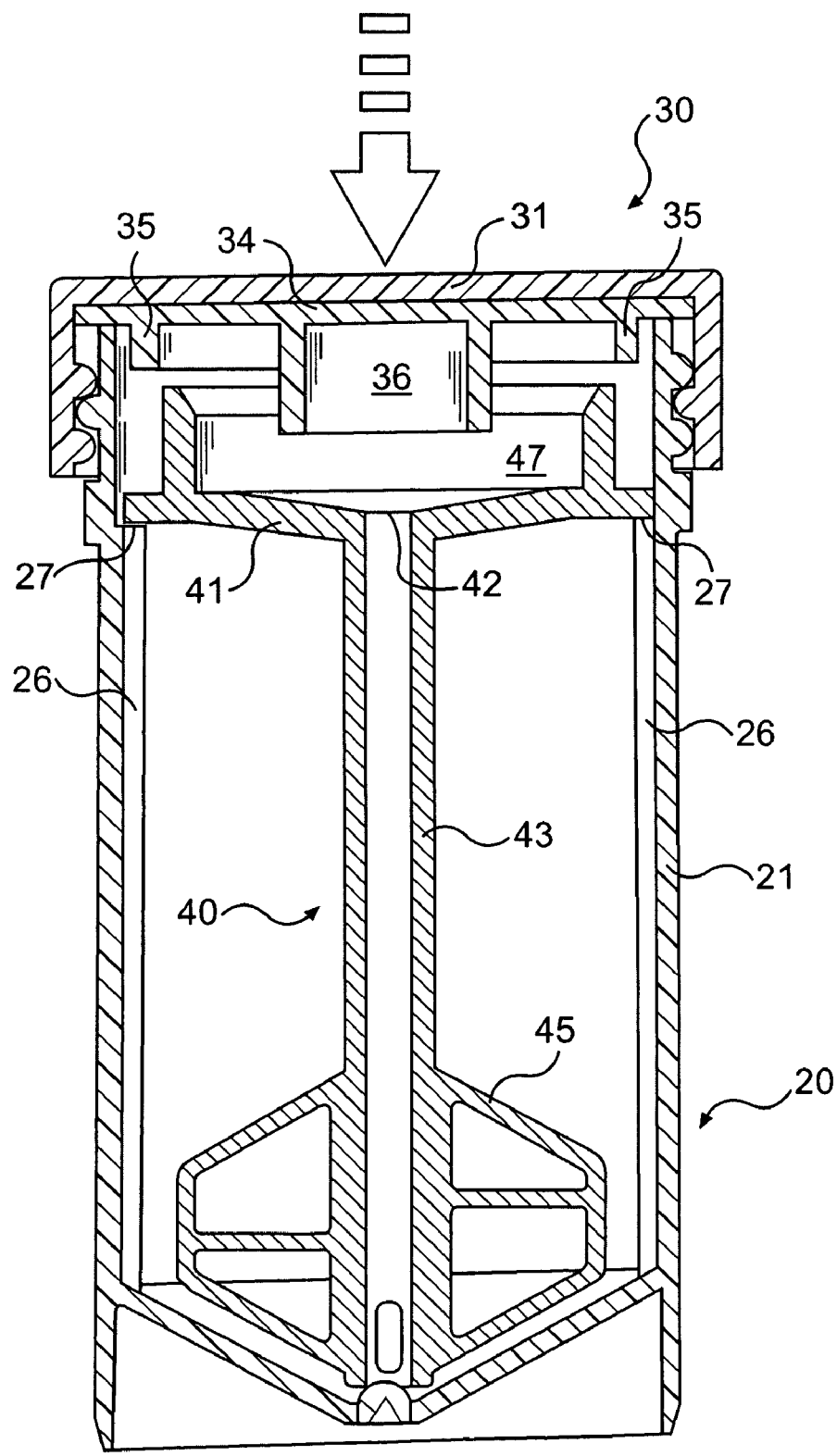
FIG. 10 is a vertical sectional view of the specimen vial similar to FIG. 1, but showing the stirrer detached from the cover.

Four longitudinal ribs 26 project inwardly from wall 21. The upper ends 27 of ribs 26 form rests for the stirrer 40 when it is detached from cover 30 (see FIG. 10). The top of container 20 has an opening 28 and a standard right-hand helical thread 29 that preferably extends for one and one half turns and mates with a similar thread on cover 30. Other types of cover-to-container coupling may be used, such as a bayonet coupling, snap-fit arrangement, etc.

Figure 4:
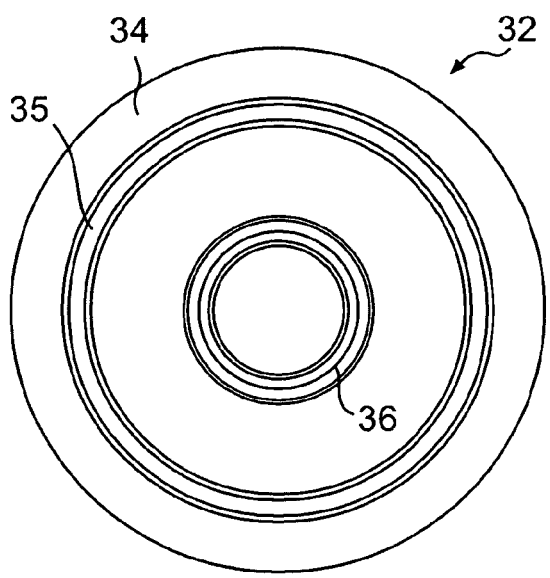
FIG. 4 is a bottom plan view of the liner that fits within the cover.

Cover 30 comprises a commercially available simple molded plastic threaded cap 31, and a novel liner 32 retained in the cap. Cap 30 preferably is molded of polypropylene, but ABS and EASTAR7 DN004, among others, are alternative plastic material choices. Cap 31 has a flat solid top, and an externally knurled depending flange with an internal helical thread 33 that mates with thread 29 on container 20. Referring to FIG. 4, liner 32 is molded of plastic material, preferably polyethylene, and has a substantially flat base 34 sized to fit snugly within cap 31, behind thread 33, so that the liner is not readily separated from the cap. As seen in FIG. 1, liner base 34 serves as a gasket-type seal between the cap 31 and the rim of the container wall 21.

Liner base 34 has a coupler in the form of an annular projection 35 that preferably is slightly conical in shape, preferably forming an angle of about 5° to its central axis.

In other words, the inner diameter of annular coupler 35 is greater at its proximal end, where it joins liner base 34, than at its distal end. Liner base 34 also has a central annular boss 36 that projects further from base 34 than annular coupler 35 so as to interact with stirrer 40, as described below. While the use of a separate liner mated to a standard cap is preferred, the cover could be integrally molded in one piece to include the annular coupler 35 and the central annular boss 36. Such a one-piece cover (or even the two-piece cover described above) could instead be configured to act as a plug-type seal by projecting into and sealing against the inside of the rim of container wall 21.

Figure 3:
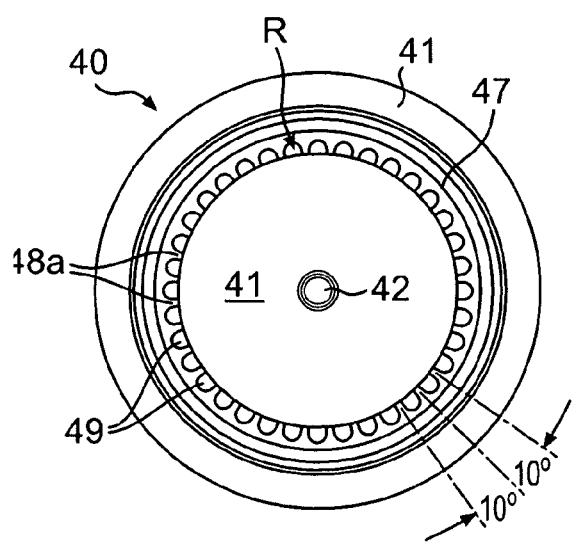
FIG. 3 is a top plan view of the stirrer.
Figure 5:
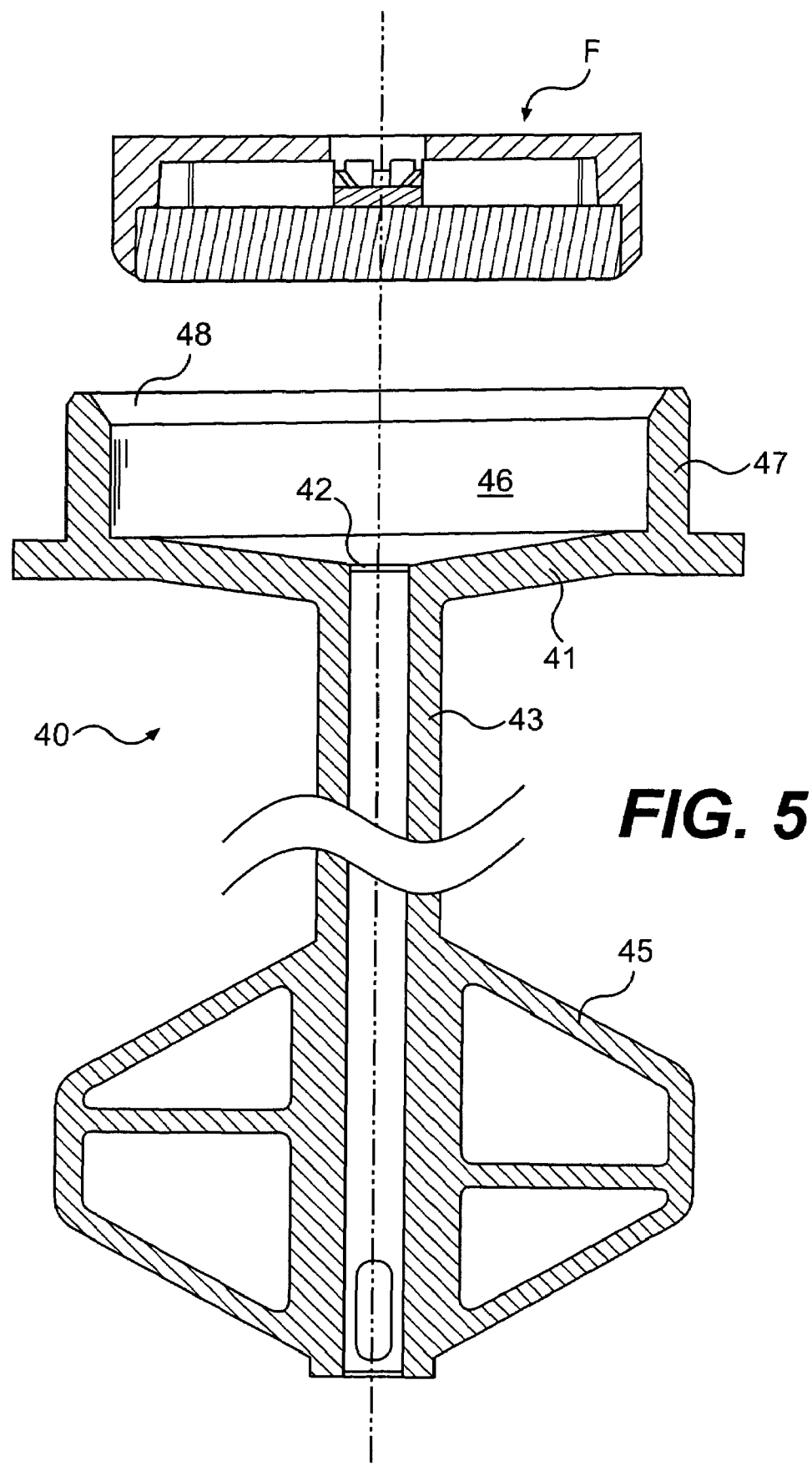
FIG. 5 is an exploded vertical sectional view of the stirrer and a filter assembly adapted for use in the stirrer.

Referring to FIGS. 1, 3 and 5, stirrer 40 is molded of plastic, preferably polypropylene, and has a circular base or bottom wall 41, sloped at its center, with a central inlet port 42; a central depending suction tube 43 with two diametrically opposed suction ports 44 near the bottom of the tube; and a dispersing (mixing) element in the form of laterally extending vanes 45. The upper portion of the stirrer 40 has a cup-shaped particulate matter separation chamber or manifold 46 defined by base 41 and an upstanding annular wall 47. The upper edges of wall 47 are beveled, the inner edge 48 preferably being beveled to a greater degree to facilitate placement of a filter assembly F in manifold 46, as described below. Possible alternative plastic material for the stirrer include ABS and E$_{ASTAR}$7 DN004.

Annular wall 47 serves as a coupler for releasably coupling the stirrer 40 to cap liner 32, and is therefore dimensioned to fit snugly within annular coupler 35 (see FIG. 1). Specifically, there is a friction or press fit between couplers 35 and 47 such that normal handling of the closed vial, and normal handling of cover 30 when removed from container 20 (e.g., to place a biological specimen in the container) will not cause separation of the stirrer from the cover. Coupler 47 is dimensioned relative to coupler 35 so that there is a very slight initial diametrical interference, preferably about 0.31 mm. Coupler 47 is stiffer than coupler 35, so assembly of the stirrer to the cover involves slight deformation principally of coupler 35, resulting in a frictional force that keeps the stirrer and the cover engaged. Application of an external force to the vial that overcomes this frictional retention force will cause stirrer 40 to detach from cover 30 and drop by gravity further into container 20 (see FIG. 10).

The external separation force preferably is applied to the central portion of cover 30 (see the arrow in FIG. 10), which deflects cap 31 and liner 32 inwardly. As illustrated in FIG. 1, central boss 36 on liner 32 is dimensioned such that its distal end just contacts or lies very close to base 41 of the stirrer. Thus, when the central portion of the cover is depressed, central boss 36 will deflect further than annular coupler 35 on liner 32 and push stirrer 40 out of engagement with coupler 35. Inward deflection of liner 32 also causes coupler 35 to spread outwardly, thereby lessening the retention force and facilitating detachment of the stirrer. The separation force applied to cover 30 and required to detach the stirrer should be in the range of 5 to 30 lbs., preferably about 12 lbs.

Once detached from the cover 30, stirrer 40 comes to rest on the upper ends 27 of ribs 26. See FIG. 10. The particulate matter separation chamber (manifold) 46 thus is stably supported near the container opening and easily accessed by the LBP processing heads, which will manipulate the stirrer so as to process the specimen directly in the container. At least three ribs 26 are required to form a stable support for the stirrer, but four are preferred because that number seems to promote more thorough dispersion of the particulate matter in the liquid during stirring. Should the stirrer inadvertently become detached from the cover at the point-of-care site, the physician or an assistant simply places the stirrer loosely in the vial so that it descends into the specimen and then screws the cover on as usual. This is not difficult because the ribs in the vial allow insertion of the stirrer in only one direction. Once the vial is closed with the specimen inside, the stirrer remains in the vial throughout processing and is sealed therein when the vial is re-capped.

Figure 10A:
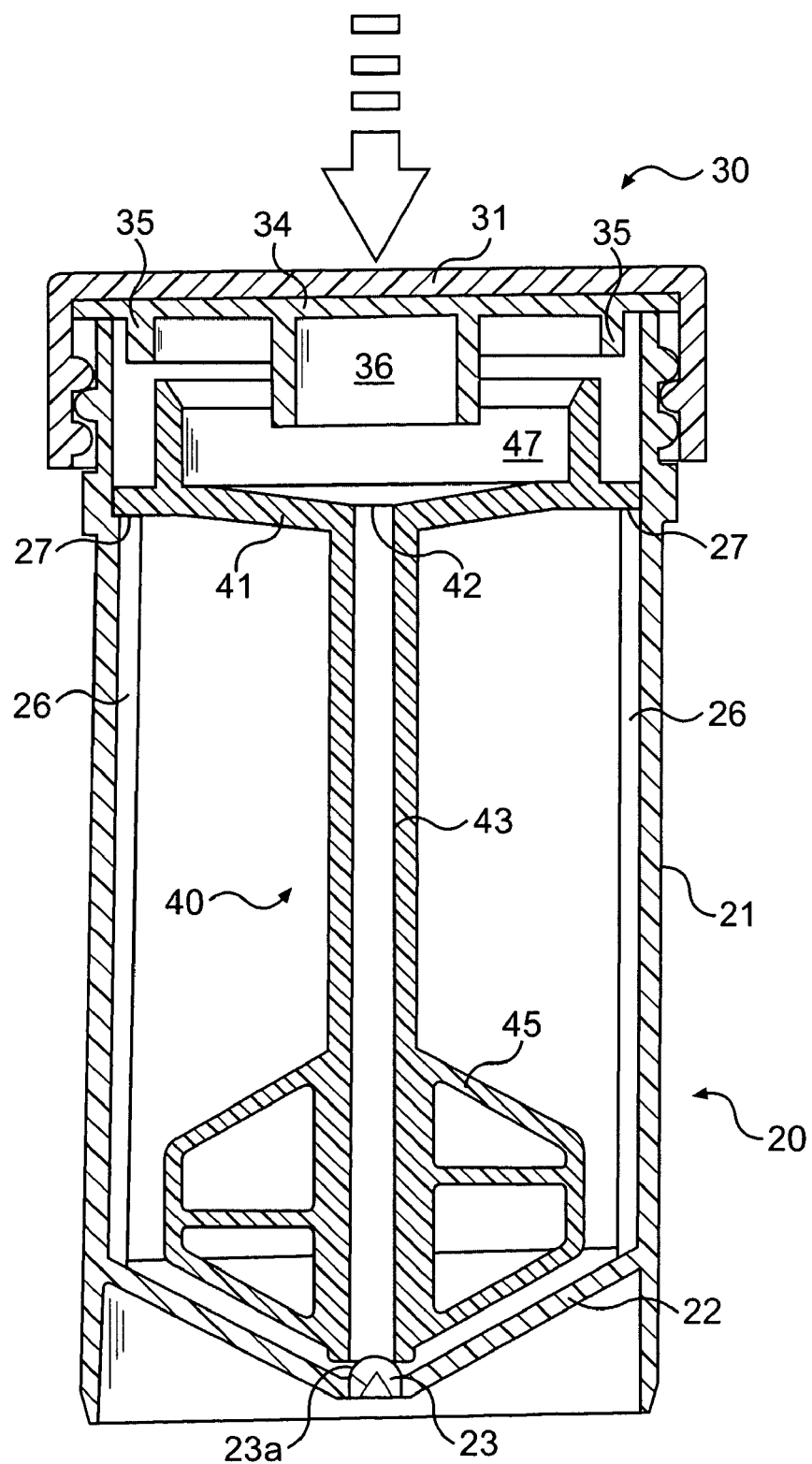
FIG. 10a is a partial vertical sectional view similar to FIG. 10, showing a modification of the stirrer.

A small percentage of patient specimens, as may be found in gynecological Pap test and other specimen types, contain large clusters of cells, artifacts, and /or cellular or noncellular debris. Some of these large objects, if collected and deposited on a slide, can obscure the visualization of diagnostic cells and, consequently, result in a less accurate interpretation or diagnosis of the slide sample. Since most of these features are not of diagnostic relevance, their elimination from the sample is, in general, desirable. To achieve this result, the side suction ports 44 in the stirrer suction tube 43 preferably are eliminated (see FIG. 10a) in favor of close control of the interface between the bottom of the suction tube 43 and the small projection 23 at the center of bottom wall 22 of the container 20. This interface effectively forms a metering valve whose geometry (orifice) 23a is created when the stirrer 40 rests on the ribs 26 of the container 20 (see FIG. 10). Proper sizing of the annular flow orifice 23a prevents large objects from entering the suction tube 43, while allowing the passage of smaller objects that may be diagnostically useful. While the orifice 23a has a thin passage section and a small metering area, clogging is not an issue due to its large diameter. The annular orifice 23a preferably has an outside diameter on the order of 0.105 in. and an inside diameter on the order of 0.071 in., yielding a passage width on the order of 0.017 in. This orifice size is optimized for gynecological specimens.

Filter System

Figure 6:
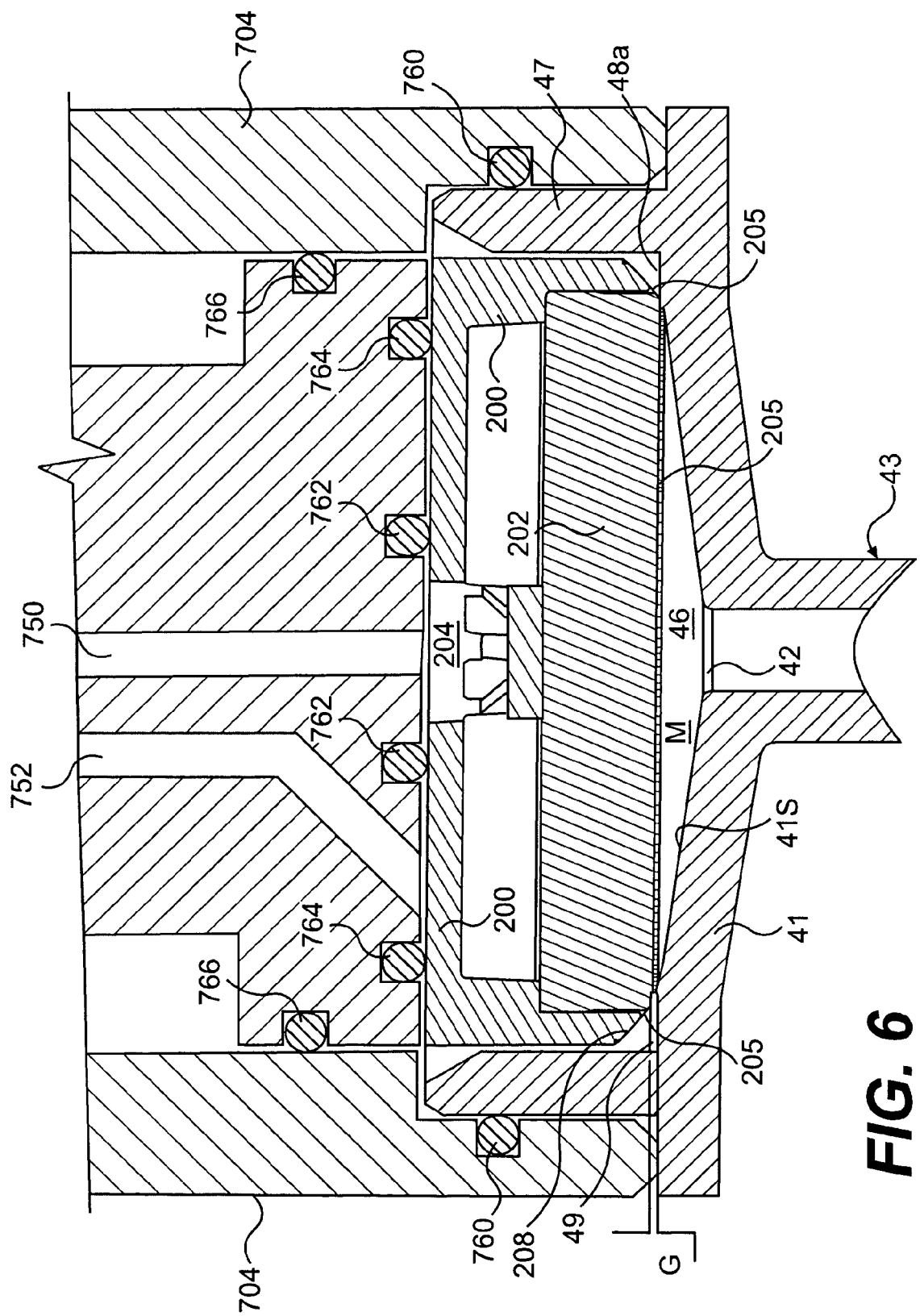
FIG. 6 is a vertical sectional view of the upper portion of the stirrer, showing the filter assembly in place in the particulate matter separation chamber.
Figure 8:
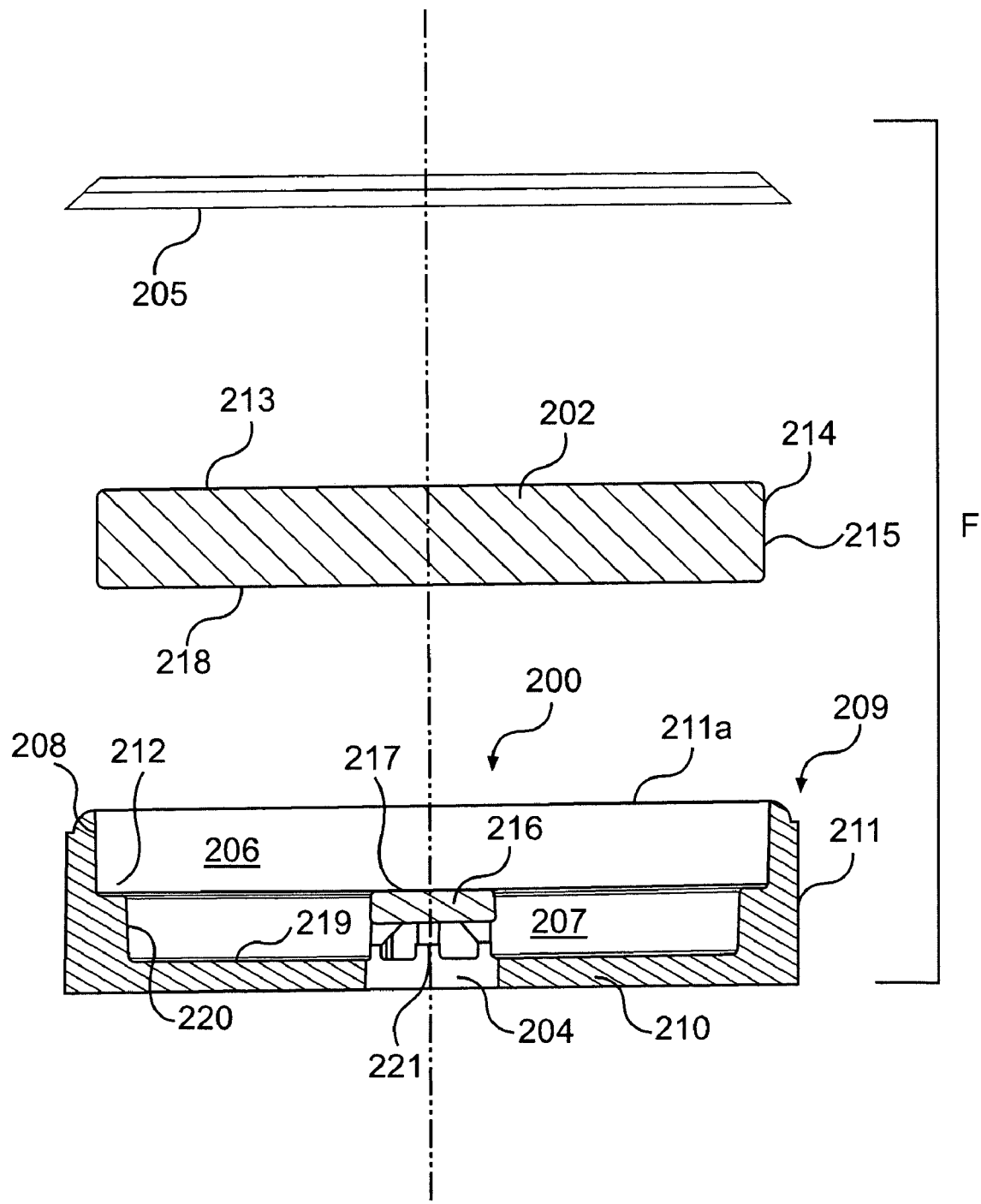
FIG. 8 is an exploded, cross-sectional view of the filter assembly.

FIGS. 6 and 8 illustrate one embodiment of a filter assembly F according to the present invention. FIGS. 3 and 6 illustrate one embodiment of a manifold 46 (in stirrer 40) according to the present invention. The filter system includes the filter assembly F and the manifold 46.

Referring to FIGS. 6 and 8, the filter assembly F comprises a filter housing or holder 200, a porous frit 202, and a porous membrane filter 205. FIG. 8 shows these components more clearly in an exploded view. The holder 200 can be cup- or container-shaped, having a recess or cavity 206 for seating the frit 202 and a chamber 207 between the frit 202 and the holder 200. The frit 202 and the membrane filter 205 can be made of the materials disclosed in the Guirguis patents identified above, namely U.S. Pat. Nos. 5,301,685 and 5,471,994, the disclosures of which are incorporated herein by reference.

In the present filter assembly F the membrane filter 205, the frit 202, and the holder 200 are assembled together as a unit. The frit 202, which has a cylindrical shape, is first seated in the holder 200. Then the membrane filter 205 is permanently affixed, adhered, joined, or fused to the holder 200. In the illustrated embodiment, the outer perimeter or edge of the membrane filter 205 is fused to the holder 200. In this regard, the holder 200 has a bevel or chamfer 208 formed around an outer circumferential corner 209. The chamfer 208 provides an angled surface to which the membrane filter 205 can be attached using a conventional bonding technique, such as ultrasonic welding. The holder 200 and the membrane filter 205 should be made of materials that will fuse together. Preferably both are made of polycarbonate, although an ABS holder will work with a polycarbonate membrane filter. Thermoplastic polyester could be used for the holder if the membrane filter is made of the same material. The frit 202 preferably is made of polyethylene.

Referring to FIG. 8, the holder 200 preferably is cylindrical and comprises a substantially cup-shaped body having a bottom wall or base 210 and a substantially upright cylindrical sidewall 211 extending therefrom and terminating in a rim 211a. The sidewall 211 has an annular shoulder 212 extending radially inwardly, toward the center. The shoulder 212 acts as a seat that accurately positions the frit 202. Frit 202 preferably is dimensioned so that the frit's outer or front face 213 is proud of (extends beyond) the rim 211a when the peripheral portion of the frit's rear face abuts the shoulder 212.

The inner diameter of the sidewall 211 can be dimensioned to frictionally engage and hold the frit 202 in place. In this respect, the frit's outer diameter can substantially correspond to the inner diameter of the sidewall 211 to mechanically, i.e., frictionally, hold the frit 202 in place. However, since the membrane filter 205 covers the frit 202, the frit need not be frictionally held to the holder. That is, the frit 202 can be loosely seated in the holder. Frictionally seating the frit 202 in the holder 200, however, maintains the frit 202 in place so that attachment of the member filter 205 can be done at a remote site. It also simplifies and reduces the cost of mass production of filter assemblies because the holder 200 and the frit 202 can be joined to make a secure subassembly and stored for later attachment of the membrane filter 205.

Figure 7A:
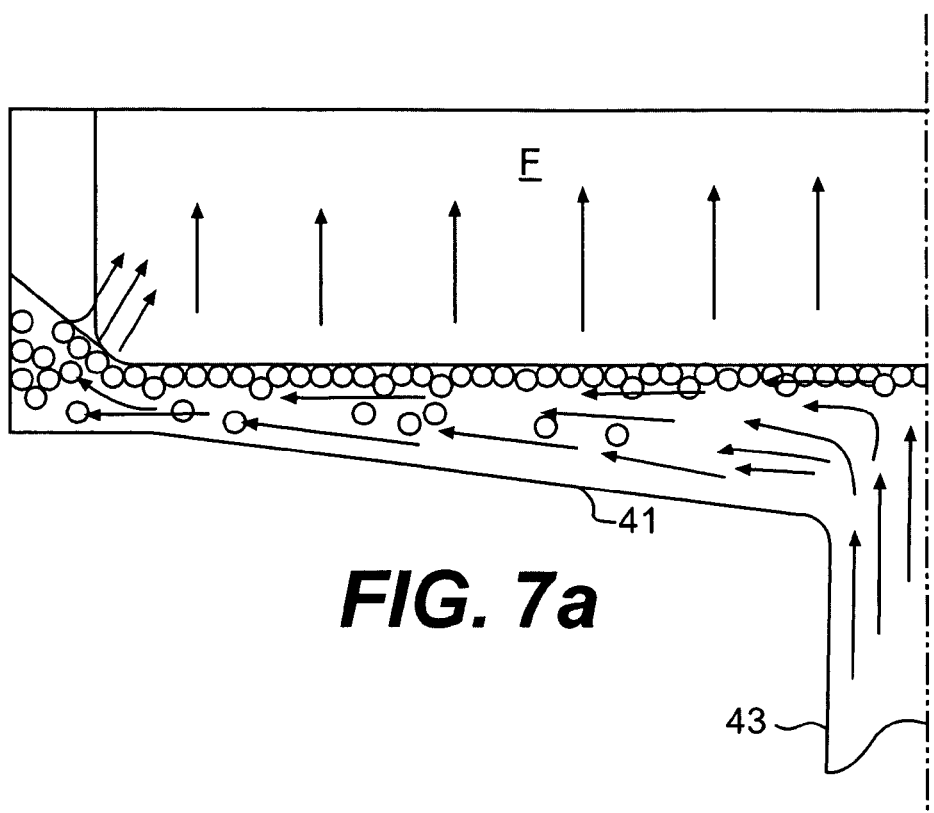
FIG. 7a is a partial schematic view of the arrangement depicted in FIG. 6, showing the flow of liquid and particulate matter separated therefrom.

After the frit 202 is seated in the holder 200, the membrane filter 205 is draped over the frit's outer face 213 and the exposed portion 214 of the frit's side wall 215 that extends beyond the holder 200, and is attached to the chamfer 208, as is better seen in FIG. 6. The frit's exposed outer sidewall portion 214 provides an annular surface area through which the specimen liquid can flow to provide a dual flow path, as schematically illustrated in FIG. 7a.

The filter assemblies F can be coded to denote different pore size and pore density (number of pores per unit cross-sectional area) as may be required for specific processing protocols. Color coding of filter assemblies is preferred, although any form of machine-detectable coding can be used, including distinguishing projections, such as small nipples, for tactile-based sensor recognition. The LBP device is provided with a sensor that can discriminate between these colors or other codes to ensure proper filter selection. The filter assemblies also can be provided in paper carriers for easy insertion into the LBP device.

Referring back to FIG. 8, the holder's bottom wall 210 has a central opening 204 through which vacuum can be applied to draw specimen liquid therethrough. The holder 200 further includes a central projection or protrusion 216 extending into the holder from the bottom wall 210. The central protrusion 216 is aligned with the opening 204 and positioned in the chamber 207, which is defined by the frit's inner face 218, the inner face 219 of the bottom wall 210 and the inner side 220 of the sidewall 211. The protrusion 216 is substantially hollow and has a plurality of side openings 221 that distribute vacuum to the chamber 207 and provide a substantially symmetrical flow through the chamber. The specimen liquid drawn through the membrane filter 205 and the frit 202 fills the chamber 207 and exits the chamber 207 through the side openings 221 and the central opening 204.

The protrusion 216 has an abutting surface 217 that faces and extends toward the holder's open face. The abutting surface 217 is configured to abut against the frit's rear face 218. In particular, the abutting surface 217 is slightly proud of the annular shoulder 212. That is, the abutting surface 217 lies slightly above or beyond the level of the annular shoulder 212 so that the frit's outer face 213 bows slightly outwardly when the frit is installed in the holder. For example, the abutting surface 217 can extend beyond the height of the annular shoulder 212 by about 0.002 inch. The resulting slight bow created by the protrusion pushing out the central portion of the frit 202 ensures that the central part of the membrane filter 205 contacts the slide. The pressure applied to the slide during imprinting flattens the frit's front surface 213, ensuring full contact of the membrane filter 205 with the slide to more effectively transfer the collected particulates to the slide and minimizing any deposition artifacts. If this slightly bowed configuration is desired, the frit 202 preferably is securely seated in the holder 200, such as by friction as previously explained.

Due to the bowed frit configuration, the membrane filter 205 need not be taut. This simplifies the manufacturing process, reduces cost, and reduces the rejected part rate. Anything short of a major wrinkle can work effectively. As noted, the frit 202 preferably is slightly deformable, its compliance allowing it to flex and flatten against a glass slide post aspiration to transfer cells and other objects of interest from the filter to the slide. To accomplish this the frit should have an elasticity that allows it to be crushed flat by application of a force of 8 lbs. through a displacement of 0.0016 in. Good frit materials include sintered polyethylene and sintered polyester. The frit 202 may be a porous material, with spatially random pores, typically with pore sizes in the range of about 50-micrometer to 70-micrometer. A significant attribute of this material is that it is of low fluidic impedance relative to the material of the thin membrane filter 205 (which typically has pore sizes of about 5-micrometer to 8-micrometer). In other words, the pressure drop across the frit 202 is much less than the pressure drop across the membrane filter 205. Thus, fluid that passes through the filter flows freely through the frit. Alternatively, instead of having randomly positioned pores, the frit 202 may be made of a material or structure that has many parallel channels of small (e.g., 50-micrometer to 70-micrometer) inner diameters through which aspirated fluid and particulates may flow. Such a parallel-channel arrangement would behave as an inner fluid-pervious medium with an apparent low fluidic impedance. In fact, any material or device with the proper low fluidic impedance and deformability/resilience characteristics may be used in the specimen acquisition station, whether it has pores or not.

Figure 7B:
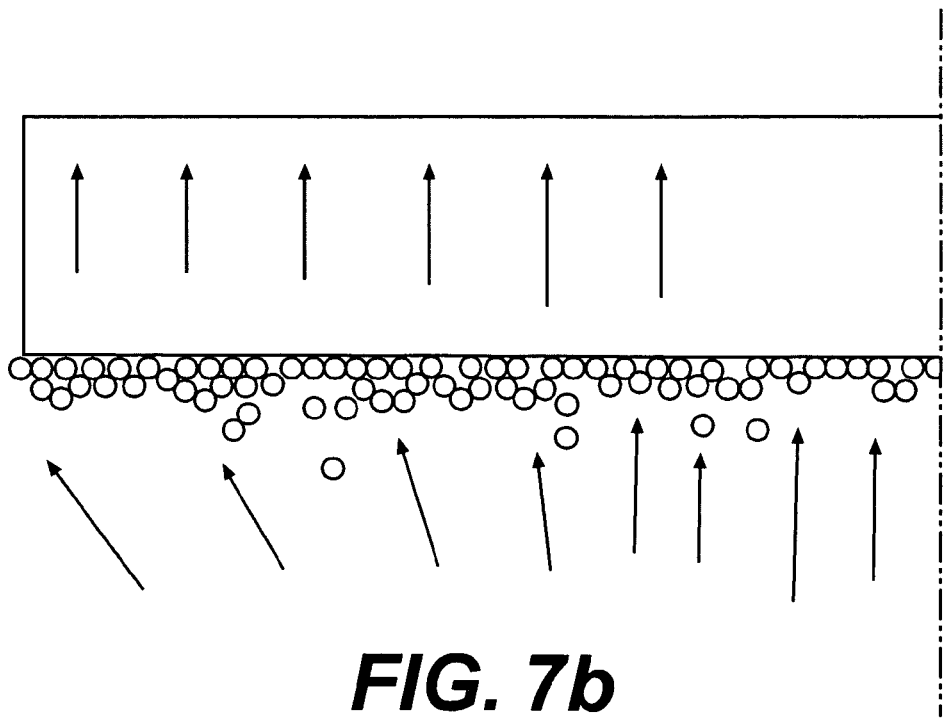
FIG. 7b is a view similar to FIG. 7a, showing liquid flow in a prior art filter system.

It has been found that flowing the specimen liquid substantially or mostly in an axial direction, i.e., perpendicular to the membrane filter, can accumulate layers or clusters of particulates, as schematically illustrated in FIG. 7b, particularly if the vacuum is applied through the membrane filter for a longer period than necessary. This can happen even with the Guirguis dual flow design, which provides some secondary flow components that are radially directed. See, for example, FIGS. 4 and 12 of Guirguis' U.S. Pat. Nos. 5,471,994 and 5,301,685. It seems that the secondary flow generated by that configuration is insufficient to create an effective flushing, or shearing action across the membrane filter. An earlier Guirguis patent, namely U.S. Pat. No. 5,137,031, discloses a funnel- or cone-shaped manifold. In that arrangement, however, there is no secondary radial outflow at its periphery. As there is no flow other than directly through the filter itself, there is no substantial radial flow component. Accordingly, the specimen liquid only flows substantially perpendicularly to the membrane filter.

Referring to FIG. 6, the inner diameter of the upright wall 47 of the manifold 46 at the top of stirrer 40 is dimensioned to be slightly larger than the outer diameter of the filter assembly F, namely the holder's sidewall 211, so that the manifold 46 can receive and seat the filter assembly F, with the membrane filter 205 facing down, as illustrated. The filter assembly F can be loosely seated in the manifold 46. When the filter assembly F is seated in the manifold 46, the outer peripheral edge of the membrane filter 205 rests on the bottom wall 41. The bottom wall 41 is configured to have a well or recess that forms a manifold chamber M when the filter assembly F is seated in the manifold 46. The chamber M is thus bounded by the outer surface of the membrane filter 205 and the upper surface 41S of the bottom wall 41.

The present dual flow arrangement solves the problem of particulate build-up or accumulation on the face of the membrane filter. This arrangement causes a shearing force or action across the front face of the membrane filter that is sufficient to flush the particulates aside and keep them from building up or layering. Built-up or layered particulates have a weaker bond to the layer underneath them as they build up, because the suction power decreases as the pores of the membrane filter 205 become covered with particulates. A shearing force is created by imparting a tangential or substantially radial flow component to the specimen liquid across the front face of the membrane filter 205. This flow component is substantially parallel to the front face of the membrane filter, i.e., it is perpendicular to the built-up direction of the layers, and flushes the particulates radially outwardly, away from the front face of the membrane filter.

To provide a secondary or radial flow path, the manifold 46 is configured to provide a small spacing or gap G (see FIG. 6) at the periphery of the manifold chamber M, between the front face of the membrane filter 205 and the upper surface 41S of the bottom wall 41, to allow flushed particulates to exit the manifold chamber M, away from the front face of the membrane filter. The gap G must be large enough to prevent the particulates from clogging it. That is, if the gap G is made too small for the particulates being filtered, the gap G can get clogged, cutting off the secondary flow. The minimum size of the gap ultimately depends on the particulate size, the viscosity of the specimen liquid, and the temperature of the specimen liquid. It has been determined that the gap G should be at least 0.004 in. to prevent clogging by cellular particulates.

Referring to FIGS. 3 and 6, to create the gap G, which forms an outflow nozzle, the bottom wall 41 of manifold 46 includes a plurality of spaced standoffs or raised ribs 48a around the periphery of the manifold 46. The spaces 49 between the ribs 48a provide a passage for specimen liquid to exit the chamber M. In the illustrated preferred embodiment, the manifold 46 has an inner diameter of 23.4 mm, and has thirty-six ribs 48a, evenly spaced at 10°. The ribs are 0.150 mm high and arcuately blend into the surrounding shoulder with a radius R of 0.63 mm, as illustrated. Of course, the present invention contemplates other configurations of spaced ribs or standoffs, which are intended to precisely space the filter assembly from the bottom wall 41 so that a precise outflow area is created. Depending on the number and thickness of ribs or standoffs, the total outflow area can be reduced as much as 50% as compared to the inlet area.

Figure 9:
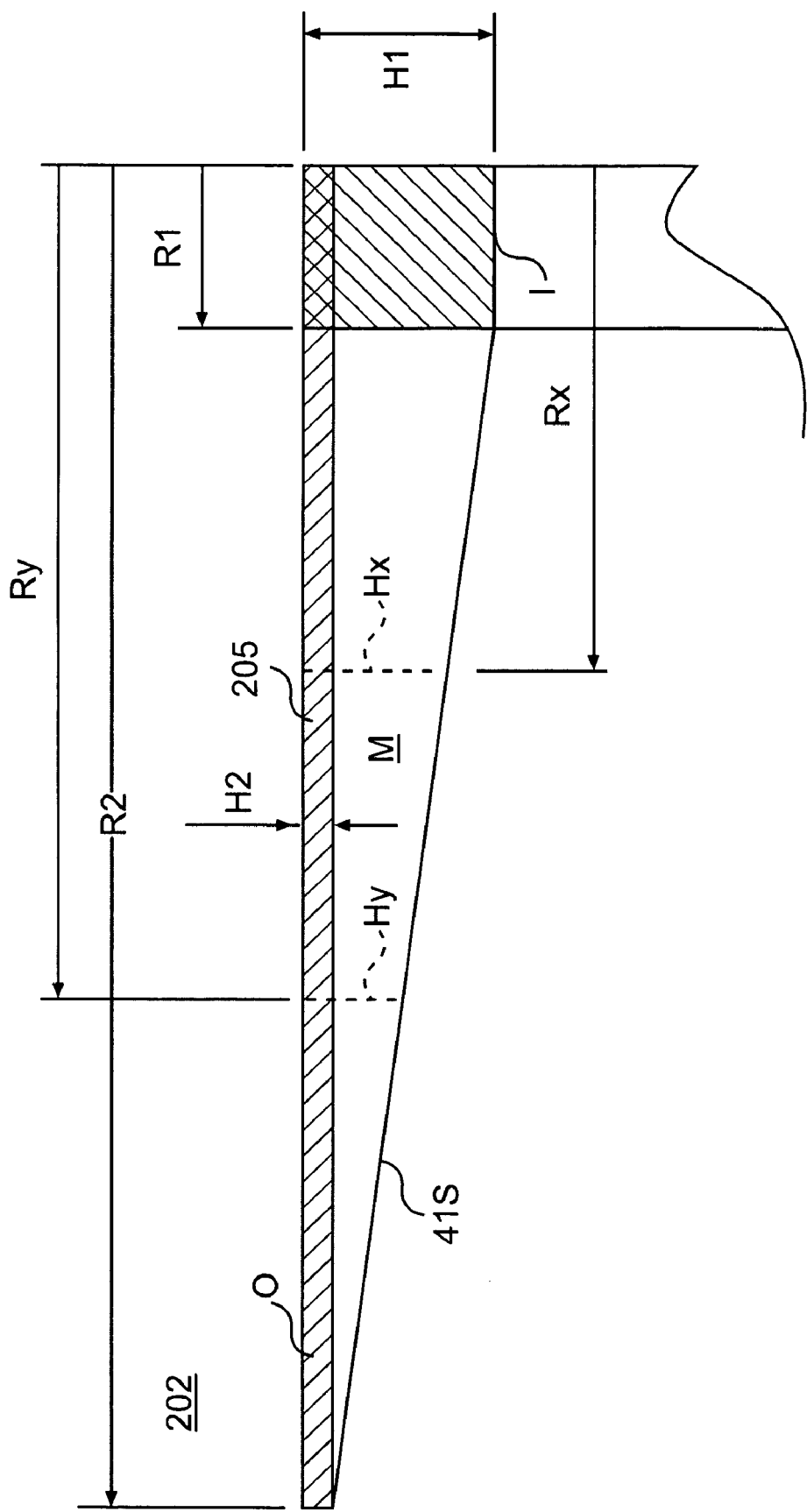
FIG. 9 is a schematic illustration of the dimensional configuration of the flow manifold.

It has been observed in the Guirguis type filter arrangement referred to above that specimen liquid traveling radially outwardly loses velocity. The present dual flow filter system compensates for the velocity slowdown by providing a shallow, substantially conical surface across which the specimen liquid flows. This surface forms a substantially conical distribution manifold chamber M confronting the membrane filter 205. The chamber M according to the present invention has an annular radial outlet O, through spaces 49, having an area that is about equal to or smaller than the maximum area of the central inlet I. Referring to FIG. 9, the "face" area of the radially directed annular flow passage is cylindrical and is defined (bounded) at any given radius $R_1$, $R_x$, $R_y$, . . . , $R_2$ by the front surface of the membrane filter 205 and the conical surface 41S of the manifold. As the specimen liquid travels outwardly, the radius increases while the manifold height decreases. The manifold chamber M can be configured so that the height $H_1$, $H_x$, $H_y$, . . . , $H_2$ decreases at a rate which maintains the face area of the annular passage substantially uniform from the inlet I to the outer perimeter outlet O of the manifold, yielding a substantially linear radial flow velocity across the face of the membrane filter 205.

In this regard, still referring to FIG. 9, the maximum theoretical radial flow area of a round manifold inlet I can be defined as the circumference ($2\pi R_1$) multiplied by the height of the manifold chamber $H_1$. In this instance, $2\pi R_1 H_1$ defines the total circumferential area of the manifold inlet I. The maximum circumferential flow area of a round manifold outlet O can be defined as $2\pi R_2 H_2$. If the outlet flow area is to equal the inlet flow area, then the inlet and outlet areas can be expressed as:

$$2\pi R_1 H_1 = 2\pi R_2 H_2$$

$$R_1 H_1 = R_2 H_2$$

Using this expression, the heights, e.g., $H_x$, $H_y$, can be defined at their given radii, e.g., $R_x$, $R_y$ from the inlet I to the outlet O. If the heights $H_1$, . . . , $H_x$, . . . , $H_y$, . . . $H_2$ from the inlet to the outlet are plotted, the resulting surface 41S would be curved, not linear. However, it has been observed that a significantly curved lower manifold surface does not work as effectively as a linear surface 41S. Accordingly, the present preferred embodiment contemplates a linear or substantially or nearly linear surface 41S (which can be slightly curved) extending from the inlet to the outlet. Also, there is a minimum height $H_2$ of about 0.006 inch clearance for the specimen liquid to effectively flow. Based on this requirement, the minimum $R_1$ can be defined as $0.006 R_2/H_1$ inches. With this configuration, as the specimen liquid is drawn through the filter, the specimen liquid traverses the front face of the membrane filter 205 in a direction that is substantially parallel to or approaching nearly parallel to the front face of the membrane filter, creating the desired shearing action.

Empirical study has revealed that for a linear conical surface 41S, the area of the outlet O preferably should be less than or equal to the maximum area of the inlet I. That is, $R_1 H_1 \geq R_2 H_2$. For example, the exemplary manifold can have the following dimensions (all units here in mm): $R_1 = 1.24$, $H_1 = 1.32$, $R_2 = 10.00$, $H_2 = G = 0.15$. The maximum inlet area would thus be $3.27\pi$ mm$^2$ and the outlet area $3.00\pi$ mm$^2$, which is slightly less than the maximum inlet area, but greater than the average inlet area, which can be defined as 50% of the maximum inlet area ($1.64\pi$ mm$^2$). Thus, the outlet area can fall between the maximum inlet area and the average inlet area. Another example can have the following dimensions (all units here in inches): $R_1 = 0.040$, $H_1 = 0.060$, $R_2 = 0.400$, $H_2 = 0.006$. The maximum inlet area would thus be $0.0048\pi$ in$^2$, which is equal to the outlet area.

In summary, the manifold chamber M that confronts the substantially flat membrane filter should have a shallow, funnel-shaped configuration and a peripheral outlet so as to create a substantial radial flow across the outer surface of the membrane filter. The radial flow creates a shearing action that washes or flushes away any particulates that are relatively weakly attached so as to leave a very thin layer of particulates—a monolayer—on the surface of the membrane filter.

LBP Device and Method

FIGS. 11-57 illustrate a preferred embodiment of an LBP device according to the present invention. The LBP device is an automated machine for preparing slides for viewing, imaging or optical analysis. The LBP device can use the above-described dual flow filtering system (FIGS. 6, 7a, 9) to collect monolayers or thin layers of cells and transfer them onto slides.

Figure 11:
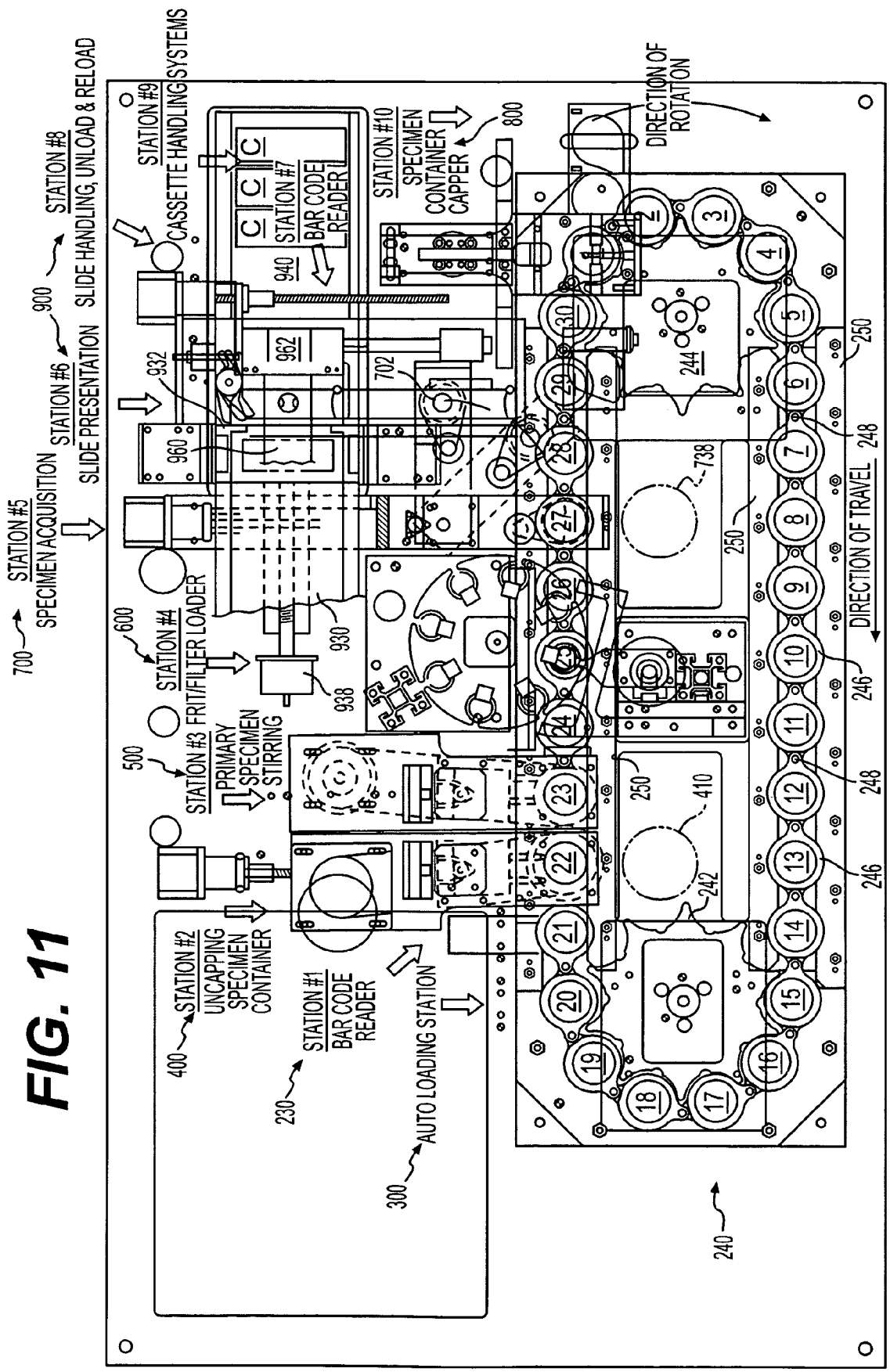
FIG. 11 is a top plan view of the LBP device.
Figure 11A:
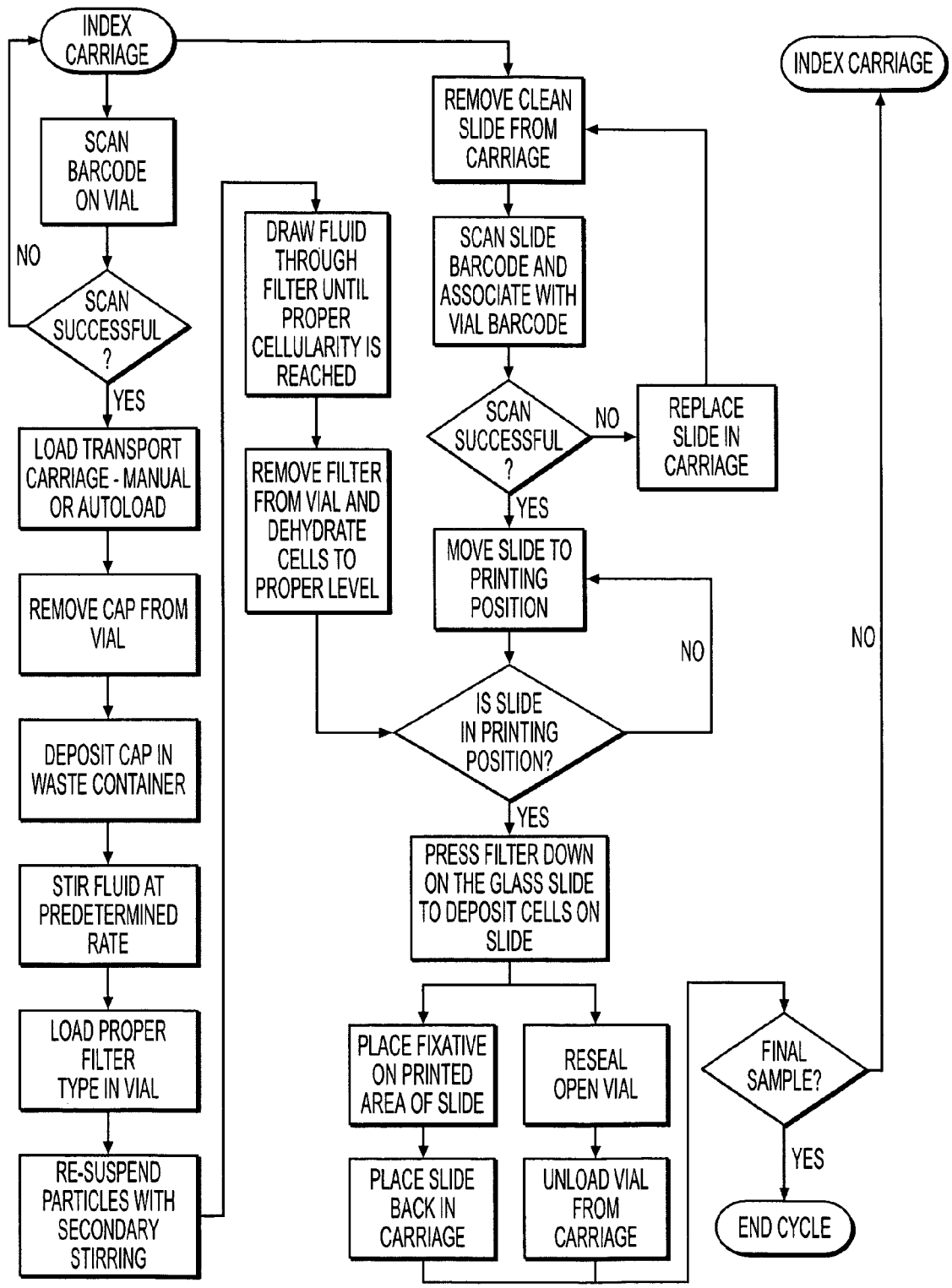
FIG. 11a is a schematic diagram of the operating sequence of the LBP device.

Referring to FIG. 11, the illustrated embodiment of the LBP device can be compartmentalized into at least six discrete processing stations: data acquisition station (bar code reader) 230; uncapping station 400; primary stirring station 500; filter placement station 600; specimen acquisition station 700; and re-capping station 800. These six stations are structured for parallel processing, meaning that all these stations can operate simultaneously and independently of the other. The LBP device also includes a separate data reading station, a slide presentation station, a slide handling station, and a cassette handling station, all of which can be incorporated as an integrated system 900. The LBP device further includes a transport mechanism 240 for moving the specimen containers to the various operating stations. It can further incorporate an auto loading mechanism 300 that automatically loads and unloads specimen vials onto and from the transport mechanism. All stations are computer-controlled. FIG. 11a shows the operating sequence of the LBP device. This is the top-level table from which the operating software is structured.

Figure 12:
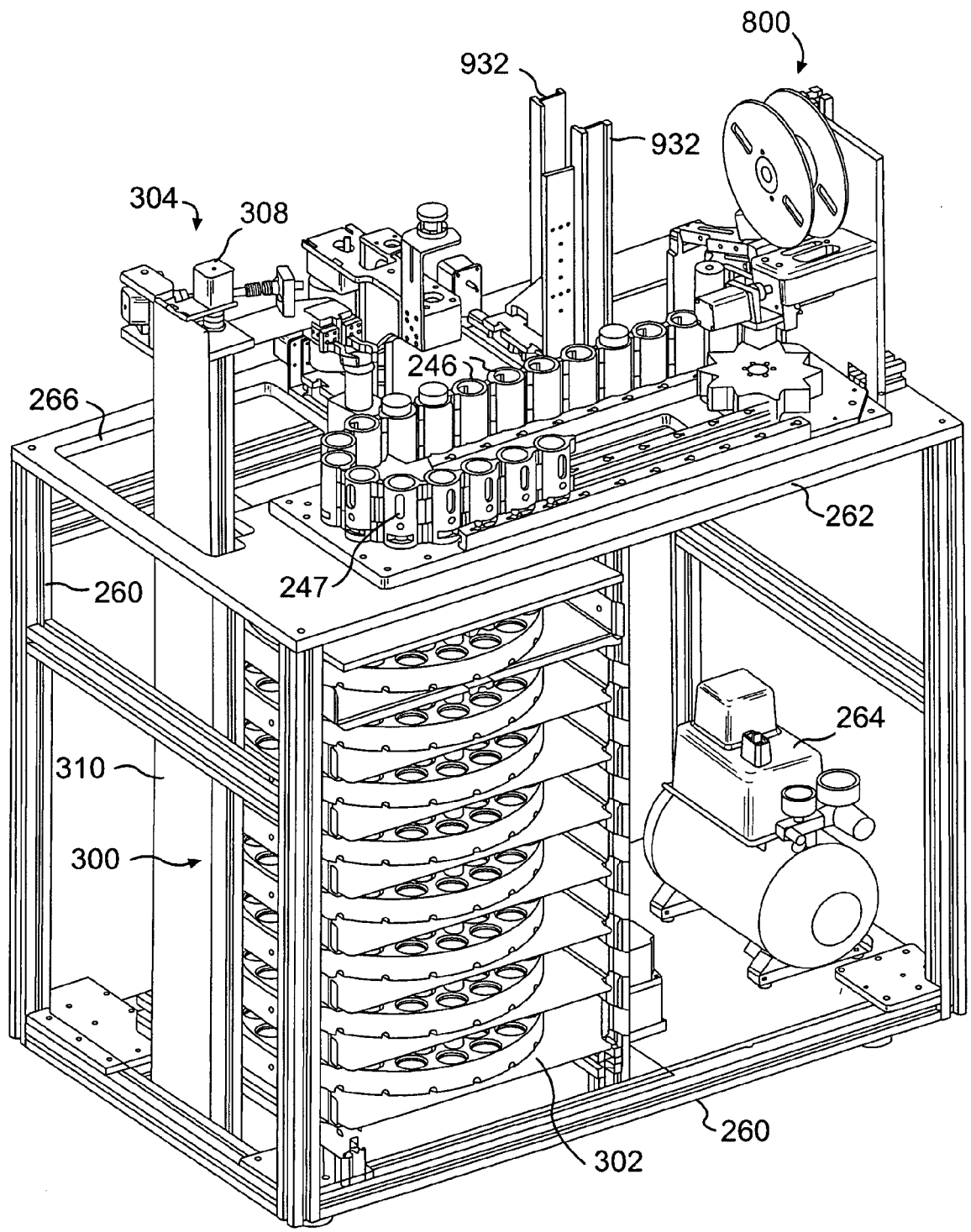
FIG. 12 is a front perspective view of the LBP device, with certain parts removed for clarity.

FIG. 12 shows the basic structural elements of the LBP device, namely a frame 260 preferably made of extruded aluminum, preferably on casters (not shown) for mobility, and a machined aluminum base plate 262 supported by the frame and on which the main operating mechanisms are mounted. Beneath the base plate is a compressor 264 for supplying compressed air for powering some of the components; a vacuum pump (not shown) which provides a vacuum source for various components; stainless steel shelves for holding the vial trays used in the auto loading mechanism 300; and electrical components, including power supplies and controllers, and miscellaneous equipment. A compressor would not be required if electrically-powered actuators were used instead of air-powered actuators. A user interface, e.g. a touch-sensitive LCD display (not shown), is mounted to the left of the transport mechanism 240 and gives the technician control over machine operation beyond the normal automated processing protocols. See FIG. 25, which shows examples of a log-in screen (top) and a navigation screen (bottom) as they might appear on the user interface. Of course, other screens would be presented to the user as he/she interacts with the user interface.

An "economy" version of the LBP device can take the form of a counter-top model for processing a more limited number of specimens at a time. In such a model certain components can be eliminated, such as frame 260 and auto loading mechanism 300, while other components can be scaled back, such as the capacity of filter placement station 600. External sources of vacuum and compressed air could be used to power such a device, while other components (power supplies, controllers, etc.) could be repositioned to one or more modules adjacent to or on a modified machine base plate. Various ways of implementing these modifications will be readily apparent to those skilled in the art.

Transport Mechanism

Referring to FIG. 11, the transport mechanism 240 comprises an endless link-belt conveyor 242 driven by a stepper motor (not shown) around precision sprockets 242, 244. The conveyor has a plurality of receptacles or carriers 246, linked by pins 248, for receiving a corresponding number of specimen vials. The illustrated embodiment in FIG. 11 has 30 receptacles, numbered 1 through 30. Depending on the sample vial size and the length of the conveyor, the LBP device can use fewer than or greater than 30 receptacles, as desired or feasible, sufficiently long to permit all processing to be completed in a single line.

The receptacles 246 of the link-belt conveyor are guided between the sprockets by pairs of guide rails 250 forming tracks, and has a conventional position correction system (not shown) to accurately position the receptacles. The LBP device can track the position of each receptacle and step-drive or index them in a conventional manner. For instance, the LBP device can include linear position sensors, such as optical sensors or a photo-interrupter on each link, that can feed the position to a controller for registering carrier position and precisely indexing each carrier at each of the processing stations along the processing path. The manner of driving the conveyor for precise alignment and positioning is conventional and thus will not be described further.

The guide rails 250 that form tracks in Z and Y axes engage slots machined in the sides of the receptacles. See, for example, FIGS. 29, 33, 37 and 43. The mechanical tracks and drive sprockets can be constructed of a self-lubricating plastic for operation without the need to add an external lubricant. The receptacles 246 each can have a window 247 (see FIG. 12) for allowing access to laser or optical scanning of the bar code on the specimen containers. The conveyor can be hard-coated aluminum, 7-impregnated with PTFE7 for easy cleaning. The link pins 248 can be precision ground and hardened. The link pins can be axially fixed in location in the non-rotating link bore. Rotating link bores can be fitted with a suitable bearing material capable of operation without additional lubricant. For operator safety, the conveyor operation can be interlocked with the cover of the machine (not shown).

The receptacles 246 are also configured so that they receive or seat the specimen vials in a particular orientation. That is, the specimen vials and the receptacles are complementarily configured or keyed so that the vials can only be seated in the receptacles in a particular orientation. For example, the vials can be "D" shaped, namely having a flat side (see FIGS. 2a, 2b), and the receptacles can be "D" shaped so that the flat sides align with each other. In this way the vials do not rotate relative to the receptacles, while allowing unrestricted vertical movement relative to the receptacles. In addition to the D shape, each vial can have a bottom notch 25 (see FIG. 2a), and the receptacles can have a mating peg or stud (not shown) that keys into the notch 25. While the illustrated notch and peg are arcuate, they can take on other mating shapes (e.g., V-shaped).

Vial Loading/Unloading Mechanism

Figure 13:
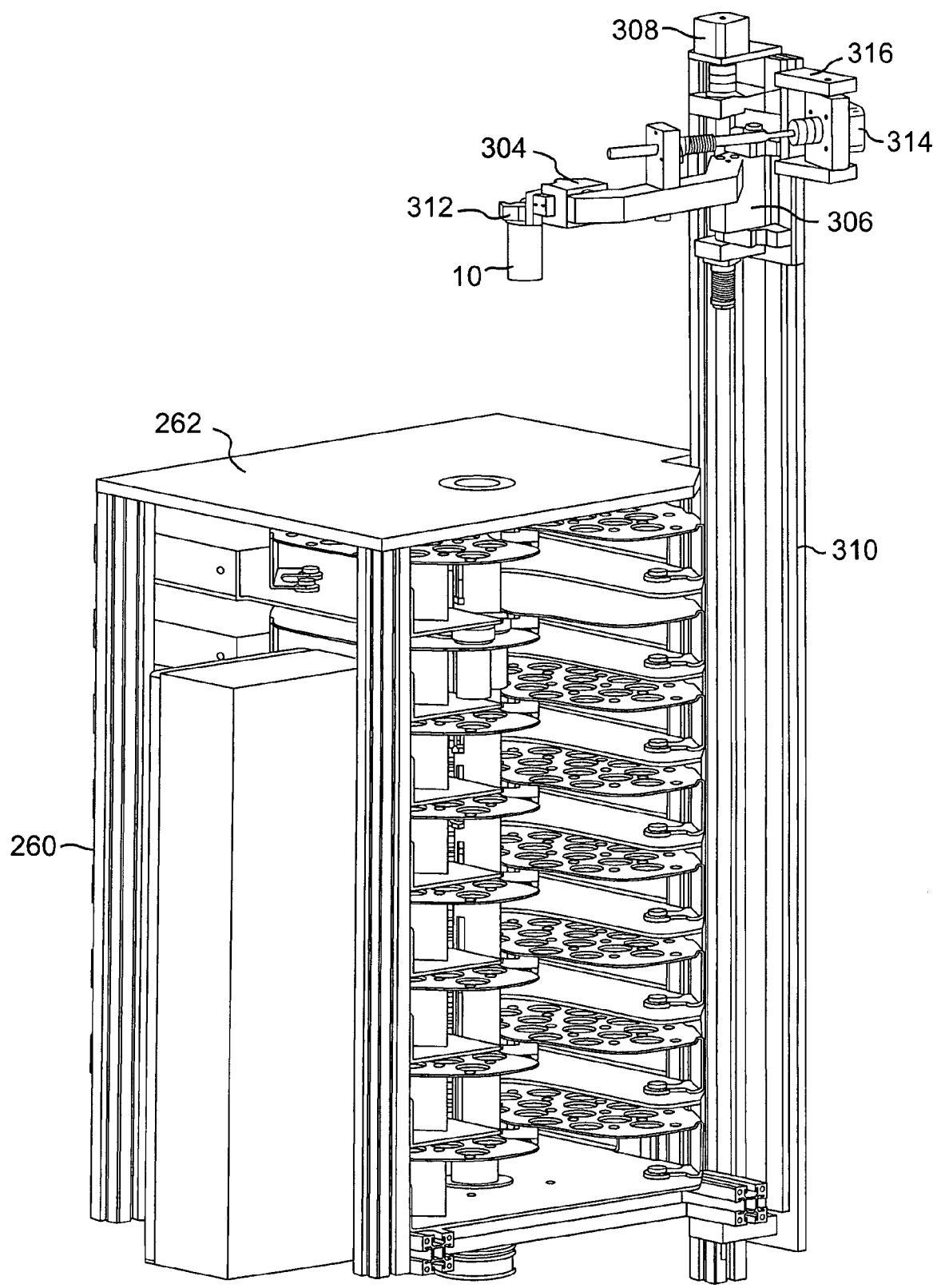
FIG. 13 is a rear perspective view of a portion of the LBP device, showing the auto loader/unloader mechanism.
Figure 14:
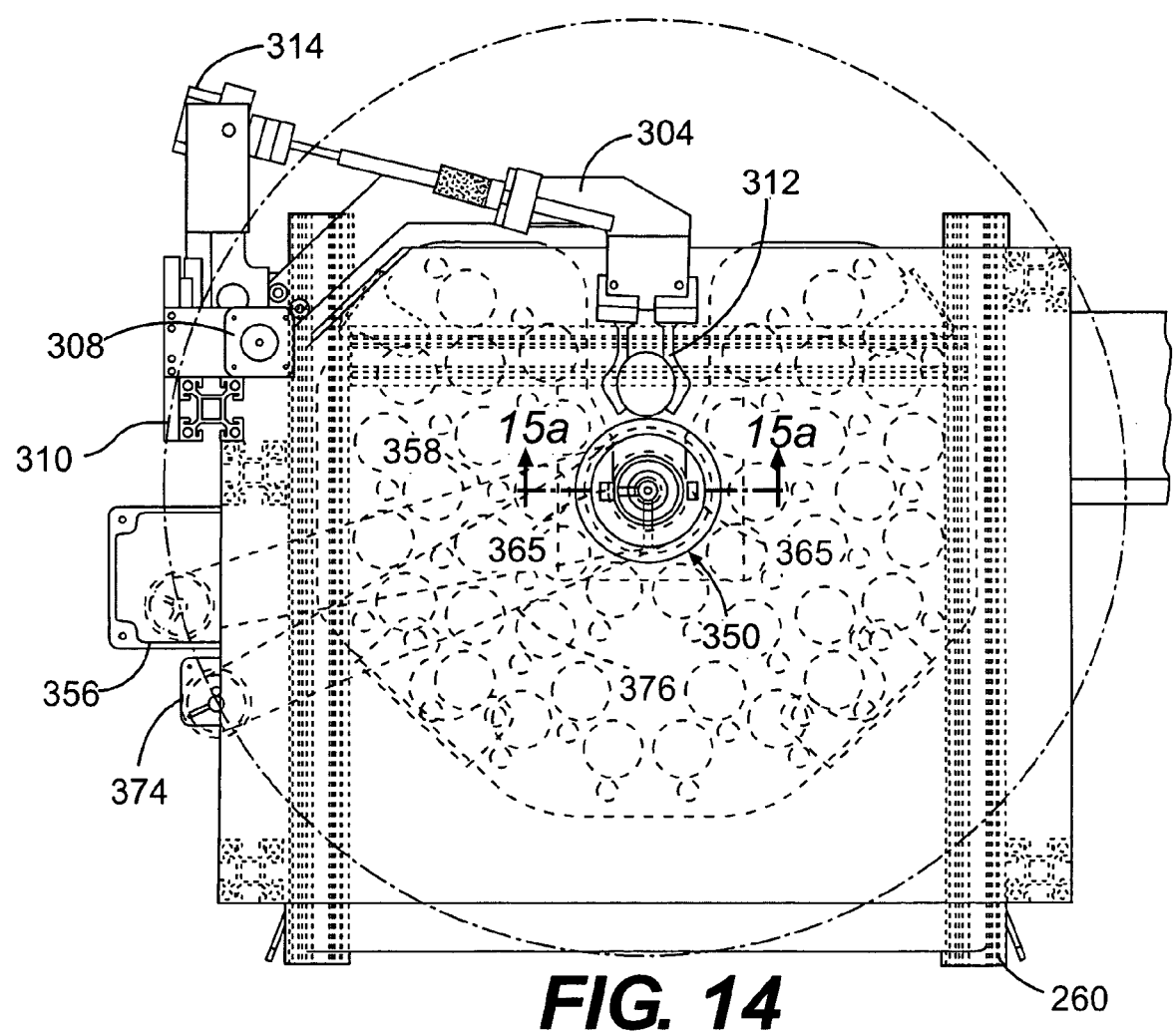
FIG. 14 is a top plan view of the auto loader/unloader mechanism.
Figure 15:
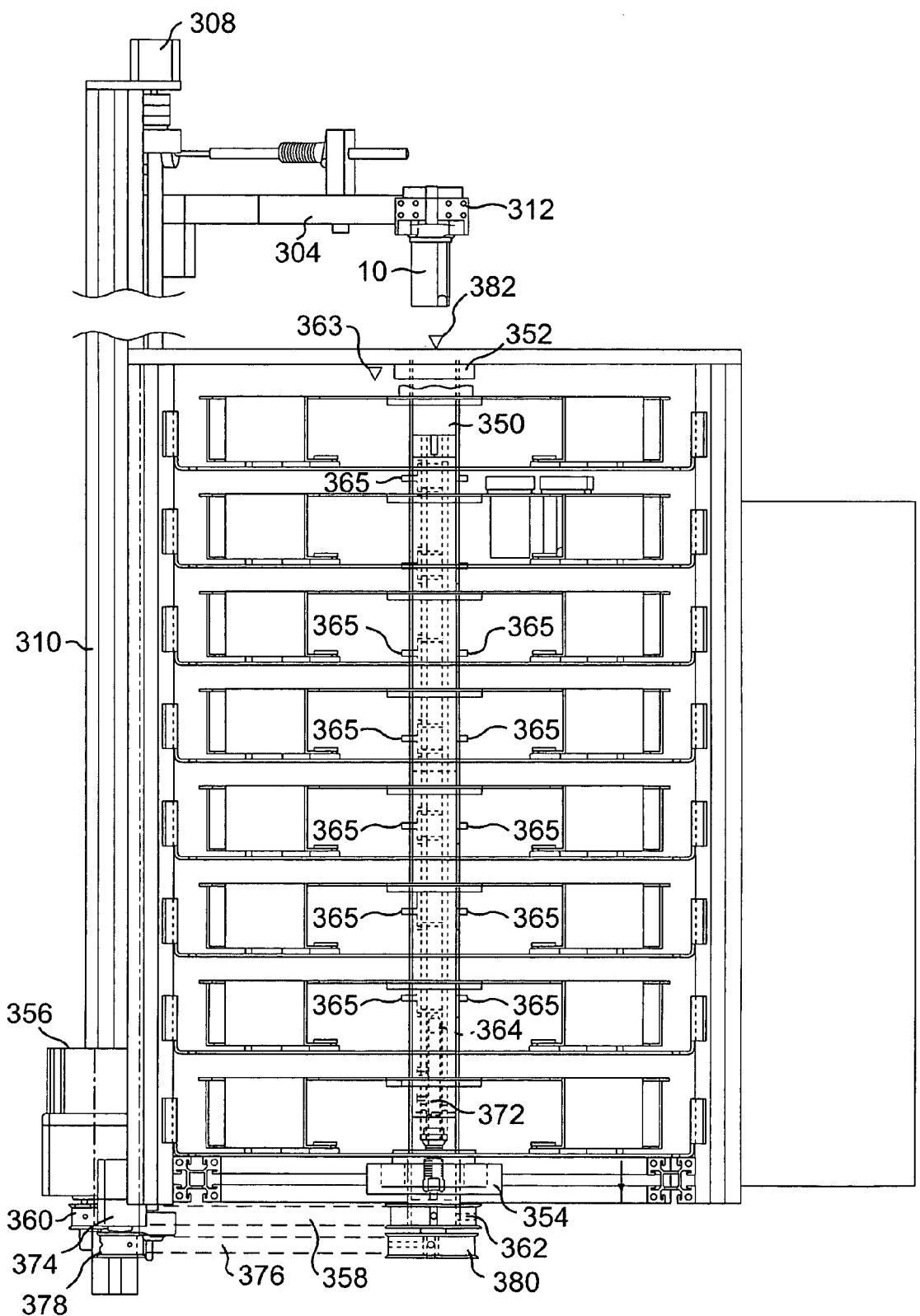
FIG. 15 is a front elevational view of the auto loader/unloader mechanism.

FIGS. 12, 13 and 14 show the automated vial loading and unloading mechanism 300. A pivoted pick-and-place arm 304 is mounted on an elevator carriage 306 driven by a vertical (Y-axis) lead screw motor 308 atop a vertical standard 310. Arm 304 has a conventional electrically- or pneumatically-operated jaw-type gripper 312 adapted to grasp and move specimen vials 10 in three degrees of freedom. Arm motion in horizontal planes is afforded by lateral lead screw motor 314, which is pivotally mounted in a clevis-type bracket 316 to elevator carriage 306. Instead of a jaw-type gripper as shown, the pick-and-place arm can be equipped with a conventional pneumatically operated suction-head type gripper as shown in FIG. 15. Such a gripper has a silicone rubber bellows 318 which seals against the cover 30 of a vial when placed against the cover and subject to suction through a suction line 320. Whether mechanical or pneumatic, actuation of the gripper is accomplished through the programmed operation of the machine as is understood by those skilled in the art.

Referring to FIGS. 17-20, specimen vials 10 are stored in special injection molded plastic vial trays 330 that slide into the machine on shelves 320 (see FIG. 12). To avoid confusion, it should be pointed out that FIGS. 13-15 show a different form of tray (made of stamped steel), but the operation of the mechanism that rotates the trays, regardless of their construction, is the same. The plastic vial trays 330 are the preferred form, and are preferably made of polypropylene. The term "tray" as used herein is not limited to the embodiments shown, and should be construed to cover any type of carrier, rimmed or rimless, that can support and move a generally planar array of discrete articles generally in the manner described herein.

Each tray 330 has forty-one circular recesses 332 sized and configured to receive specimen vials 10 only in one orientation. The upper edge of each recess 332 preferably has a beveled edge 333, which facilitates smooth insertion of vials. The recesses are arranged in a close-pack array of four concentric rows, preferably as follows. The outermost row has sixteen recesses; the next row in has eight recesses; the third row in has nine recesses; and the innermost row has eight recesses. The receptacles of adjacent rows are offset for closer spacing. The receptacles of the second row are radially aligned with the receptacles of the fourth (innermost) row. The receptacles of the outermost row are spaced at 18° on center. The receptacles of each of the other rows are spaced at 36° on center. Of course, other receptacle arrays could be used as long as they permit access of all vials by the pick-and-place arm 304. Each receptacle has a unique and addressable location, so that any vial can be accessed at will and in any sequence.

As noted above, orientation of specimen vials during the processing is critical, so the proper orientation of the stored vials in these trays ensures that the pick-and-place arm 304 will properly position each vial in a conveyor receptacle 246. Accordingly, each recess 332 has at its bottom (see FIG. 19) a fixed indexing peg 334 that is sized to fit into notch 25 in the vial. The pegs 334 are installed, e.g., by adhesive, in grooves 335 that are molded into the tray adjacent the bottoms of the recesses 332. Some of the pegs have been omitted from FIG. 19 for illustrative purposes.

The pegs 334 are arranged at specific angles with respect to the median plane of the tray 330 such that each vial removed from the tray is delivered to a transport receptacle with its notch aligned with the mating peg in that receptacle, and vice versa. Each of these angles is dictated by the rotational position of the tray 330 when a vial in a specific recess 332 is to be accessed by the pick-and-place arm 304, and the angular rotation of the pick-and-place arm from the point of vial pick-up to the point of vial placement in the conveyor receptacle 246. The determination of these angles is considered to be within the abilities of one of ordinary skill in the art.

The tray 330 also has three upstanding guide posts 336, each with a spring-loaded ball 338 at its tip, which cooperate with guides (not shown) above each shelf 302 and serve to guide the tray into the machine as it is inserted and ensure its proper orientation. The guide posts 336 also serve as stacking posts when the trays are stacked for storage (see FIG. 20), the balls 338 engaging dimples 339 (see FIG. 19) in the bottom of the superior tray.

The tray 330 also has a large flared notch 340 which is oriented toward the machine when the tray is inserted on a shelf 302. The innermost portion of the notch 340 has opposed keyways 342 which are adapted for engagement by floating keys, as described below. The keyways preferably are formed in a milled brass hub insert 343 that is recessed flush with the top of the tray and secured thereto by screws.

Figure 15A:
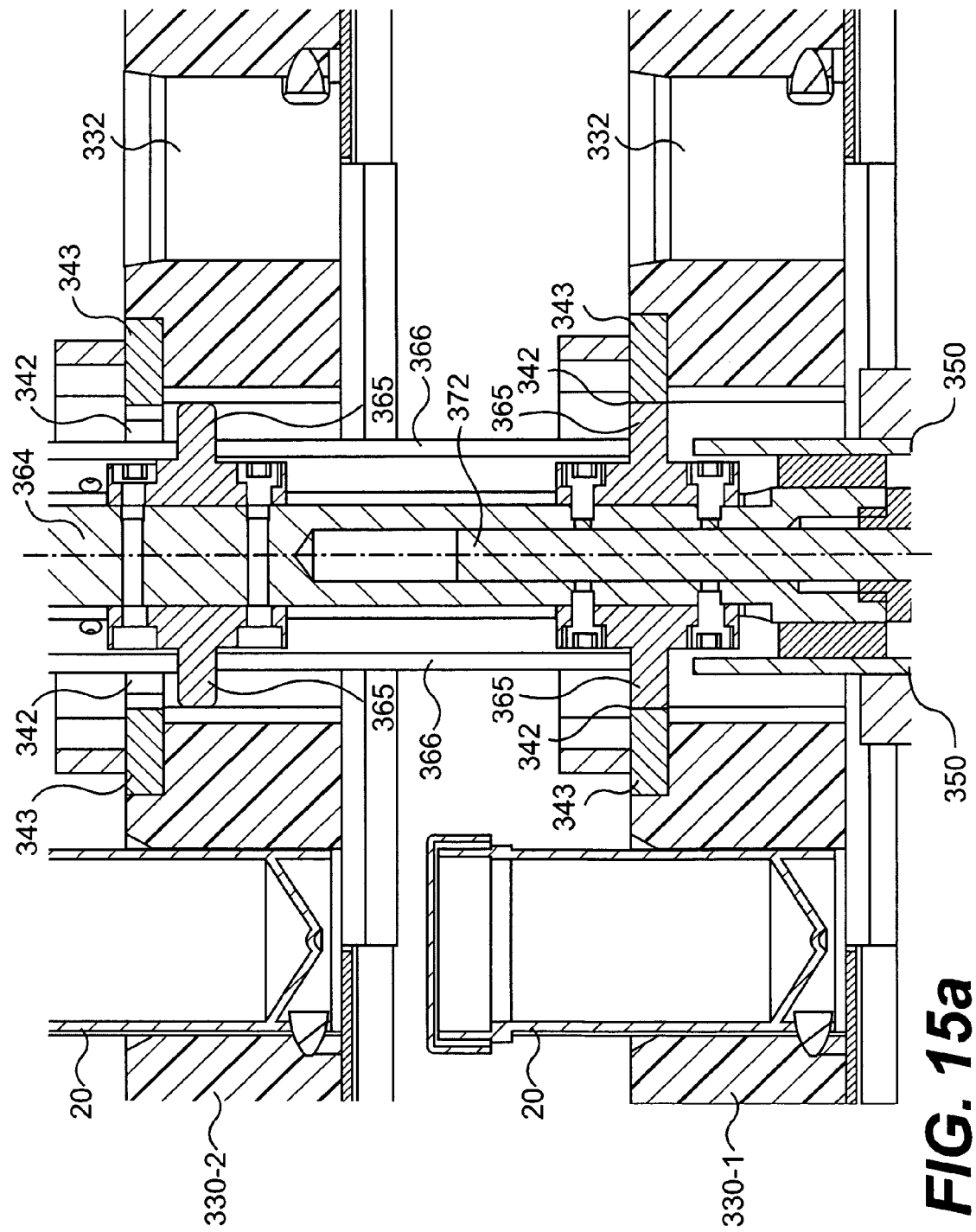
FIG. 15a is a detail sectional view taken along line 15a-15a in FIG. 14.
Figure 19:
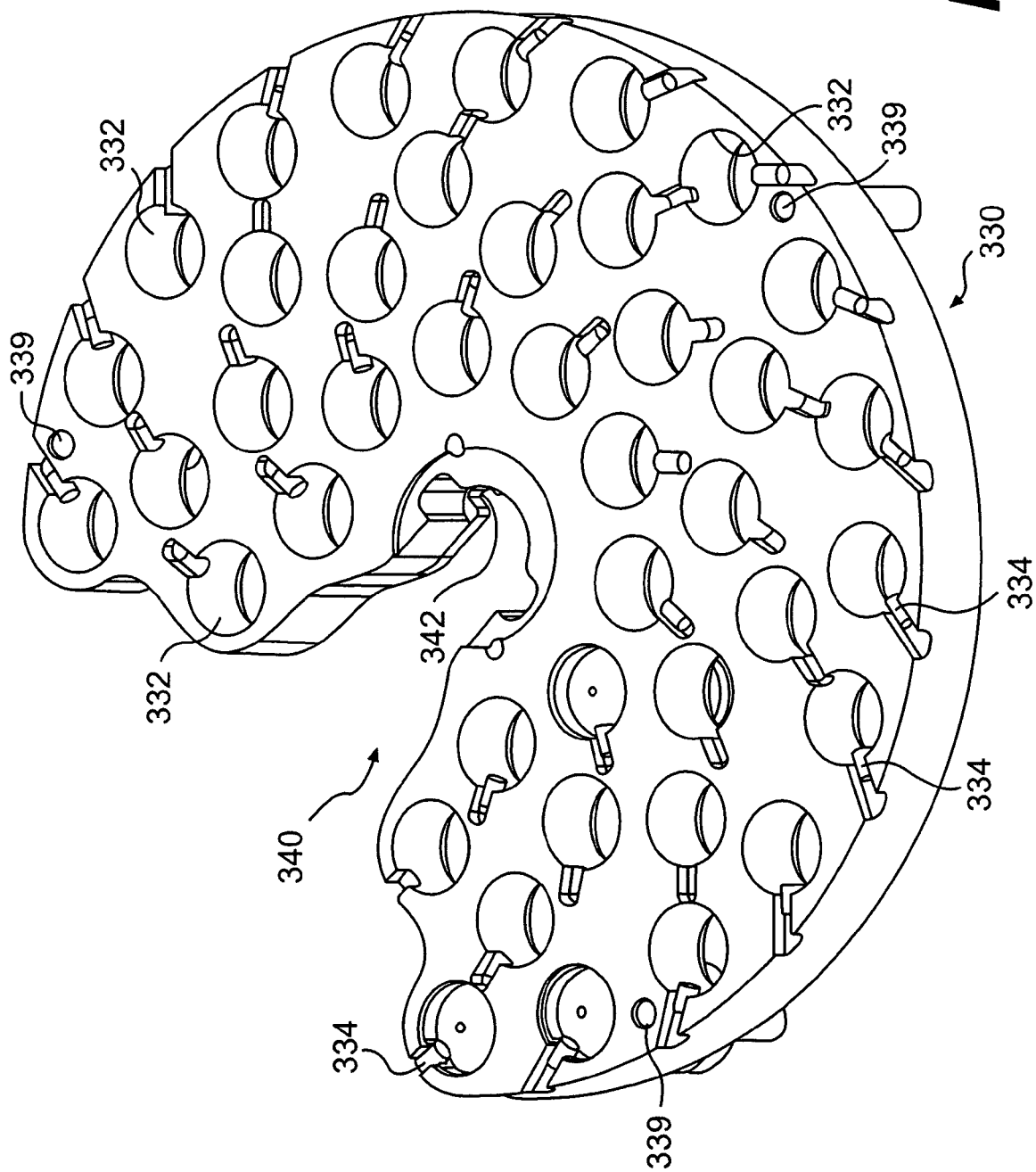
FIG. 19 is a bottom perspective view of the specimen vial tray of FIG. 17.
Figure 20:
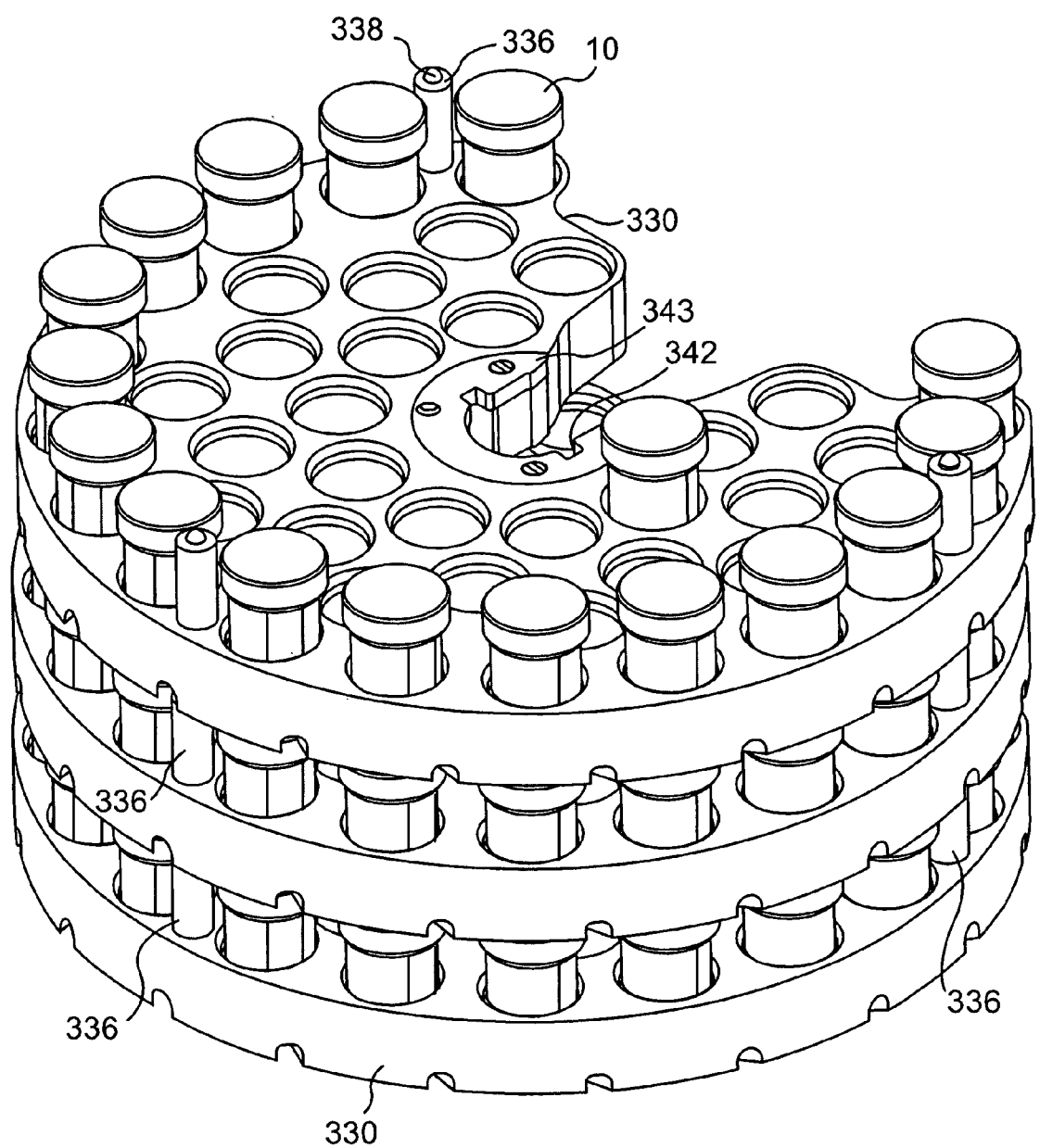
FIG. 20 is a perspective view of three stacked specimen vial trays.

Referring to FIGS. 14, 15 and 15a, a rotary outer spindle 350 is journaled at its top and its bottom in bearings 352, 354, respectively. Outer spindle 350 engages and rotates only one tray at a time so that the pick-and-place arm 304 can access vials therefrom by moving downwardly through an opening 266 in base plate 262 and past any idle trays via their homed notches 340. FIG. 14 shows the home positions of the trays in dashed lines, with their notches 340 aligned and embracing outer spindle 350. Spindle 350 is rotated in a precision manner from the bottom by a computer-controlled rotation stepper motor 356 and a timing belt 358 engaging timing gears 360, 362. A downwardly facing optical rotary position sensor 363 located over the aligned tray notches detects when and how far a tray is rotated from its home position and provides control feedback for rotation of stepper motor 356.

Within outer spindle 350 is an inner spindle 364 carrying eight pairs of opposed keys 365, one pair for each tray. The keys 365 project from outer spindle 350 through opposed slots 366 in the outer spindle (see FIG. 15a, which is a sectional view through the spindles and the center portions of the bottom two trays). The inner spindle 364 is moved vertically within the outer spindle 350 by an internal lead screw 372. Lead screw 372 is rotated by lead screw stepper motor 374 through a timing belt 376 and timing gears 378, 380. A key "home" sensor 382 (see FIG. 15) is located at the top of inner spindle 364 to provide a reference point, i.e., when the machine is turned on, it will "home" the inner spindle to the key home sensor 382 and then reference its movements from there.

The even vertical spacing of the pairs of keys can be seen in FIG. 15. This spacing, or pitch, differs from the pitch of the keyways 342 in a full complement of installed trays 330. Accordingly, which keyways are engaged by the keys depends on the vertical position of inner spindle, and only one pair of keyways (tray) can be engaged at any time. The enlarged view of FIG. 15a shows that the keyways 342 of bottom tray 330-1 are engaged by keys 365, while the keyways of the tray above it, 330-2, are not engaged by any keys. Movement of inner spindle 364 by one-eighth the pitch difference disengages one tray and engages the immediately adjacent tray. The operation of the loading and unloading mechanism is unaffected by the absence of one or more trays from the tray slots, which are defined by shelves 302.

When a selected tray is to be accessed by the pick-and-place arm 304 (as determined by the computer controller), the lead screw motor 374 moves the inner spindle the appropriate distance so that the appropriate keys engage the keyways of the selected tray. The rotation motor 356 then rotates the keyed tray to the proper angular position so the arm 304 can access a particular recess 332. The superposed arrangement of the trays, the way in which a selected tray is accessed by the gripper 312 through the flared notches 340 of superior trays, and the close-pack spacing of the recesses 332 in each tray make for an extremely compact, high capacity and efficient vial handling system that is readily incorporated into the compact base of the LBP device.

In the embodiment shown, the LBP device can accommodate up to eight trays holding forty-one specimen vials each. One of the forty-one recesses can be reserved for a cleaning vial, which would contain a cleaning solution and be run through the LBP device to clean the various parts of the device that normally come into contact with specimen fluid. Alternatively, the forty-first vial could contain a typical control specimen for calibration purposes. Thus the LBP device can accommodate up to at least 320 vials containing specimens to be processed. The device is therefore capable of operating continuously unattended for a long duration—at least eight hours—so that specimen processing can be carried out even when laboratory personnel are not normally present, such as at night.

When the trays 330 are bar-coded or otherwise labeled with machine-readable identifying data, they can be used in an automated storage device that can access a particular tray on command. The tray-identifying data can be input into the integrated data management system so that the location of any specimen vial in tray storage can be readily ascertained.

A cost reduction in tray-based storage of specimen vials can be achieved by using a liner-type system in conjunction with trays 330. For example, vials can be supported and stored in thin sheet-like liners (not shown) that conform to trays 330 and slip readily into recesses 332. The liners are stiff enough to be self-supporting when fully loaded, can be stacked, and can be housed in wheeled carts for ease of mobility.

Data Accessioning and Specimen Management

Figure 21:
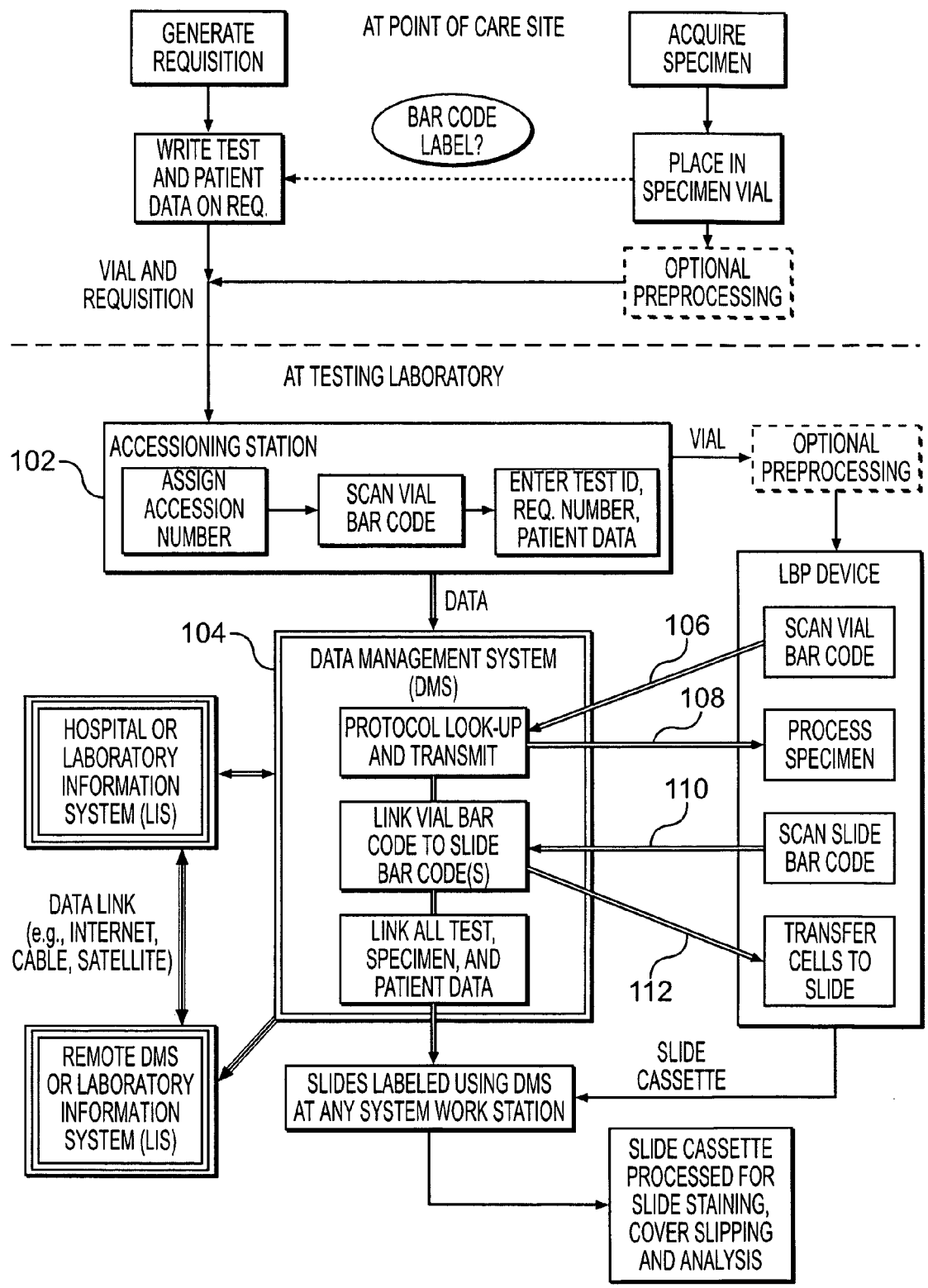
FIG. 21 is a block diagram showing specimen vial handling and data flow.

It is, of course, important to keep track of each specimen vial and the specimen slides produced from each vial. Accordingly, the LBP device typically communicates with the integrated data management system (DMS) 104 through an accessioning station 102 or other computer. FIG. 21 schematically illustrates specimen vial handling and the flow of data that is integrated into to operation of the LBP device. The communication link between the LBP device and the DMS can be made via ethernet or other protocol using a direct peer-to-peer connection, or through a server-based network.

The specimen processing operation begins with collecting or transferring data from the labeled specimen vial, e.g. via a bar code reader on a data entry terminal or accessioning station, to the DMS via either a direct connection or over a network. Specimen tracking data can include, for example, the patient's name, test identification (ID) number, patient data, and any special processing instructions. For example, the bar-coded specimen vial can be linked to the patient information initially by a paper requisition form and subsequently by an assigned, unique numerical ID in the database. In a preferred embodiment, the patient and test information including the vial bar code can be entered into the networked DMS database at the point-of-care site (e.g., physician's office), thereby eliminating entirely the need for a paper requisition form. U.S. Pat. No. 5,963,368 (incorporated herein by reference), which is assigned to AccuMed International, Inc. (now Molecular Diagnostics, Inc., or MDI) discloses a similar concept as applied to a computer-controlled instrument for analyzing biological specimens (a microscope) and storing data from each analysis. The '368 patent is exclusively licensed to MonoGen, Inc. (the owner of this application) in the field of liquid-based cytology in combination with or for use with non-fluorescence based image analysis devices, processes, systems and/or instruments. MonoGen's commercially available pathology work station and data management system implement the concept disclosed in the '368 patent.

Figure 21A:
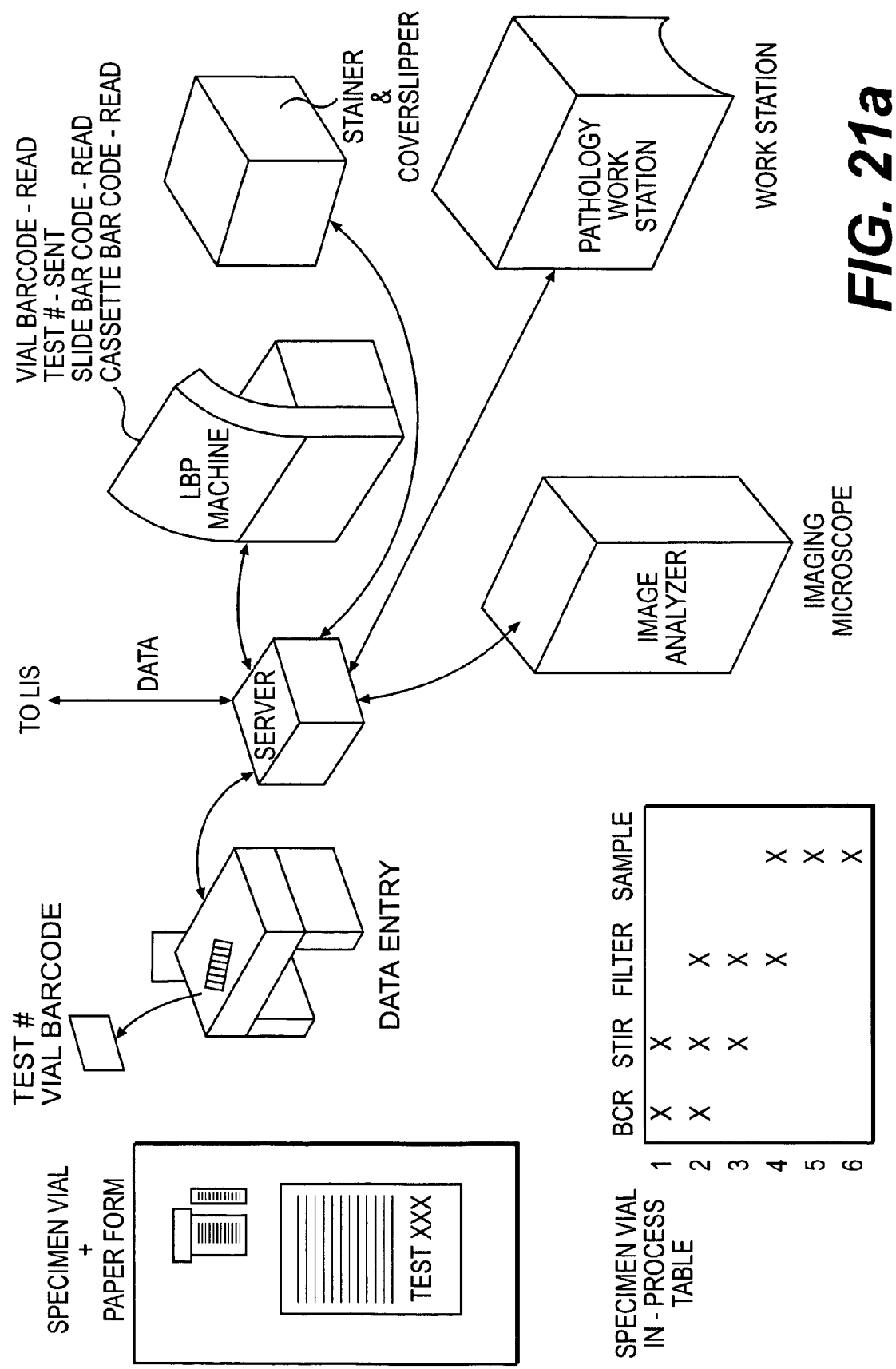
FIG. 21a is a pictorial diagram showing an overall laboratory system incorporating the LBP device.

Each specimen vial includes an identification (ID) symbol or label (e.g., bar code) and/or a stored information label or symbol such as a hologram or a memory chip or device. The present embodiment contemplates reading an ID label using an optical reader, such as a bar code reader, which provides the information to a DMS for sharing information between different work stations or instruments at the same or different locations, such as laboratories, doctors' offices, hospitals, or other patient care providers. FIG. 21a depicts an overall laboratory system wherein the DMS is expanded to link specimen/patient data through a server to a variety of specimen processing devices and/or computerized work stations for fully integrated specimen management.

A separate bar code reader 230 (see FIG. 11) is mounted on the LBP machine itself, and scans all specimen vials prior to processing through a slit in each transport receptacle 246. Each of the transport receptacles 246 is tracked using this symbol or code, such as a bar code that can be read with a conventional optical reading device. The bar code readers used in the LBP device can be any commercially available type, such as Keyence BL-600, with a minimum BCR target code capability of Interleaved 2 of 5, Code 128c, or EAN-128. The bar code readers preferably are sealed in liquid-tight enclosures for operator protection. After reading, specimen vial/transport receptacle ID data are transmitted to the DMS of the host database or work station. The host database or local work station can then transmit back to the LBP device the specific processing protocol to be performed on that individual specimen.

Some of the most important functions of the data management system (DMS) include:

Obtaining data on the patient and the specimen during accessioning, and making this available to each instrument as required to set processing parameters and to provide medical data to the slide reviewer;

Maintaining chain of custody of specimens and slides to ensure data integrity; Compiling data and printing required forms for regulatory, compliance, and laboratory management reports;

Generating medical reports and ensuring integrity using safeguarded digital electronic signatures;

Managing billing for instruments on "per use" charges;

Storing optimal processing protocols for each process and supplying to the instrument in accordance with the specimen type and/or user requirements; and Facilitating remote diagnostics and repair, and providing user manuals and troubleshooting guides.

Figure 21B:
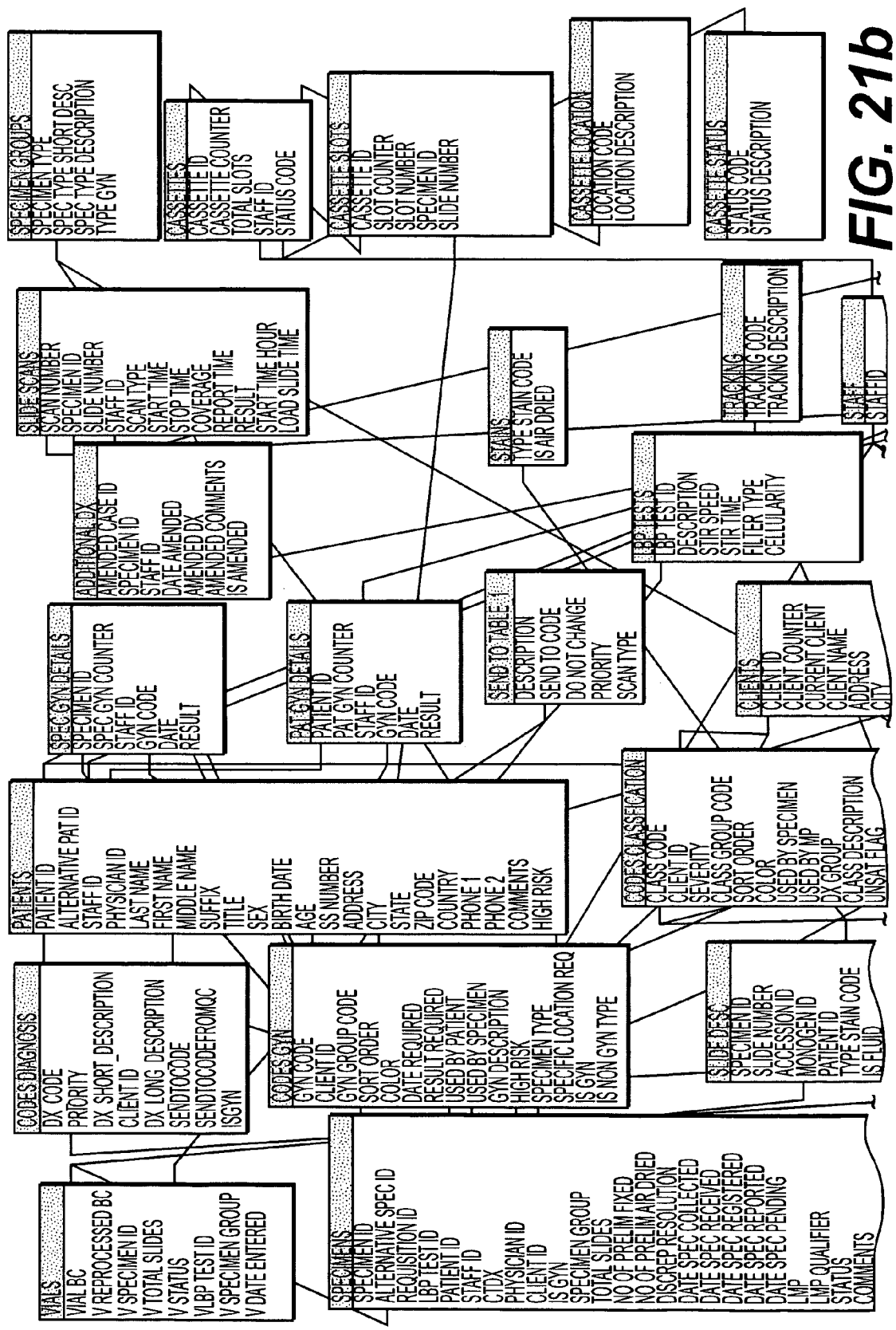
FIG. 21b is a relational database table.
Figure 21B:
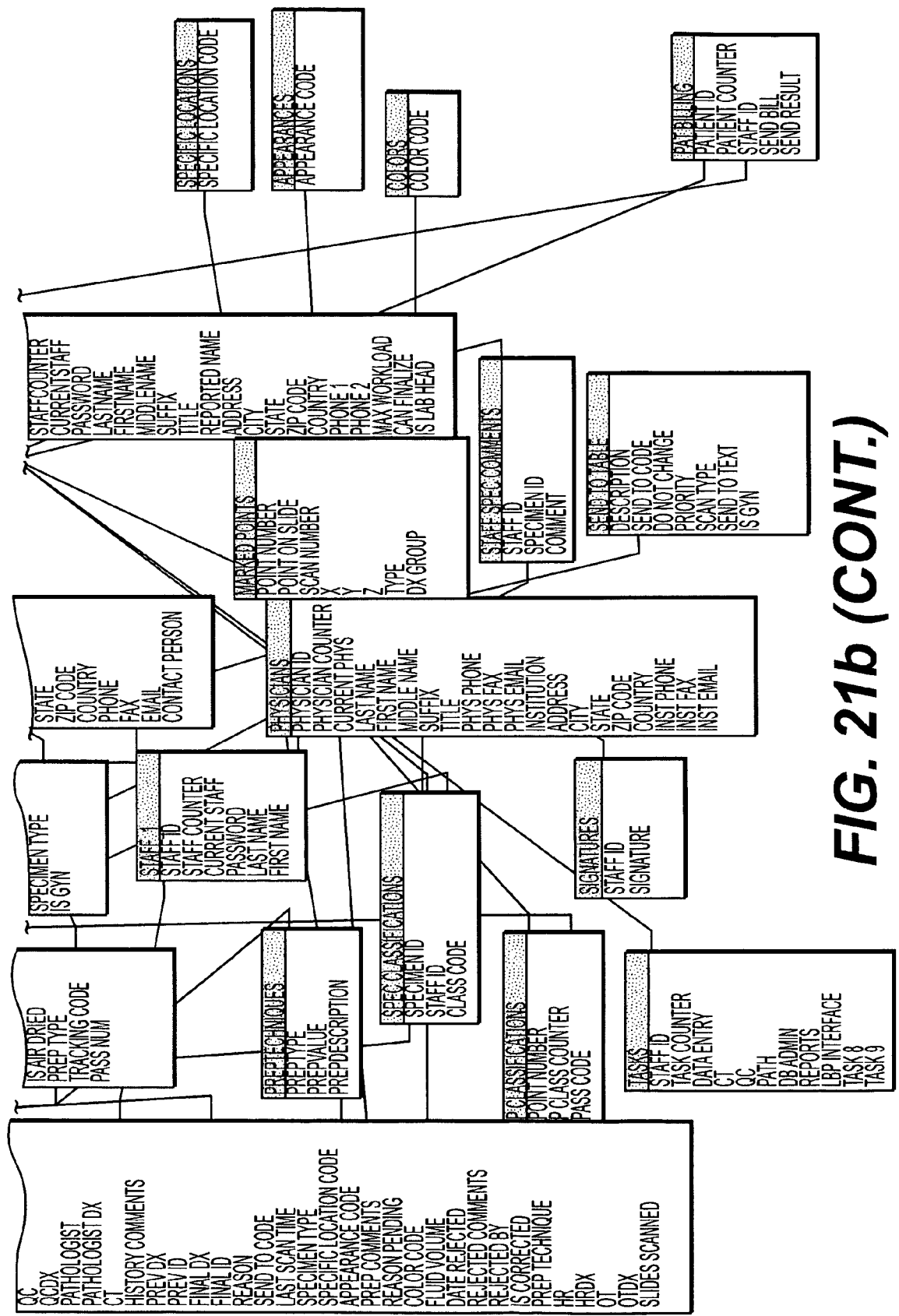

FIG. 21b shows an example of a relational database table that can be used to accomplish these tasks.

The DMS can provide paper-free data flow among the different stages of the cytology process, saving a significant amount of personnel time and cost, reducing transcription errors, improving accuracy, and eliminating the space required to store paper records. By automating and managing data acquisition, storage and retrieval, each operation becomes more efficient, significantly reducing the turnaround time for specimens. Specimen quality is enhanced by automated calibration and cross-checking routines that identify potential problems early. Flexible foreign language support for worldwide sales assists laboratories in multicultural environments.

The DMS provides a common user interface that provides detailed information on the operation of each connected laboratory device and work station, and together with online user manuals and training aids eases use and minimizes training. The DMS handles the exchange of all relevant patient and specimen data with the users' own LIS (or other data management systems) through a provided software interface. Moreover, remote instrument diagnostic capabilities ensure maximum interruption-free operation. The reduction in paperwork, ready cross-compatibility with other instruments and existing computer networks, and integration with the central hospital or laboratory information system provides significant user benefits.

Figure 23:
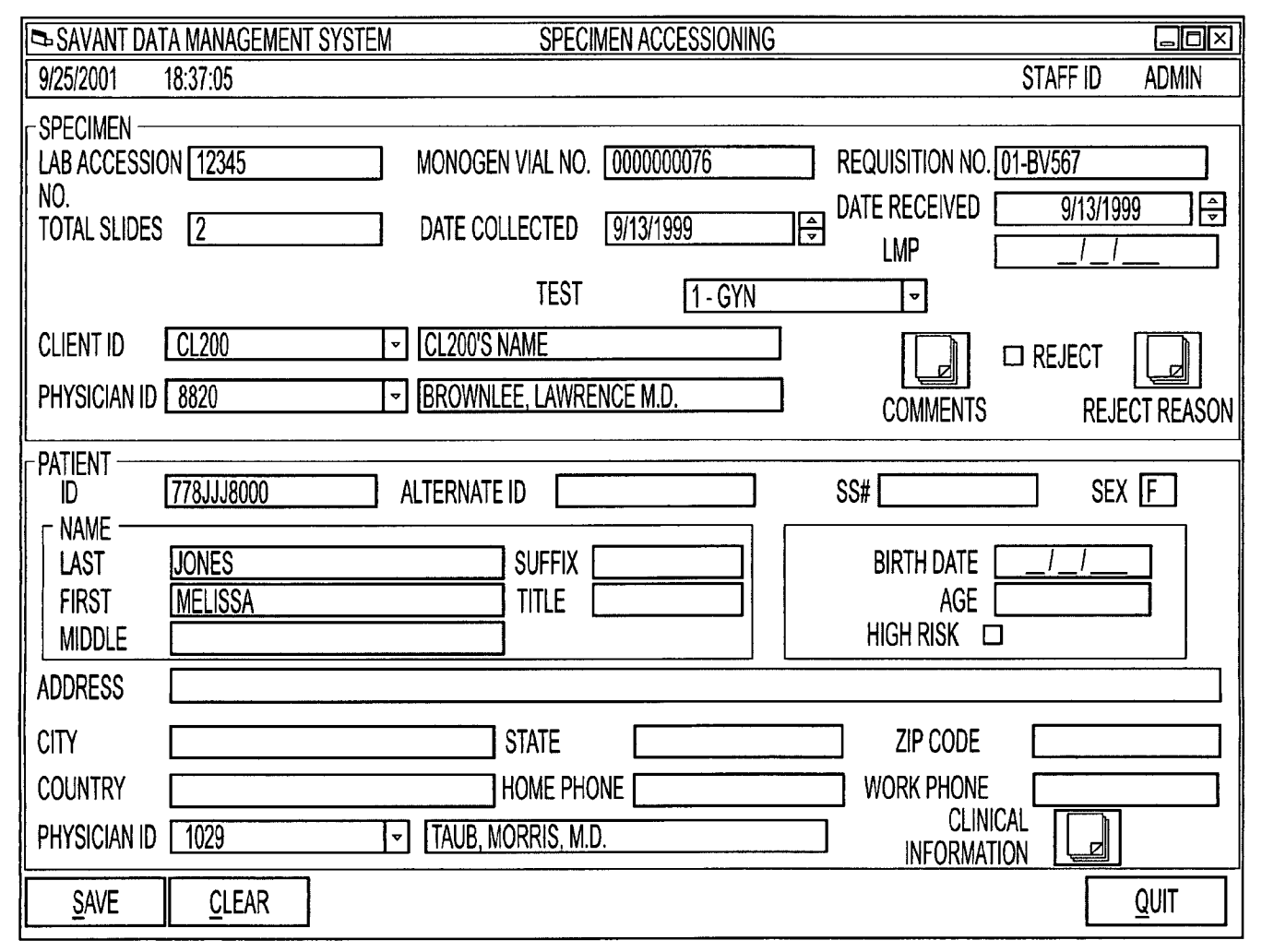
Figure 24:
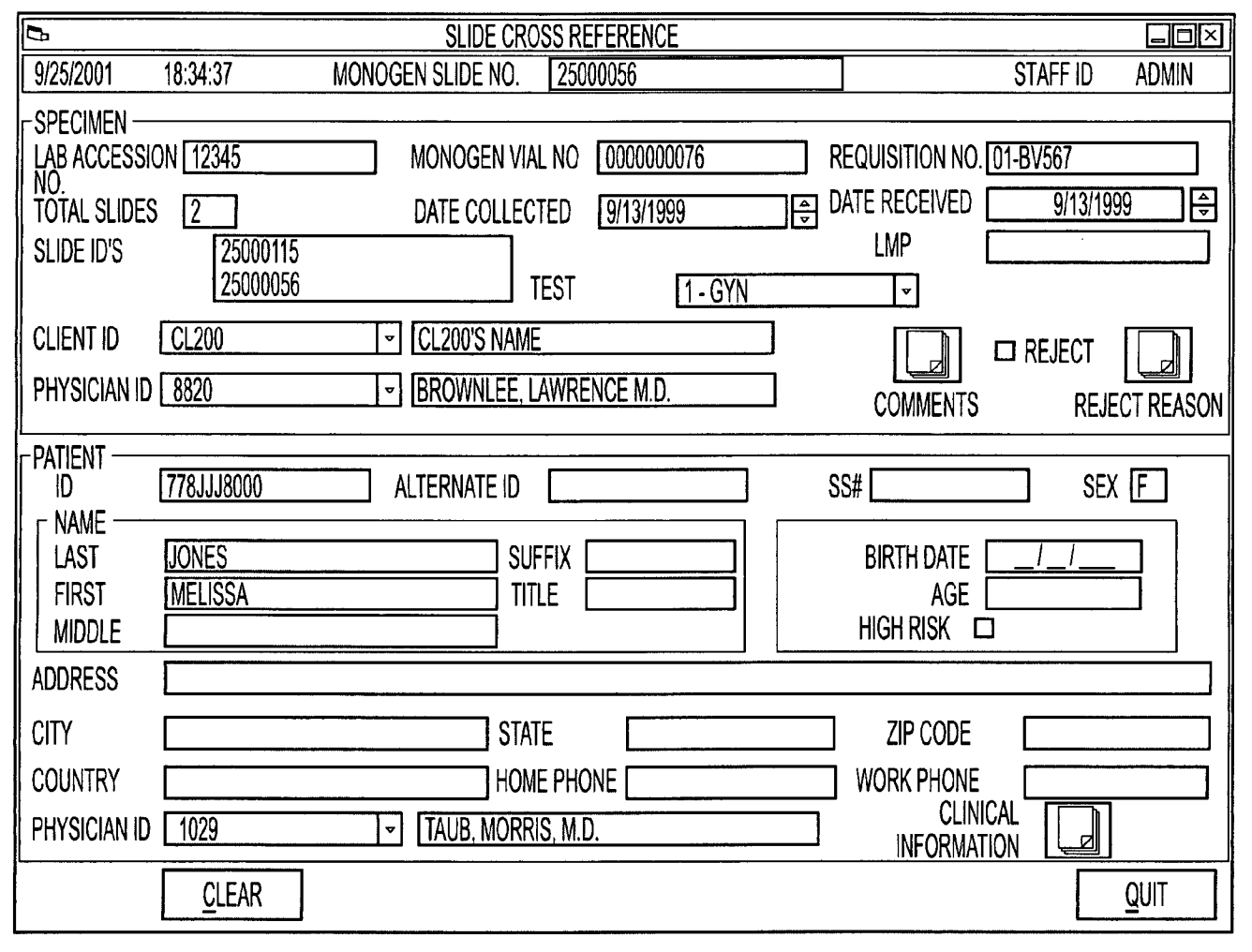

In typical operation, the laboratory: (1) receives a requisition from the healthcare provider along with the pre-bar-coded specimen vial, (2) assigns a unique ID number (accession number) to the specimen, and (3) based on information on the requisition, enters a specific LBP test ID to specify the process to be used. FIG. 23 shows an example of the accessioning (data entry) screen that is presented to the technician, into which the vial bar code, accession number and LBP process code are entered. When the specimen vial is loaded into the LBP device for processing, the LBP device automatically reads the bar code on the specimen vial and transmits the bar code number (106) to the DMS, which sends back the processing parameters for the selected test, and the number of slides to be produced. The LBP device returns an acknowledgment (108) and processes the specimen, making one or more slides as instructed via the DMS. Immediately before the LBP device imprints a specimen slide with material filtered from a specimen vial, the LBP device reads the bar code from the pre-bar-coded slide that is to receive the specimen sample. The LBP device sends each slide bar code (110) and its associated vial bar code to the DMS which updates the patient database with the slide bar code number, cross-references it to the correct vial number, and signals (112) the LBP device to proceed. The LBP device then imprints a cytological sample from the specimen onto one or more slides and readies the onboard data log for the next specimen to be processed. FIG. 24 shows an example of a DMS menu screen showing data items that are now linked in the DMS database, including the vial number, slide number(s) and patient data. The DMS can produce a printable report listing slide ID numbers and associated vial ID numbers, patient data and processing protocols.

At a minimum the protocol variables include specimen mixing parameters (stirring speed and time) and filter selection. Typically, primary stirring speed can be varied from 500 rpm to 3,000 rpm selectable in 50 rpm steps. The stirring interval can be varied from 5 to 120 seconds, selectable in 5 second increments. Choice of filter type is based on average pore size diameter: either 5 micron (red housing), e.g. for non-gynecological specimens, such as sputum specimens, or 8 micron (white housing), e.g. for gynecological specimens, depending on the test protocol selected.

The LBP device is capable of processing mixed sample-runs (i.e., runs that may include vials containing various types of specimens) interchangeably and without the need for batch processing of same-type specimens. Specimen processing can include at least 100 different processing protocols resident within the DMS and accessible to users.

Predefined procedure codes (test ID's) such as the following can be used to simplify operator input and specify which processing protocol is used:
1 breast cyst, L
2 breast cyst, R
3 bronchial brushing
4 bronchial washing
5 bronchoalveolar lavage
6 cerebrospinal fluid
7 colonic brushing/wash
8 esophageal brushing/wash
9 gastric brushing/wash
10 gingival (buccal) scrape
11 gyn PAP test
12 intestinal brushing/wash
13 nipple discharge, L
14 nipple discharge, R
15 ovarian cyst, L
16 ovarian cyst, R
17 pericardial effusion
18 peritoneal effusion
19 pleural effusion
20 rectal brushing/wash
21 sputum, induced
22 sputum, spontaneous
23 urine, catheterized
24 urine, voided Each specimen is processed with a new filter to prevent the possibility of cross contamination. In the present embodiment, either of two or more different filter types can be specified for versatility in test selection (the device's eight filter tubes allow for up to eight different filter types). Processing parameters for each type of specimen preparation can be determined remotely and in advance, and communicated to the processing device using a bi-directional communication link utilizing the specimen vial bar code as the key identifier. The LBP device can utilize default (pre-loaded into the DMS) process protocols as well as laboratory-generated process protocols that users can add to the DMS.

An overfilled-vial sensor (not shown) can be positioned at or just downstream of the bar code reader 230 to detect whether an excessive amount of fluid is present in each translucent vial. Opening and processing an overfilled vial can result in hazardous spillage or ejection of biological fluid. Accordingly, if an overfilled vial is detected, the DMS will be so notified and the complete LBP processing protocol for that vial will be canceled, allowing the overfilled vial to proceed through the processing path unopened. Alternatively, an overfilled condition can be sensed at the conveyor holder 246 into which vials are loaded by the vial loading mechanism 300. If an overfilled vial is detected there, the DMS will be so notified and the loading mechanism will be instructed immediately to return the overfilled vial to its tray 330.

A similar approach can be used to deal with other anomalies detected as each vial is loaded into the conveyor. For example, a sensor (not shown) can be used to detect an unreadable bar code on the vial, or detect when a vial is improperly position in the holder 246. When any such condition is detected, the DMS will be so notified and the loading mechanism will be instructed immediately to return the overfilled vial to its tray 330.

Figure 22:
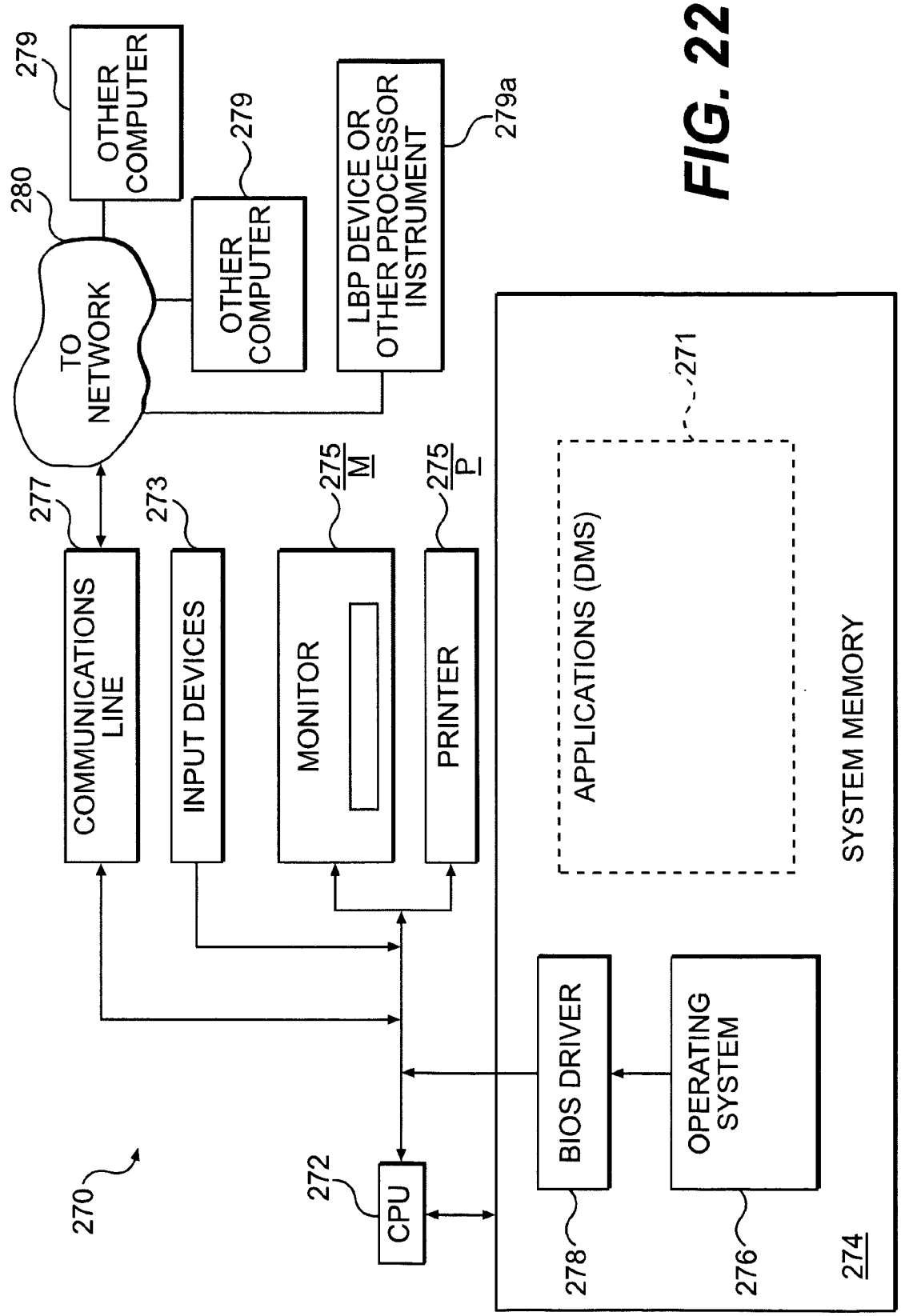
FIG. 22 is a block diagram showing a computer or work station.
Figure 26:
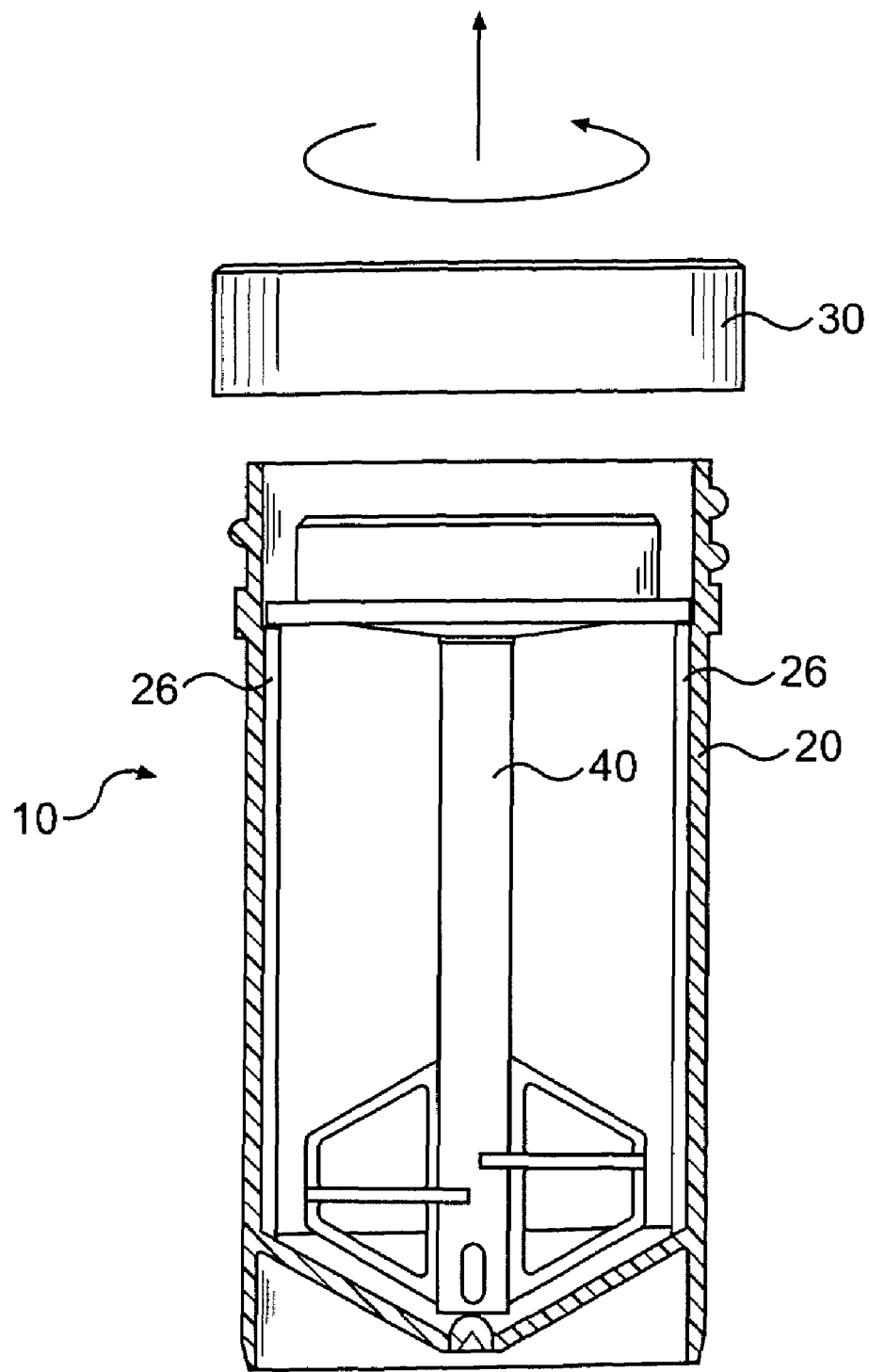
FIG. 26 is a vertical sectional view of a specimen vial being uncapped.
Figure 27:
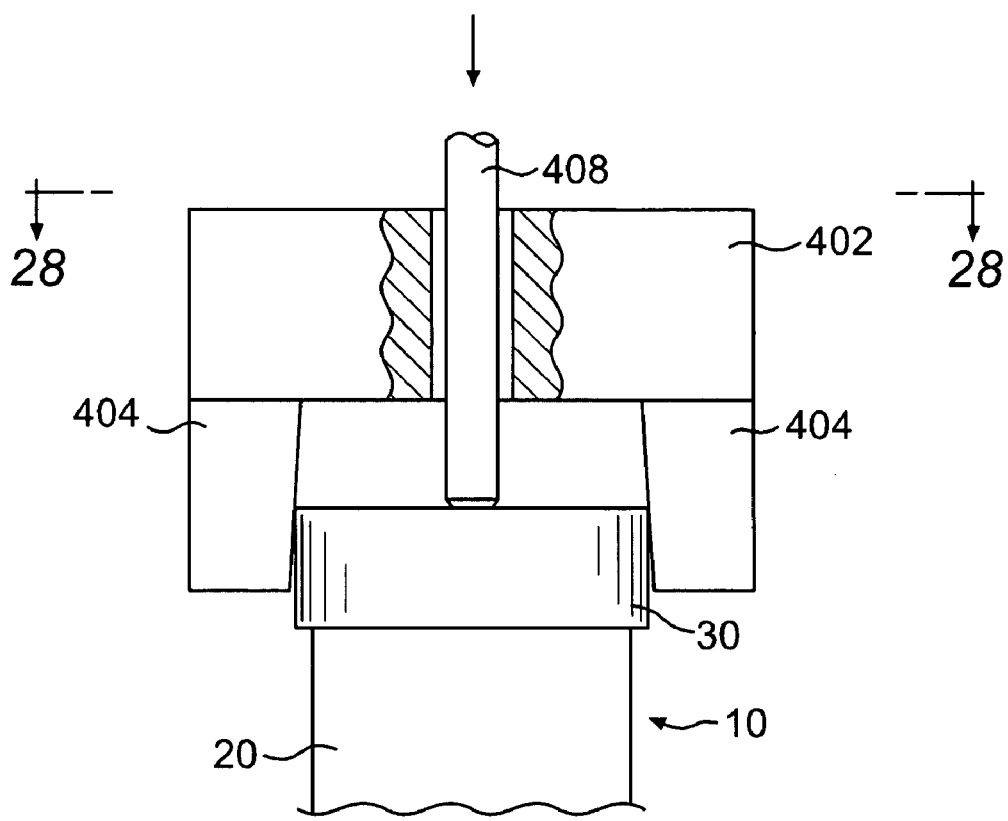
FIG. 27 is a front elevational view, partly in section, of a specimen vial engaged by the uncapping head of the LBP device.
Figure 28:
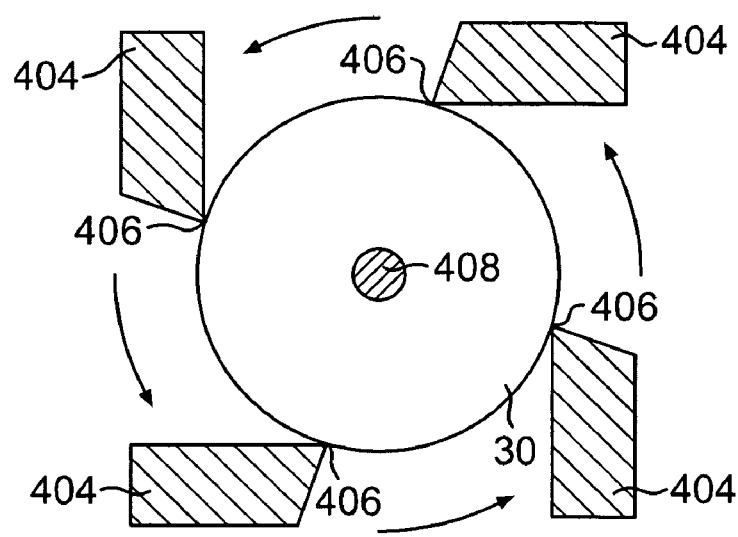
FIG. 28 is a top plan view of the uncapping head, taken along line 28-28 in FIG. 27.
Figure 29:
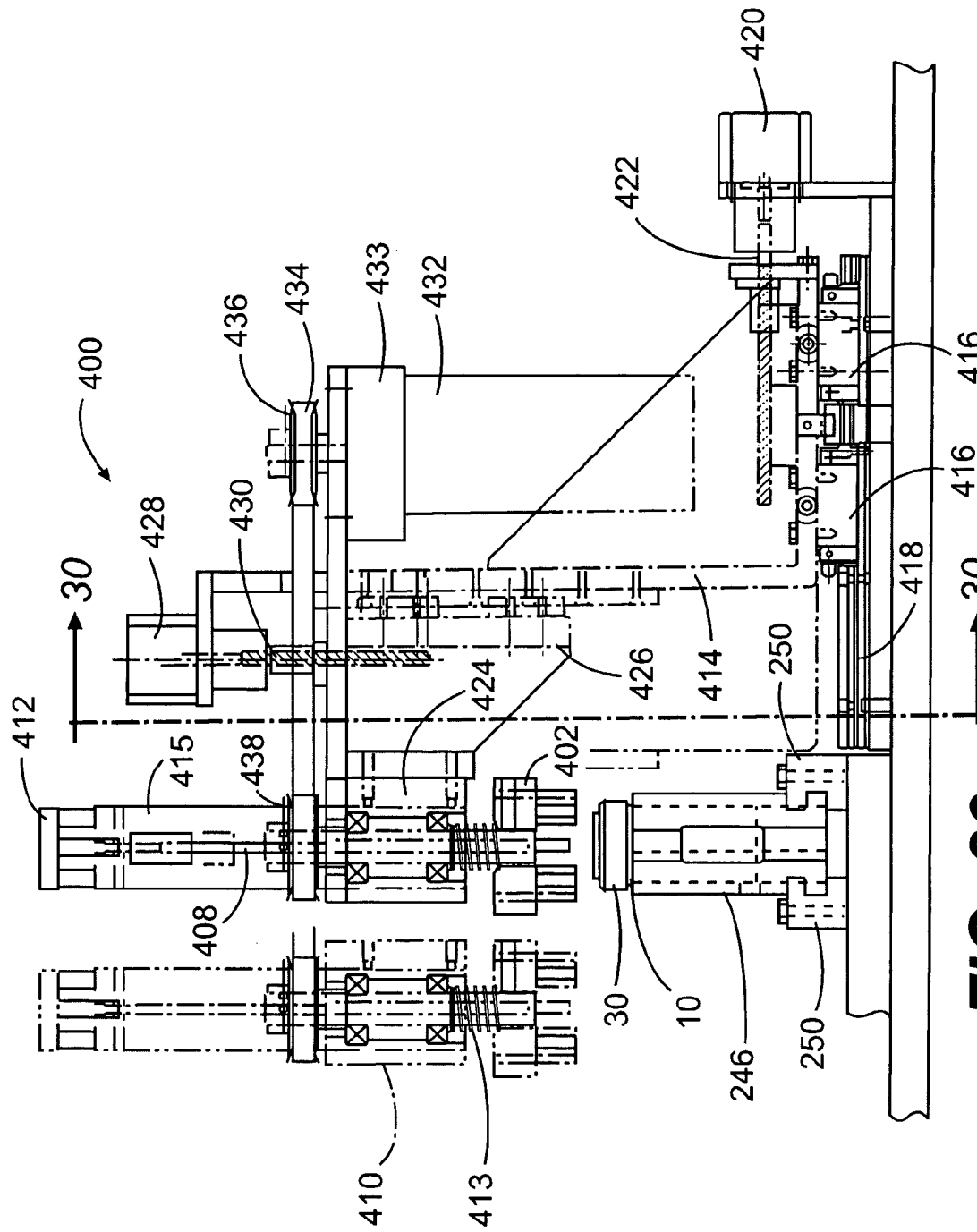
FIG. 29 is a side elevational view of the uncapping station of the LBP device.
Figure 31:
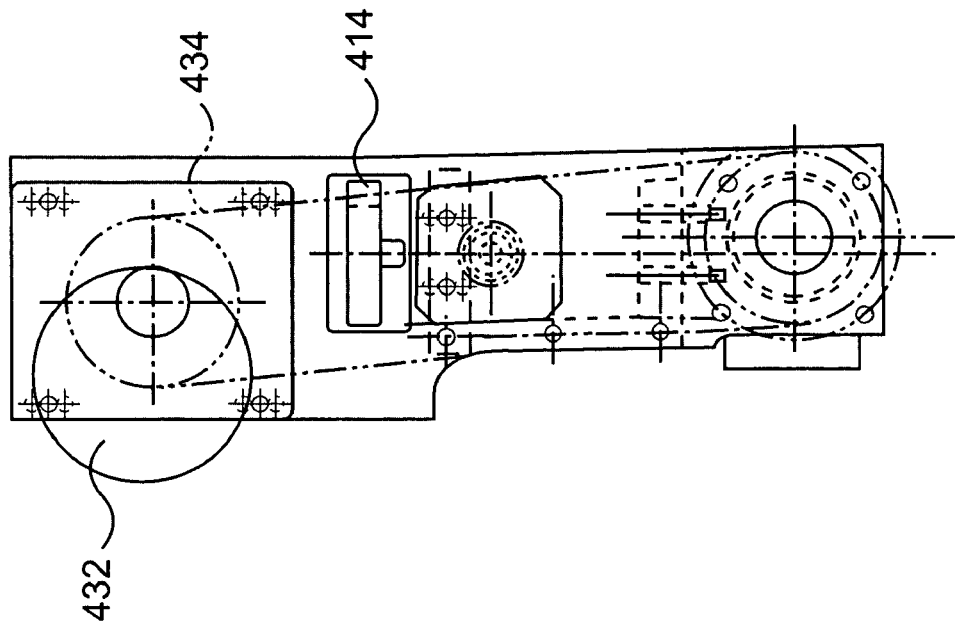
FIG. 31 is a top plan view of the uncapping station of FIG. 29.
Figure 30:
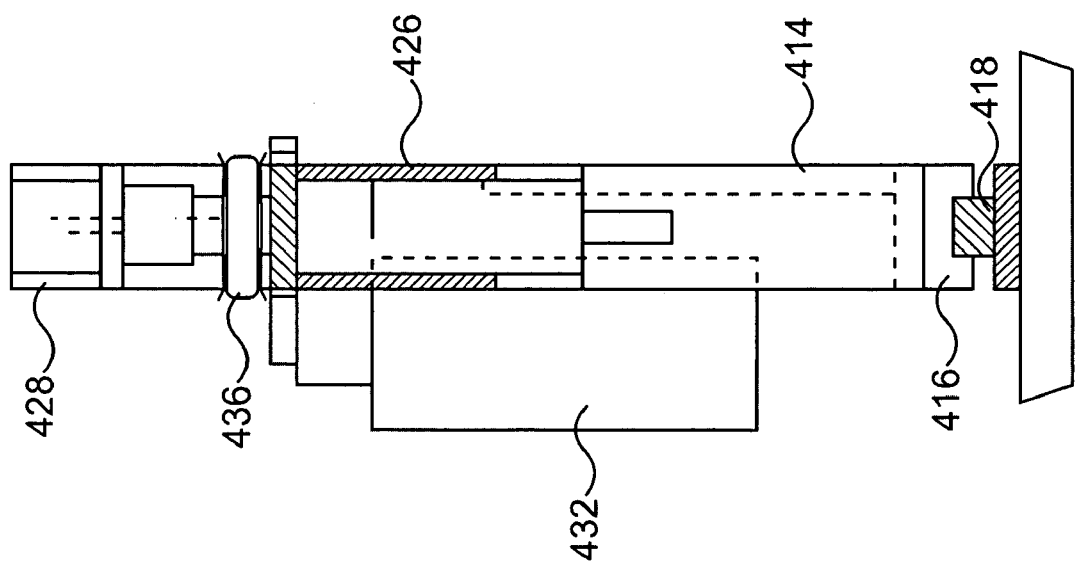
FIG. 30 is a sectional view taken along line 30-30 in FIG. 29.
Figure 32:
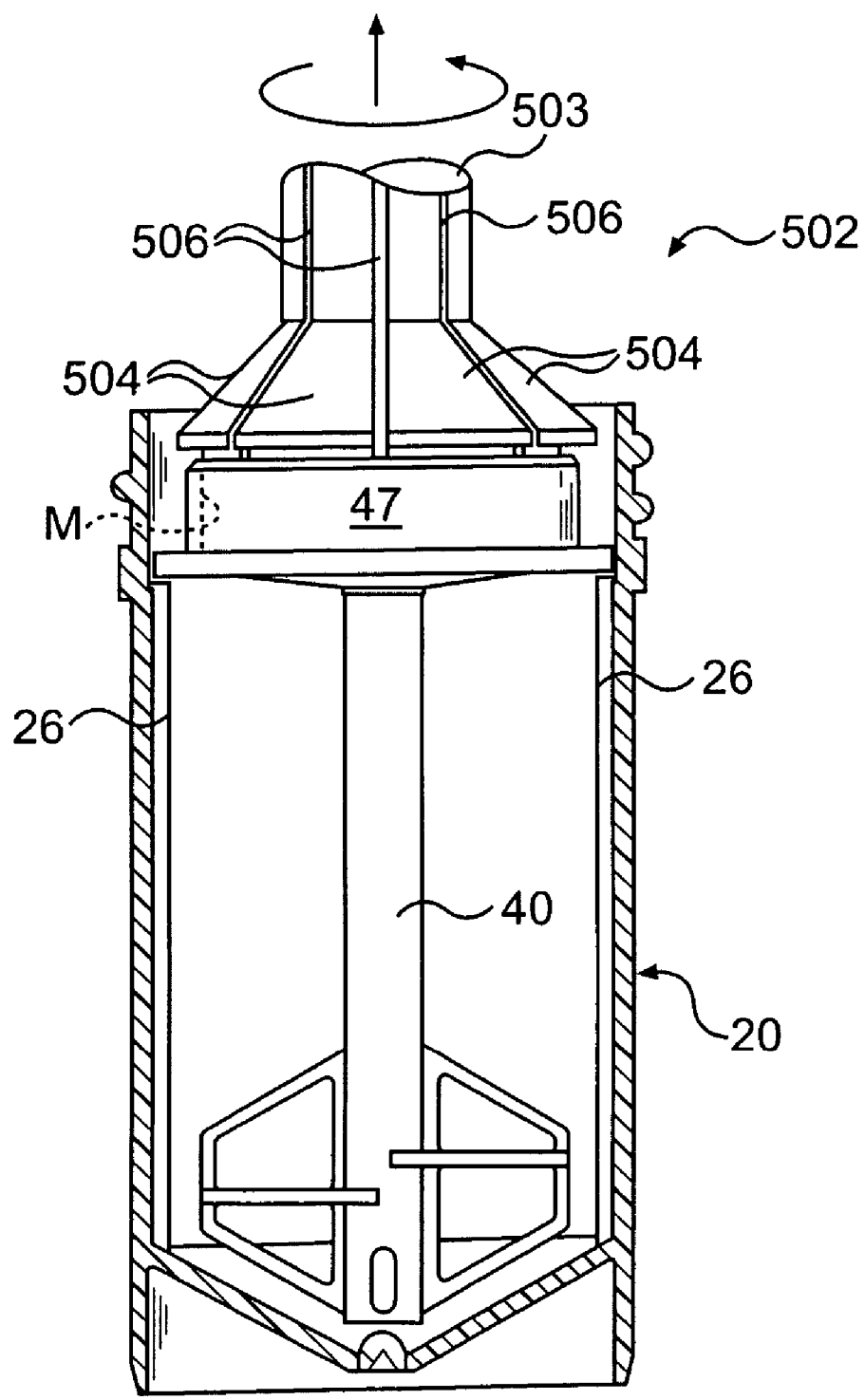
FIG. 32 is a vertical sectional view of a specimen container showing engagement by the primary stirring head.
Figure 33:
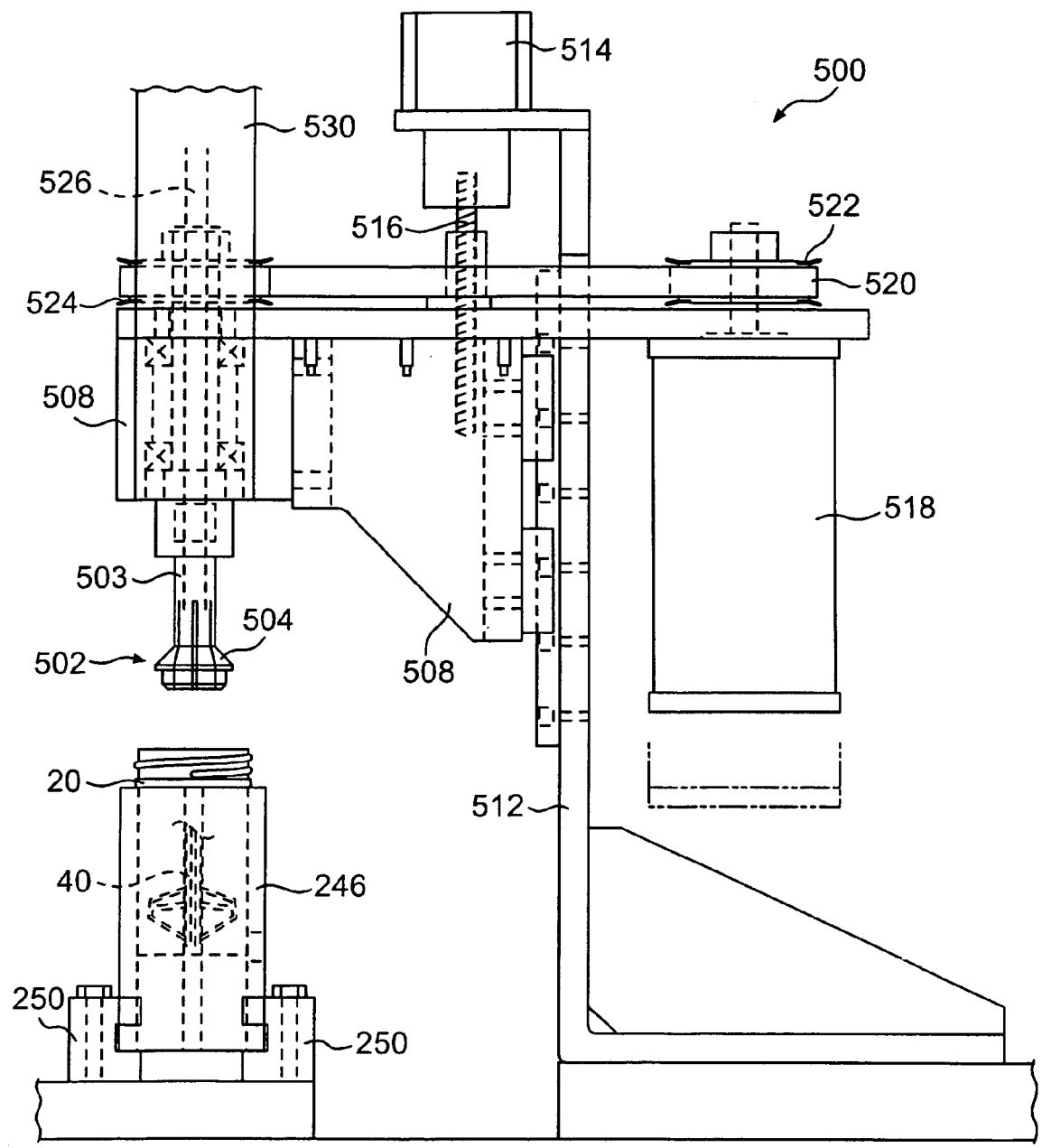
FIG. 33 is a side elevational view of the primary stirring station of the LBP device.
Figure 35:
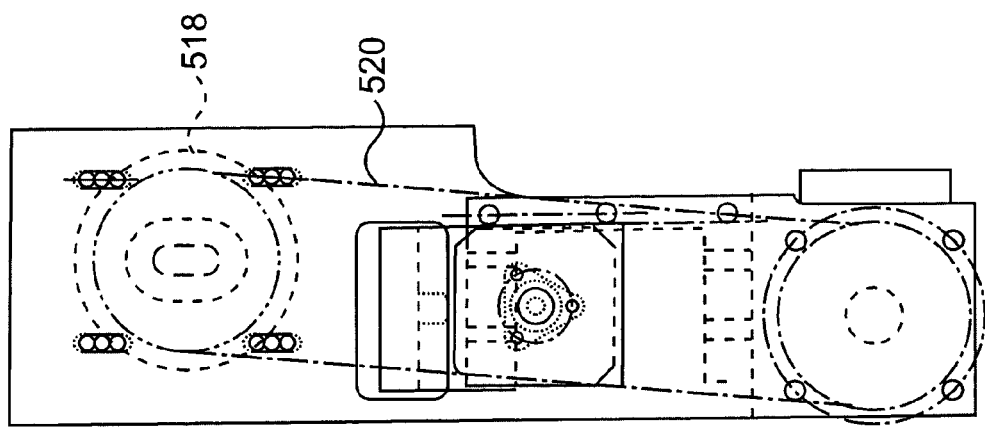
FIG. 35 is a top plan view of the primary stirring station.
Figure 34:
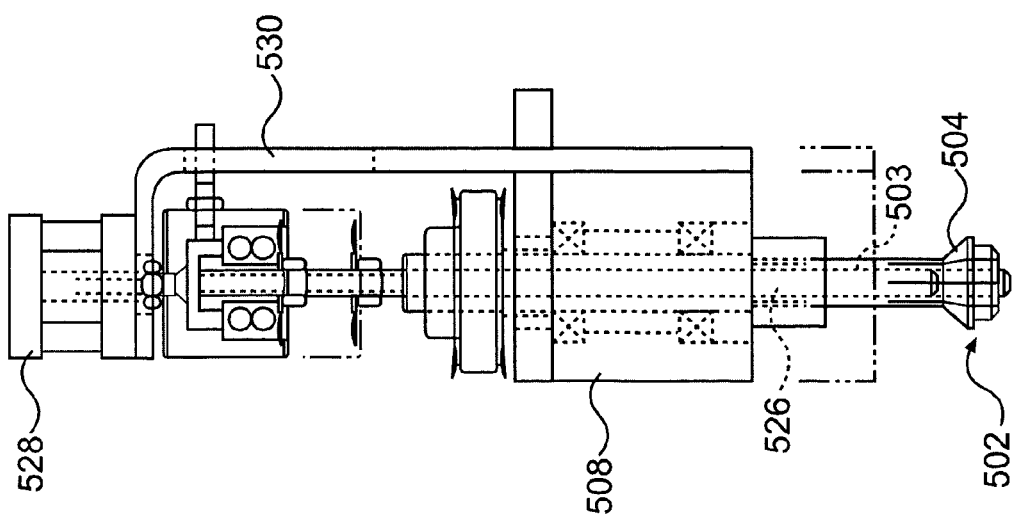
FIG. 34 is a front elevational view of the primary stirring station.
Figure 36:
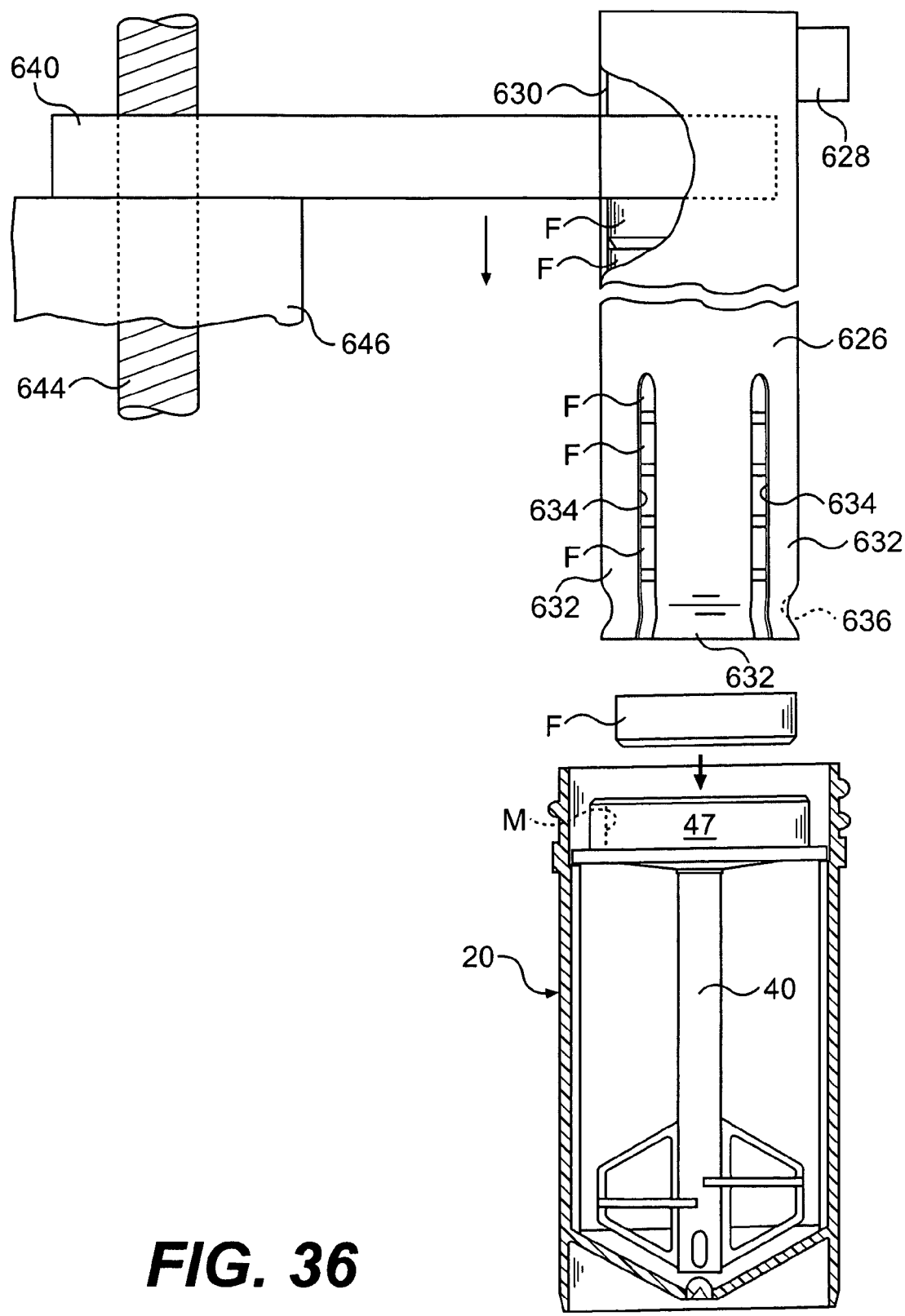
FIG. 36 is a vertical sectional view of a specimen container during filter loading.

FIG. 22 is a block diagram showing the components of a general purpose computer system or work station 270, which can be used to run the DMS. The computer system 270 typically includes a central processing unit (CPU) 272 and a system memory 274. The system memory 274 typically contains an operating system 276, a BIOS driver 278, and application programs 271, such as a DMS. In addition, the computer system 270 can include input devices 273, such as mouse, keyboard, microphone, joystick, optical or bar code reader, etc., and output devices, such as a printer 275P, and a display monitor 275M.

The computer system or work station can be connected to an electronic network 280, such as a computer network. The computer network 280 can be a public network, such as the Internet or Metropolitan Area Network (MAN), or other private network, such as a corporate Local Area Network (LAN) or Wide Area Network (WAN), or a virtual private network. In this respect, the computer system 270 can include a communications interface 277, such as ethernet, USB, or Firewire, which can be used to communicate with the electronic network 280. Other computer systems 279, such as a remote host database, other types of work stations including automated analyzers, and computers or databases (e.g., LIS) of a hospital, laboratory, or other medical establishment, can also be linked to the electronic network 280. Other LBP devices, as well as other types of specimen processing instruments (e.g., automated slide stainers and coverslippers) 279a can also be connected to each other and the DMS via the network.

One skilled in the art would recognize that the above-described system includes typical components of a general purpose computer system connected to an electronic network. Many other similar configurations can be used to control the LBP device and its processes. Further, it should be recognized that the computer system and network disclosed herein can be programmed and configured by one skilled in the art to implement the methods, system, and software discussed herein, as well as provide requisite computer data and electronic signals to implement the present invention.

In addition, one skilled in the art would recognize that the "computer" implemented invention described further herein may include components that are not computers per se, but include devices such as Internet appliances and Programmable Logic Controllers (PLCs) that may be used to provide one or more of the functionalities discussed herein. Furthermore, while "electronic" networks are generically used to refer to the communications network connecting the processing sites of the present invention, one skilled in the art would recognize that such networks could be implemented using optical or other equivalent technologies. One skilled in the art would recognize that other system configurations and data structures can be provided to implement the functionality of the present invention. All such configurations and data structures are considered to be within the scope of the present invention. In this context, it is also to be understood that the present invention may utilize known security and information processing measures for transmission of electronic data across networks. Therefore, encryption, authentication, verification, compression and other security and information processing measures for transmission of electronic data across both public and private networks are provided, where necessary, using techniques that are well known to those skilled in the art.

Uncapping Station

One of the advantages of the present vial-based LBP device and system is that it minimizes operator exposure to the specimens, which can contain potential biohazards. Referring to FIGS. 26-31, the LBP device has an uncapping mechanism 400 that first automatically separates the stirrer 40 in the vial from cover 30, and then removes and discards the cover—all without intervention by an operator. See FIG. 26, which shows the stirrer resting on vial ribs 26 after the cover 30 is removed.

A closed specimen vial 10 which has arrived at the uncapping station in its transport receptacle 246 is met by an uncapping head 402 which is lowered onto the cover 30 of the specimen vial. See FIGS. 27 and 28. Uncapping head 402 has four tapered legs 404 that form a tapered gripping cavity having chisel-like inner edges 406 spaced and sized to progressively tighten onto cover 30 as head 402 is lowered. Once the cover is tightly engaged by the legs, a central spindle or plunger 408 is lowered into contact with the center of cover 30 and applies a downward force to the cover to cause the stirrer 40 to detach from the cover 30, as described above, and drop down in the vial onto ribs 26. Then the plunger is retracted and the uncapping head 402 is rotated counterclockwise (FIG. 28) to unscrew cover 30 and remove it from container 20. Thereafter the uncapping head with the removed cover in its grip moves laterally to the position shown in dashed lines 410 in FIGS. 29 and 11, and plunger 408 is again lowered, this time to eject cover 30, which falls into a waste chute or bin (not shown) beneath the uncapping head. Alternatively, a movable waste chute can be brought beneath the uncapping head to catch the ejected cover, so that lateral movement of the uncapping head is not required. Covers are not reused to eliminate the possibility of cross-contamination.

The plunger 408 is driven by a pneumatic cylinder 412, mounted on an L-bracket 415 at the top of the uncapping head, that can apply a force on the cover of up to about 30 lbs. A coil spring 413 returns the plunger to its retracted position when cylinder 412 is deactivated. The head 402 is capable of applying an uncapping torque through the gripping legs of up to about 10 lb-ft, which is sufficient to loosen the cover. The gripping legs can be of the self-energizing type so that precise alignment with the cover or small variations in cover geometry do not frustrate their grip.

The uncapping mechanism has a mounting frame 414 supported on blocks 416 that slide laterally of the processing path on rails 418. A Y-axis stepper motor 420 and lead screw 422 effect lateral motion. The uncapping head 402 is rotatably mounted in a bearing block 424. Bearing block 424 is secured to a C-frame 426 that is vertically slidable on mounting frame 414. Vertical movement of C-frame 426 and, hence, uncapping head 402 is effected by Z-axis stepper motor 428 and lead screw 430. Lead screw 430 can be vertically compliant to accommodate upward movement of the cover 30 as it is unscrewed. However, it is preferred that stepper motor 428 be actuated during the uncapping sequence so that head 402 rises at about the same rate as, but no faster than, the unthreading cover. Uncapping head 402 is rotatably driven by uncapper motor 432 through a gear reduction unit 433, a timing belt 434 and timing pulleys 436, 438.

The uncapping head described above would also work with vials having a conventional "press and turn" bayonet-type coupling between the container and the cover. The downward force of the plunger 408 would be sufficient to release the internal anti-turn lock of the coupling, allowing the gripper to rotate and remove the cover. Vials having covers that do not require rotation for removal, e.g., a snap-on cover, would require a differently designed uncapping head, tailored to the type of cover connection involved.

Alternatives to the above-described plunger 408 can be employed at or upstream of the uncapping station for applying the required external force to the covered vial to effect separation of the stirrer from the cover. For example, a cam, lever arm or other movable mechanical element can contact and press down on the cover. Alternatively, an abrupt upward external force can be applied to the vial to yield an acceleration force that overcomes the frictional retention force between couplers 35 and 47, effectively pulling the stirrer out of engagement with the cover. This can be done by, e.g., moving the closed vial rapidly downwardly to rap the bottom of the container 20 against a rather hard surface, e.g., by mechanically and/or pneumatically thrusting the closed vial into the transport carrier 246 that will hold the vial during the subsequent processing steps, or by dropping the vial down a chute into the carrier a sufficient distance to dislodge the stirrer. Another way to exert an abrupt upward external force on the vial is to strike the bottom of the container 20 with a striking member. This can be accomplished by, e.g., cradling the container 20 and momentarily thrusting a striker against the bottom of the container, e.g. through a bottom opening in the vial carrier 246, by pneumatic and/or mechanical means. The design of these and other variants of suitable automated mechanisms for accomplishing these tasks is within the grasp of those skilled in the mechanical arts.

Preprocessing (Primary Stirring) Station

After uncapping is completed, the transport mechanism indexes the specimen container to a station where preprocessing occurs. The preprocessing station is the location at which preprocessing operations, such as specimen dispersal within its container, are performed prior to the container and its specimen moving to the specimen acquisition station. The preprocessing station typically performs a dispersal operation. In the preferred embodiment, the dispersal operation is performed by a mechanical mixer, which rotates at a fixed speed and for a fixed duration within the specimen container. In this example, the mixer serves to disperse large particulates and microscopic particulates, such as human cells, within the liquid-based specimen by homogenizing the specimen. Alternatively, the specimen may contain subcellular sized objects such as molecules in crystalline or other conformational forms. In that case, a chemical agent may be introduced to the specimen at the preprocessing station to, for example, dissolve certain crystalline structures and allow the molecules to be dispersed throughout the liquid-based specimen through chemical diffusion processes without the need for mechanical agitation. In this example, the chemical preprocessing station introduces its dispersing agent through the preprocessing head.

In the illustrated preferred embodiment preprocessing occurs at the primary stirring station 500, which uses a specified or instructed stirring protocol to stir the specimen, if needed, using the stirrer 40 in the container, at a specified speed (rpm) for a specified duration. The stirring protocol chiefly depends on the specimen, as described above, and is normally intended to disaggregate any mucous material and disperse it and/or other particulate material in the specimen liquid.

Referring to FIGS. 32-35, the primary stirring station 500 has a stirring head 502 in the form of an expanding steel collet. The collet is formed at the lower end of a shaft 503 which splits into six flexible fingers 504 defined by six equally spaced slits 506. Shaft 503 is rotatable in a bearing block 508 secured to a C-frame 510 that is vertically slidable on a mounting frame 512. Vertical movement of C-frame 510 and, hence, stirring head 502 is effected by a Z-axis stepper motor 514 and a lead screw 516. Stirring head 502 is rotatably driven by a stirring motor 518 through a timing belt 520 and timing pulleys 522, 524.

The inner surfaces of the collet fingers 504 taper uniformly inwardly toward the lower end of the collet. A central plunger 526, movable vertically by a pneumatic cylinder 528 atop a bracket 530, expands the fingers 504 outwardly when it descends and encounters the narrowing passage defined by the tapering fingers. Thus the diameter of the lower end of the stirring head (collet) 502 increases when the plunger descends. This end is sized to fit loosely but closely within the annular wall 47 at the top of stirrer 40 when the collet is not expanded. When plunger 526 descends, the fingers 504 expand outwardly to wedge against the inside of wall 47, in manifold M, securely engaging the stirrer.

In operation, the stirring head 502 is first lowered so that the collet enters the manifold M. The dashed motor and bracket lines in FIGS. 33 and 34 indicate this lowered position. Then plunger 526 descends to lock the stirring head to the stirrer. Then the stepper motor 514 is operated to slightly raise the stirring head and the attached stirrer 40. This vertical movement need only be very small, such as 0.050 in., just to free the stirrer from the ribs 26 and prevent interference with the container during stirring. Then DC stirring motor 518 is operated in accordance with the specimen-specific stirring protocol. Stirring speed can vary, and is usually in the range of about 500 rpm to about 3,000 rpm. The stirring time can vary from about 5 seconds to about 90 seconds. The base or bottom wall 41 of the stirrer acts as a slinger to thrust any liquid that may rise along the stirrer against the container wall, and prevents the escape of liquid from the container. Withdrawing the plunger 526 from the collet releases the stirrer 40 from the collet 502 so the specimen container can move on to the next station.

A contracting collet could be used instead of expanding collet 502. In that case, the collet fingers would fit around the outside of annular wall 47, and would be squeezed together to clamp around the wall by a descending sleeve that surrounds the fingers.

Filter Placement Station

At the filter placement station 600 an appropriate filter assembly F (see FIG. 5) is loaded into the open manifold M at the top of the stirrer 40. Filter assemblies can come in different filter configurations for automated machine recognition. For example, one set of filter assemblies can be colored red (5 micrometers), another set white (8 micrometers), each having different filtering properties, and a color sensor can detect which type of filter is before it and cause the proper filter to be loaded. The filter assemblies are dispensed by a pusher from a magazine having multiple filter tubes.

Figure 39:
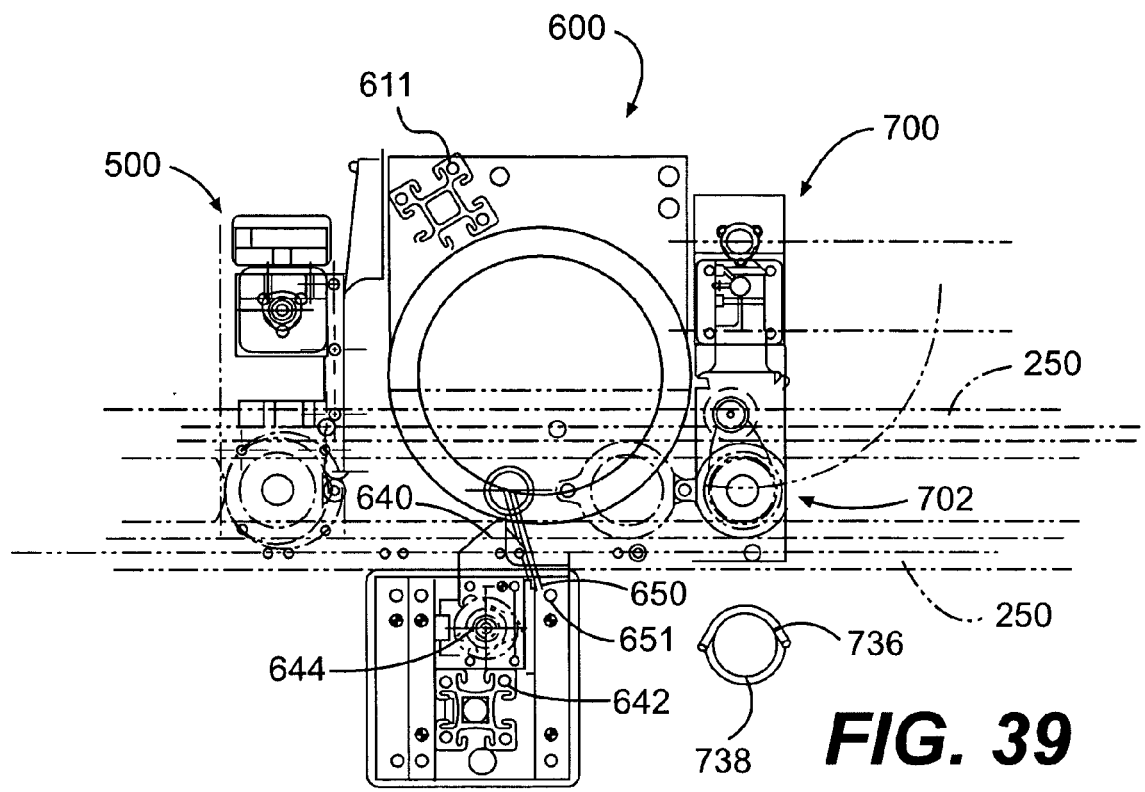
FIG. 39 is a top plan view of the pusher portion of the filter loading station.
Figure 40:
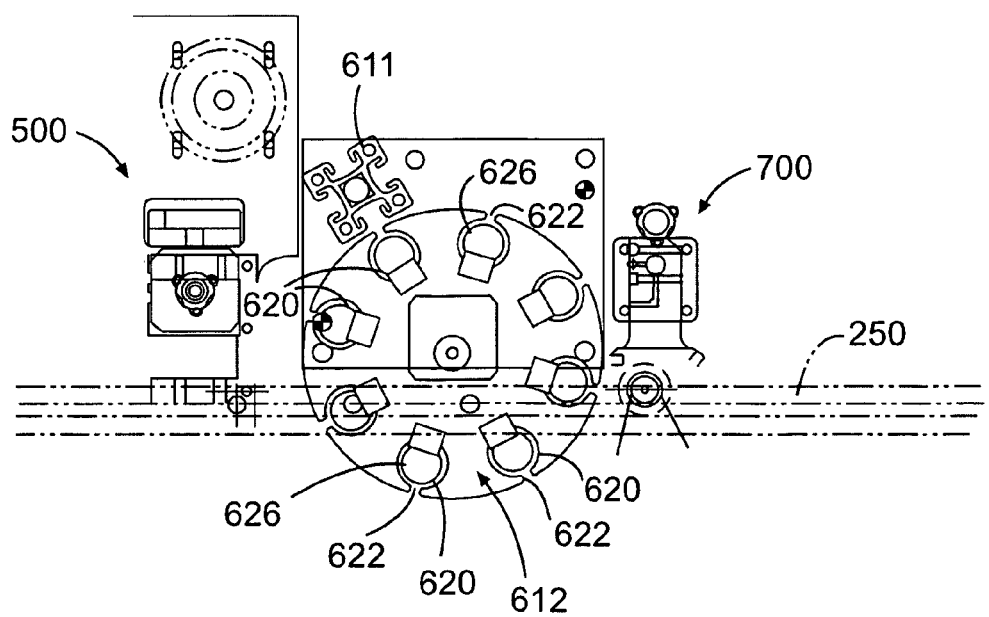
FIG. 40 is a top plan view of the magazine portion of the filter loading station.

FIGS. 36-40 show the structure and operation of the filter placement station. Referring to FIGS. 37 and 40, a filter dispensing head 610 comprises a filter magazine in the form of a turret 612 rotatable on a spindle 614 by a stepper motor 616. Vertical post 611 provides the main support for the turret. Turret 612 has a top support plate 618 with eight equally spaced holes 620 near its periphery, each hole opening through the edge of the plate 618 with a slot 622. A bottom guide plate 624 on spindle 614 has a similar arrangement of holes that are aligned with the holes and slots in the top support plate.

Eight steel filter tubes 626, each having an upper support shoulder 628, are supported vertically in holes 620 and the aligned holes beneath them, with shoulders 628 resting on the top of top plate 618. Each filter tube 626 has a full-length slot 630, and its bottom portion is split into four springy fingers 632 by slots 634. Just above the bottom end the fingers 632 curve inwardly, forming rounded inner shoulders 636 against which a filter assembly F rests. The filter tube is dimensioned such that the shoulders 636 keep up to a full stack of filter assemblies F from falling out of the tube, but deflect to allow a filter assembly to pass when the stack is pushed downwardly without damage to the filter assembly. Fingers 632 thus form a springy choke.

FIG. 39 shows the position of the filter magazine 612 in relation to the processing path and the adjacent processing stations, namely the primary stirring station 500 to the left, and the specimen acquisition station 700 to the right, all located on one side of the processing path as defined by guide rails 250. On the other side of the processing path opposite the filter magazine 612 is the assembly that supports and drives a pusher arm 640. This assembly comprises a support post 642 supporting a Z-axis lead screw 644 driven by a stepper motor (not shown) which moves a shuttle 646 that carries pusher arm 640. A filter sensor 650 positioned opposite bottom guide plate 624 monitors the passage (drop) of the lowest filter assembly F in the filter tube presented to (i.e., directly above) the specimen container. Sensor 650 also detects when the filter tube is empty. A second sensor 651 monitors filter type.

Filter assemblies of the same type are stacked in the proper orientation, with the membrane filter side (beveled edge) facing down, in each tube. For example, 54 filter assemblies can be housed in each tube; thus a total of 432 filter assemblies can be loaded into the magazine. Fifty-four filter assemblies can be prepackaged in a stack that is inserted into a filter tube with a wrapper tab projecting from slot 630, and unwrapped by pulling the tab outwardly. Alternatively, filter assemblies of the same type can be dumped onto a vibratory feeder, which can recognize their orientation by geometric configuration, and properly orient and feed the filter assemblies onto the tubes. Several of these feeders can be used, one for each type of filter assembly.

In operation, with the pusher arm 640 in its home (top) position, indicated by the dashed shuttle outline in FIG. 38, the filter magazine 612 is rotated by stepper motor 616 until sensor 650 detects the presence of the specified type of filter assembly in the filter tube before it. Shuttle 646 then moves downwardly with pusher arm 640 moving through slot 630 to press the stack of filter assemblies in that tube downwardly, until the lowest filter assembly drops from the tube into the manifold M in stirrer 40. When filter drop is sensed, the shuttle 646 with its pusher arm 640 stops its advance. In an alternative arrangement, a weight sensor can be used to monitor the weight of the filter stack, and detect by weight change when a filter assembly has dropped from the stack and when the filter tube is empty.

The use of eight filter tubes 626 in magazine 612 enables unattended processing of all of the specimens housed in the trays of the vial autoloader 300. For a counter-top model of the type described above, however, a single filter tube supported in a fixed position above the processing path would suffice for processing specimens that require the same type of filter.

Specimen Acquisition and Cell Deposition Station

Figure 41:
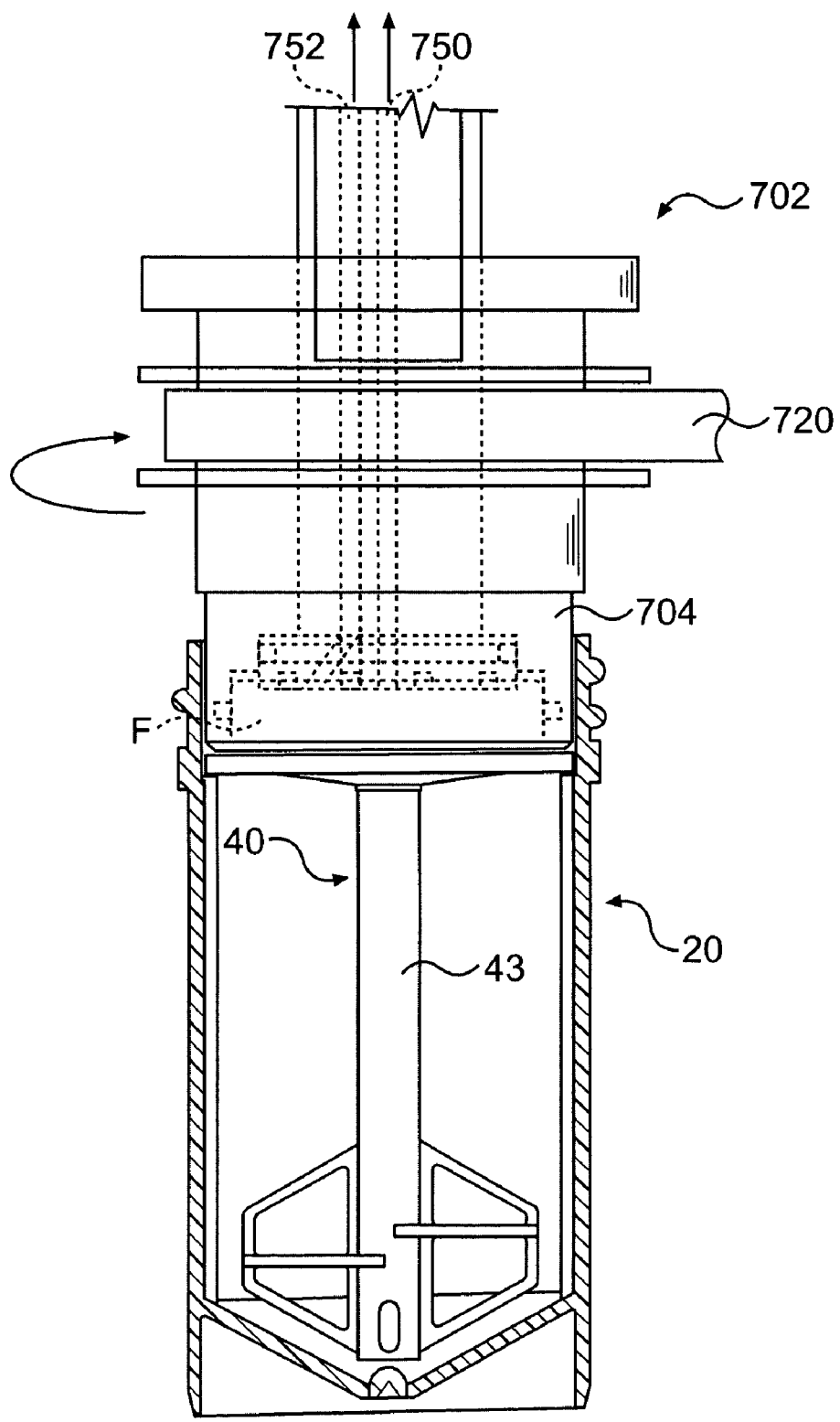
FIG. 41 is a vertical sectional view of a specimen container during specimen acquisition.

Referring to FIG. 41, specimen acquisition station 700 has a suction head 702 that descends to engage the upper portion of the stirrer 40. Before drawing a vacuum on the specimen through the filter assembly F, the suction head grips, slightly lifts and rotates the stirrer 40, this time more slowly than at the primary stirring station (typically no more than 500 rpm for a 5 second interval), to re-suspend the particulate matter in the specimen liquid. The re-stir motor can be a Maxon 24 volt DC planetary gear-reduced type. Then suction is applied through suction line 750 to aspirate specimen liquid from the container 20 through suction tube 43, into the particulate matter separation chamber (manifold) 46 and through the filter assembly F, leaving a monolayer or thin layer of uniformly deposited cells on the bottom surface of the filter as described above. It may also be possible to rotate the stirrer slowly while the specimen liquid is being aspirated.

FIG. 6 shows how the suction head cooperates with the annular wall 47 of the stirrer manifold and the filter assembly F therein. The outer portion 704 of the suction head envelops the wall 47 and has an O-ring 760 that seals against the outside of wall 47. The inner portion 706 of the suction head has two concentric O-rings 762, 764 that seal against the top of filter holder 200. Suction applied through port 750 creates a vacuum around central opening 204 and within filter holder 200, which draws liquid into the manifold 46 and through the filter 202. An O-ring 766 is interposed between the inner and outer portions of the suction head.

Figure 42:
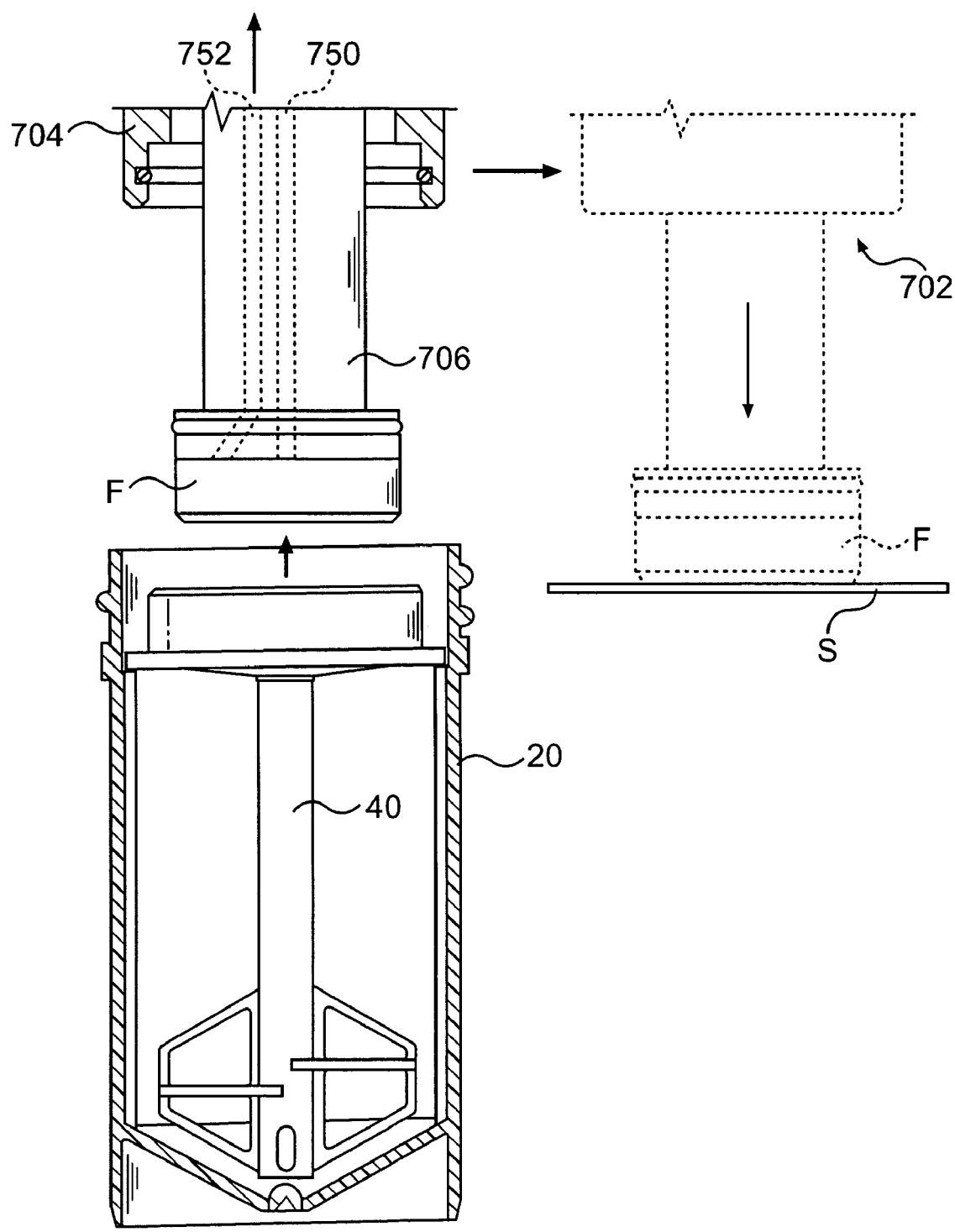
FIG. 42 is a vertical sectional view of a specimen container during specimen transfer to a slide.

Referring to FIG. 42, when aspiration of the specimen is complete, the suction head 702 is raised. The inner portion 706 of the suction head is extended at the same time by action of a pneumatic cylinder (not shown) mounted above the suction head. As the suction head 702 is raised, the outer portion 704 disengages from the stirrer 40, but the filter assembly F is retained on the inner portion 706 by application of a vacuum through suction line 752 to the annular space between O-rings 762 and 764. Thus the suction head 702 removes filter assembly F from the stirrer, and can continue to apply light suction via suction line 750 through the filter to effect a desired degree of moisture control of the cellular material on the filter.

Figure 46:
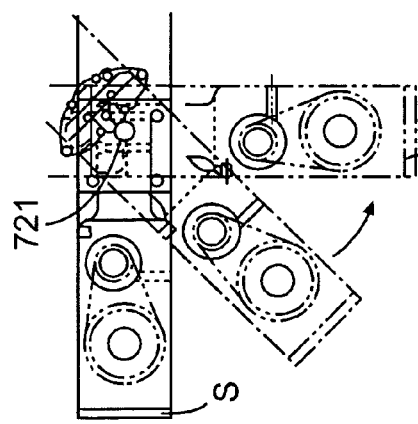
FIG. 46 is a top plan view of the specimen acquisition station.
Figure 44:
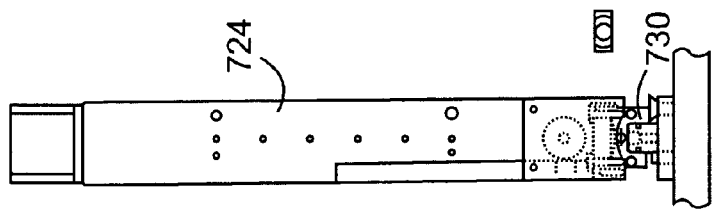
FIG. 44 is a front elevational view of the lower portion of the specimen acquisition station.

The suction head 702 then moves laterally away from the transport conveyor by pivoting 90° about a vertical axis to the cell transfer position "P" shown in FIG. 46, to position the filter assembly F over a microscope slide S delivered from a slide cassette at slide presentation station 900. This pivoting movement of suction head 702 can also be seen in FIGS. 11 and 39. The inner portion 706 of the suction head 702 then moves downwardly to press the filter against the slide S with a tamping force in the range of 4 to 8 lbs. and transfer the monolayer of cells thereto. The phantom lines in FIG. 42 show this change in position of suction head 702 and contact of the filter with slide S. Instead of being pivotally mounted, the suction head 702 could be mounted for rectilinear movement to and from a different deposition site where slides are presented, e.g., above the processing path.

Referring to FIGS. 43-46, suction head 702 is rotatably mounted on a boom 716 that also carries the re-stirring motor 718, which rotates suction head 702 through a timing belt 720. Boom 716 is pivotally supported about a vertical axis 721 on a slide 722, which is vertically movable along frame support 724 by means of a Z-axis stepper motor 726 and a lead screw 728. Motor 726 thus moves the entire suction head vertically. Pivoting motion of boom 716 is effected by stepper a motor 717 operating through a gear train (not shown). Vertical motion of the inner portion 706 of the suction head is effected by a pneumatic cylinder and return spring (not shown) mounted above the suction head to an L-bracket 719, substantially identical to the arrangement 412, 413, 415 (see FIG. 29) used to move the plunger 408 of the uncapping head 402.

Figure 43:
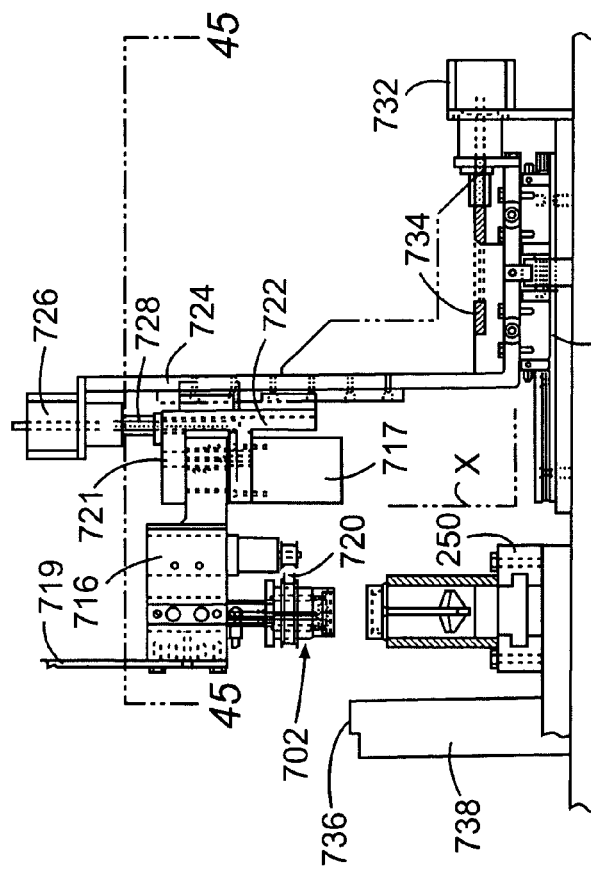
FIG. 43 is a side elevational view of the specimen acquisition station of the LBP device.
Figure 45:
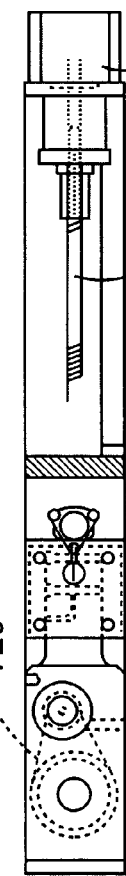
FIG. 45 is a top plan view of the specimen acquisition station, partly in section, taken along line 45-45 in FIG. 43.

The frame support 724 is mounted on a slide 730 so as to be movable laterally of the transport path. A Y-axis stepper motor 732 and a lead screw 734 effect this movement. After the slide is printed the suction head is raised by the Z-axis motor, and the Y-axis stepper motor 732 advances the entire assembly to the dashed line position "X" shown in FIG. 43. Then the suction head pivots back to its original orientation, transverse to the transport path (position "S" in FIG. 46). The Y-axis stepper motor 732 then pulls the entire assembly back toward its original position (solid lines in FIG. 43). As the suction head 702 moves (to the right as seen in FIG. 43), the still-retained filter assembly F is "scraped" off the suction head by the edge 736 of an open-top used filter (waste) tube 738 (see also FIGS. 11 and 39). This leaves suction head 702 free to engage a fresh filter assembly.

The vacuum source that communicates with the suction head 702 pulls a slight vacuum, e.g., in the range of 3 in. to 10 in. Hg (adjustable by a regulator), through suction line 750 to aspirate specimen liquid and draw it through the filter assembly F. The separately regulated vacuum applied through suction line 752 for holding the filter assembly to the suction head 702 is higher, on the order of 20 in. Hg.

Formation of high-quality specimens on microscope slides depends critically on the deposition of a monolayer of cells of specified concentration (i.e., number of cells per unit area) on the surface of the filter that will contact the slide. That, in turn, depends critically on the aspiration rate and/or the aspirated flow volume. Since cell concentration on the filter surface is a function of the number of filter pores blocked by the solids suspended in the specimen liquid, the percent of flow reduction from the maximum open filter condition correlates to the blockage or amount of accumulation on the filter. Because of the nature of biological specimens, solid particle concentration is a significant variable in the process and must be taken into consideration. Also, it is important to identify the total volume of material filtered on a real time basis for other processing operations.

The specimen acquisition station thus further includes a deposition control system for controlling the liquid draw vacuum duration by monitoring the flow rate and/or aspirated volume. The monitored flow rate or aspirated volume can be used to signal vacuum cut-off and/or suction head retraction, which correlates to the specified concentration of cells collected on the membrane filter surface. If a specified concentration factor is not achieved before a specified volume of fluid is aspirated, the system can also issue a retract signal.

Figure 47:
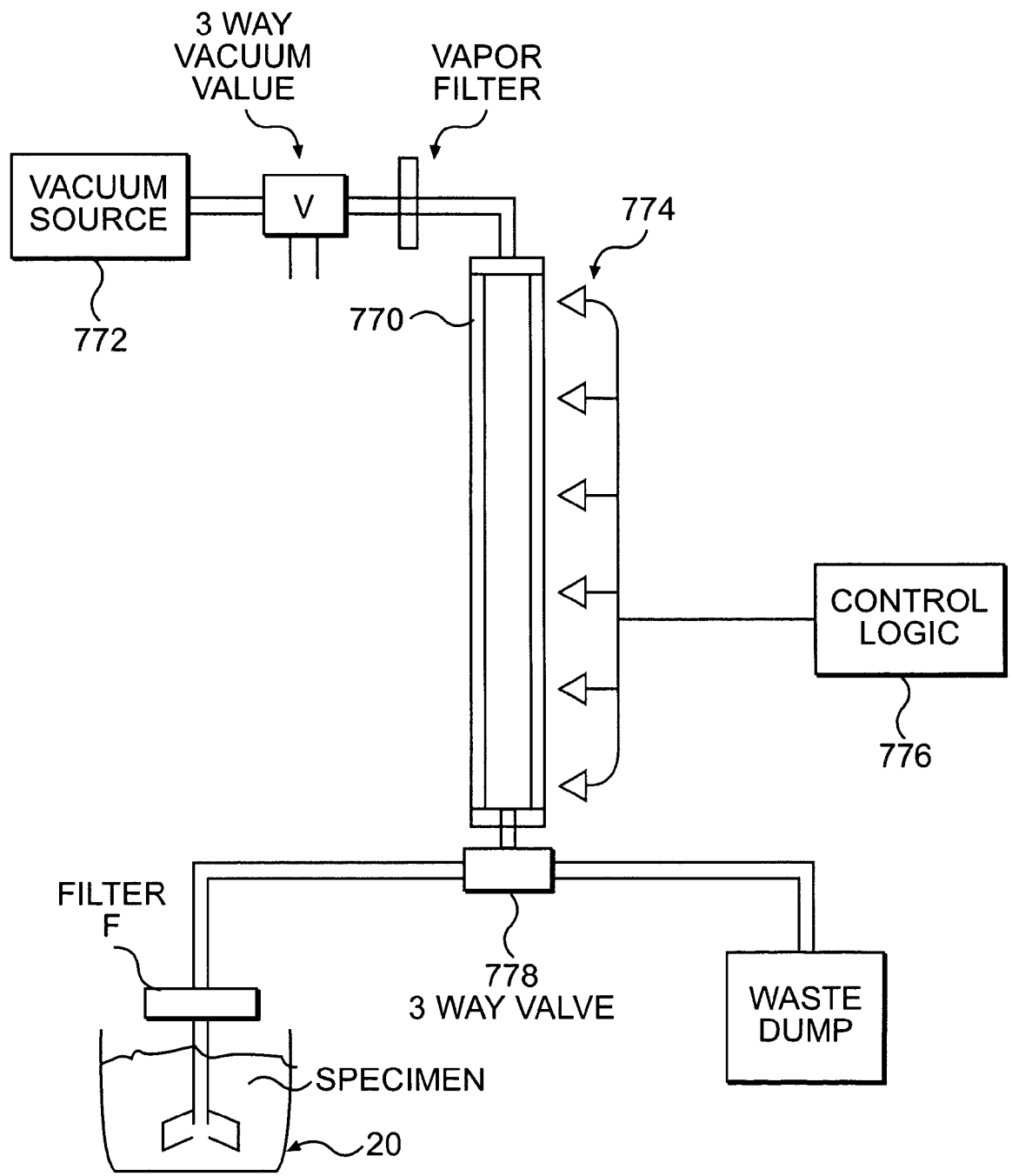
FIG. 47 is a schematic of a bubble flow meter used in the specimen acquisition station.

Different types of deposition control systems or modules can be used for these purposes. FIG. 47 schematically shows one such system, which has a meter in the form of a digital level detector positioned along a fluid column. This "bubble flow" system can use sensors in the form of a plurality of LED emitters and corresponding number of photosensors, such as Omron sensor, EE-SPX613 GaAs infrared LED, placed along the length of the column. Any other type of sensors may be used. Alternatively, LED sensors such as the Omron sensors mentioned above can be used without corresponding emitters when they are positioned just at the edge of a glass tube. The meniscus edge of the liquid in the tube diffracts the light passing through the tube, and the sensor will detect the shifted light pattern when the rising meniscus edge reaches the sensor.

The fluid column is formed in a vertically extending transparent tube or cylinder 770, e.g., one made of Pyrex glass 9 mm in diameter by 1 mm thick. The aspirated specimen fluid is drawn from the specimen container through the membrane filter, and pulled into the glass cylinder 770 via suction line 750 and a 3-way valve 778, by means of a vacuum source 772 connected to the top of the cylinder. The sensors 774 are positioned evenly along the length of the cylinder 770, preferably at 1.5 ml capacity intervals, and are interfaced with a controller or microprocessor 776.

In operation, in the normal state, with no fluid in the tube 770, the sensor relay line is "low." Vacuum begins to draw fluid into the tube through the filter, and the controller marks the beginning of the draw sequence. When the fluid reaches the first sensor, the first sensor relay line goes "high." The controller marks the time it took for the fluid to reach the first sensor, indicating the nearly free-flow condition of the filter, and the relative viscosity of the fluid in the test. When an additional 1.5 ml of fluid is drawn into the tube, the second sensor relay line goes "high." The time interval for the first 1.5 ml of fluid (between the first and second sensors) is noted by the controller, and this becomes the reference time base. As each additional 1.5 ml of fluid is drawn into the system (and is detected by succeeding sensors), the time base for that increment is computed. When the incremental time base reaches an empirically derived percentage (e.g., 120%) of the original (reference) time base, the controller indicates that cell collection is completed, and a stop signal is transmitted, preferably to retract the suction head 702 from the manifold in the specimen container. The empirically derived figure mentioned above is variable with the protocol and directly controls the cellularity of the specimen sample.

Figure 47A:
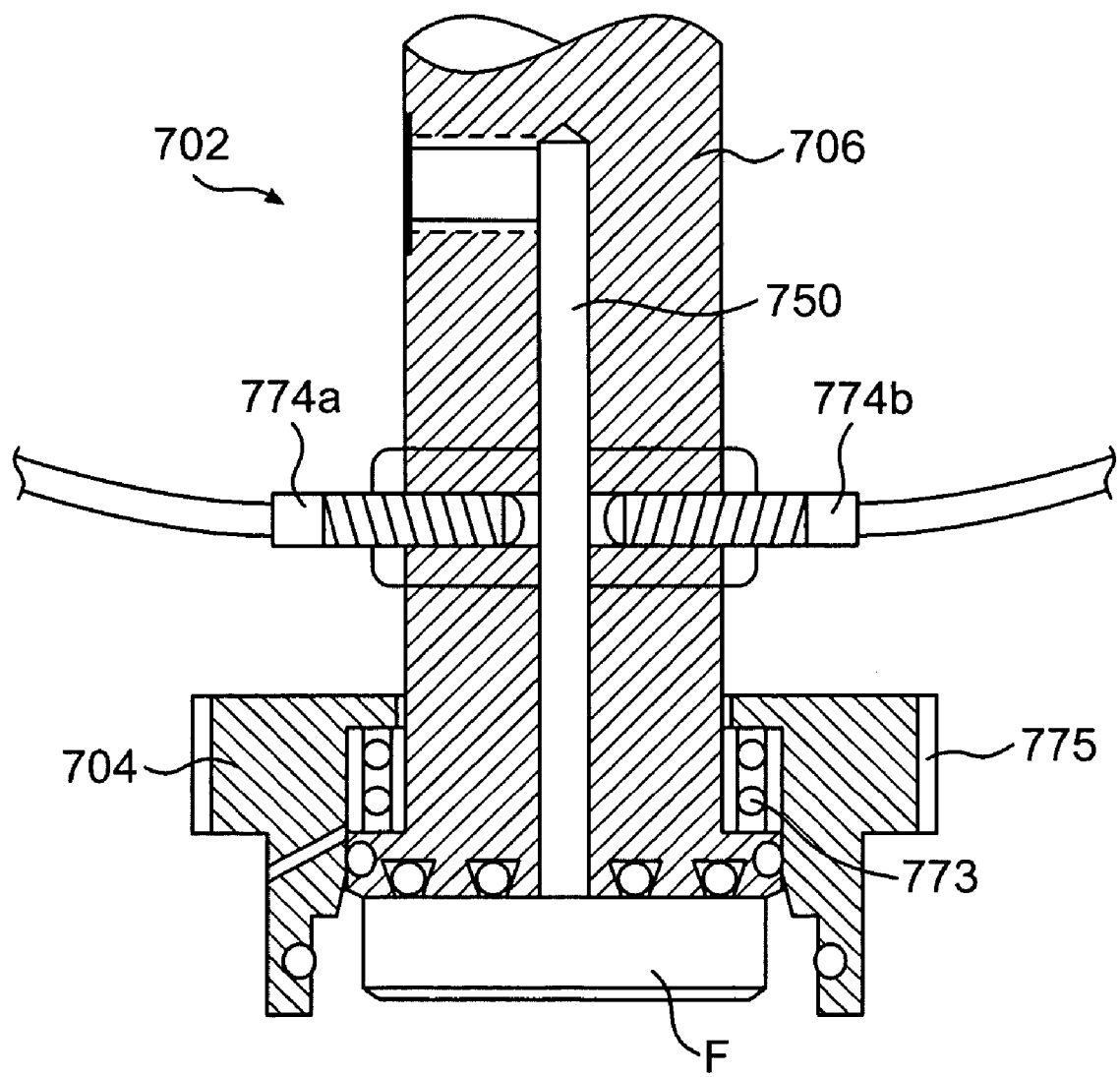
FIG. 47a is a schematic of a modification of the flow meter of FIG. 47.

The best approximation of the free-flow condition of the filter is obtained if the time it takes for the fluid to reach the first sensor 774 is kept to a practical minimum. This can be accomplished by incorporating the first sensor into the suction head itself, as schematically illustrated in FIG. 47a. In this embodiment, inner portion 706 of the suction head carries an emitter 774a and an opposed sensor 774b, which detects the leading edge of the fluid column very close to the filter assembly F. The outer portion 704, which has teeth 775 engaged by timing belt 720 (not shown), is rotatable about the inner portion 706 (note interposed bearing 773) to rotate the stirrer (not shown) and stir the specimen prior to aspiration.

During the specimen drawing operation, the controller records the cumulative or total aspirated volume. If the cumulative volume reaches a predetermined level before reaching the predetermined flow rate reduction from the reference flow, the controller will also issue a stop signal and a flag indicating that the stop signal issued not as a result of desired reduced flow, but by reaching the maximum liquid draw limit. A slide formed under the flagged condition will likely form a hypo-cellular condition. The controller can imprint the slide and indicate to the DMS that a hypo-cellular condition likely exists. Accordingly, if the flagged condition exists, the controller issues a signal to purge the liquid in the cylinder 770 and initiate a second draw. The cylinder is purged of all liquid after each sample is taken.

Figure 48:
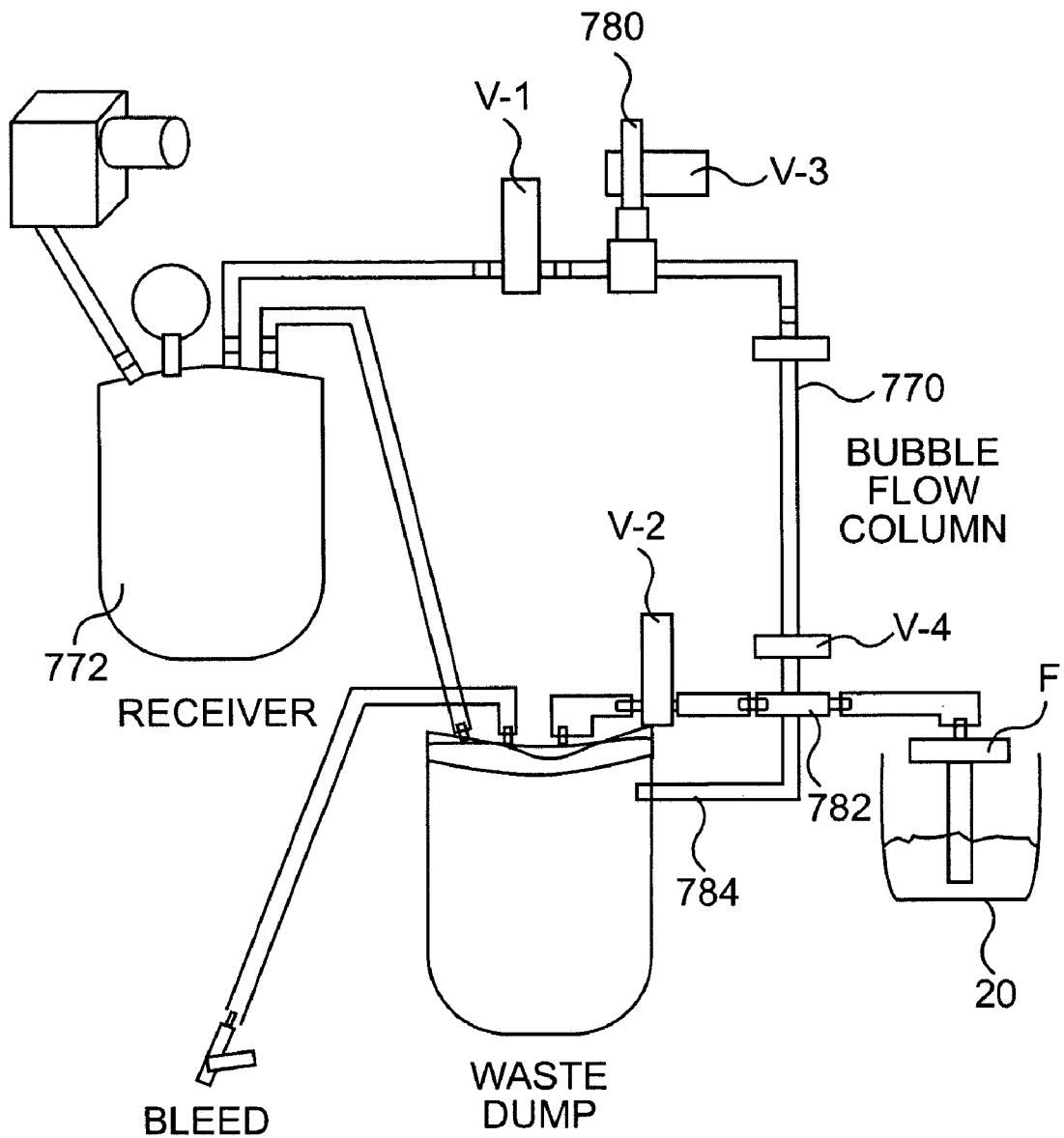
FIG. 48 is a schematic of a vacuum system used in the specimen acquisition station.

Referring to FIG. 48, the deposition control system can have a purge value so that when the draw cycle is completed, the stop signal generated by the controller 776 will open the purge valve to vent the vacuum supply line to the atmosphere and divert the liquid remaining in the cylinder 770 into a waste container. The cylinder 770 can be maintained under a negative pressure. The system is then ready for the next cycle. Specifically, the system can have a 2-way solenoid valve V-3 in the suction line with one port 780 open to the atmosphere. The bottom of the cylinder 770 is connected to a valve manifold 782 with two solenoid valves V-2, V-4. The solenoid valves can be Lee LF series designed for use in vacuum systems, 2-way valve LFVA 2450110H, viton seal, 24 volt and 3-way valve, LFRX 0500300B, viton seal, 24 volt. The 2-way valve V-4 can port the specimen liquid to the bubble flow cylinder 770, or to vacuum by-pass 784. The 2-way valve V-2 can control the filter dehydration vacuum source. FIG. 49 illustrates the valve logic.

The deposition control system can use an analog level indicator instead of the digital sensors 774. The analog level indicator senses capacitance of the aspirated liquid. The difference is only in the method of sensing the volume and fill rate of the liquid in the cylinder 770. Here two spaced electrodes are used, one around the outside of the cylinder 770 and the other positioned down the center of the cylinder the cylinder, separated from the aspirated liquid by a dielectric. A high frequency, such as 10 kHz, low voltage current is applied across the electrodes. Capacitance in this system is measured by a bridge circuit, which provides an analog indication of capacitance in the circuit. As fluid fills the column, capacitance in the circuit increases. A 10× differential in direct capacitance is easily obtained with this system. Capacitance is indicated on a real time basis and can be sampled frequently enough to provide control of the sampling system. This arrangement, like the first two, uses a computer or microprocessor and a bubble flow technology to measure the flow rate and the total fluid volume in real time. The predetermined volume increment for these arrangements can be in the range of about 0.1 ml to 5.0 ml, and preferably is in the range of about 1.0 to 2.0 ml.

A different system can use an ultrasonic indicator for measuring fluid movement through a tube. The ultrasonic system uses ultrasonic wave propagation through a moving liquid. In this regard, the third system employs an ultrasonic emitter and detector clamped across the liquid draw tube (suction line 750) operating on the distal end of the filter assembly F. This system provides a digital indication of fluid flow in the tube, the total volume aspirated through the tube being calculated by a flow interval calculation. It measures phase shift from the ultrasonic wave generator source to a detector for measuring flow speed.

Another way to measure aspirated fluid volume and control the duration of the specimen draw is to detect the change in the weight of the specimen vial. This can be accomplished by using a sensor that makes a high-precision measurement of the weight or mass of the vial containing the specimen that is being aspirated. Vial weight or mass is repeatedly measured at a high frequency such that the rate of change of the weight or mass of the vial is accurately determined. Specimen aspiration is completed when the rate of change in weight or mass has diminished by a predetermined amount or percentage from the initial rate. The weight sensor can be, e.g., a load cell in each conveyor receptacle 246, or a single load cell beneath the conveyor at the specimen acquisition head that rises to engage the container above it. In either case, the specimen acquisition head can be raised slightly during aspiration to unload the container so that the load cell can measure only the combined weight of the container and the remaining specimen.

Although specimen acquisition preferably is accomplished through aspiration (using a vacuum), it can also be accomplished by pressurizing the container 20 through an appropriate head that seals against the top of the container and forces specimen liquid up through tube 43 and through the filter assembly by means of positive pneumatic pressure. The fluid volume control schemes and mechanisms described above would also work in conjunction with such a pressurized specimen acquisition system.

The cell concentration can be selected from low to high by defining flow control cut-off. For a typical low cellularity result, the cut-off can be 80% of the 120% reference discussed above, and for high cellularity the cut-off can be set at 60% of the reference, selectable in 5% increments. The number of slides per specimen can range from one to three. Some of the typical default protocols are as follows:

GYN: 1,000 RPM stir, 30 second interval, 8-micrometer filter, 60%-high cellularity, one slide.

Urine: 1,000 RPM stir, 20 second interval, 5-micrometer filter, 70%-medium cellularity, one slide.

Lung sputum: 3,000 RPM stir, 120 second interval, 5-micrometer filter, 80%-high cellularity, two slides.

Re-Capping Station

After completing the specimen processing cycle, the specimen container is resealed with the stirrer still inside the container. It is preferred to use a thin, polypropylene-coated aluminum foil to form the new cap, which is available in roll form. The foil is drawn across the open end of the specimen container, thermally bonded to the container at a seal temperature of about 365° F. applied for about 3 seconds with a seal force of 3 pounds, and cut from the roll. Of course, any other type of re-capping material can be used as long as it is compatible with the vial material and creates a safe and reliable seal. For example, a foil backed with a thermosetting resin adhesive could be used; a sticky-backed foil could be used that does not require heat to effect a seal; or a plastic seal material can be bonded to the container ultrasonically. To enhance unattended operation, an automatic threader could be included for threading a new roll of sealing material into the re-capping mechanism. Cutting caps from a roll can be eliminated if roll-mounted pre-die-cut closures having peel-off tabs are fed to the re-capping mechanism.

Figure 50:
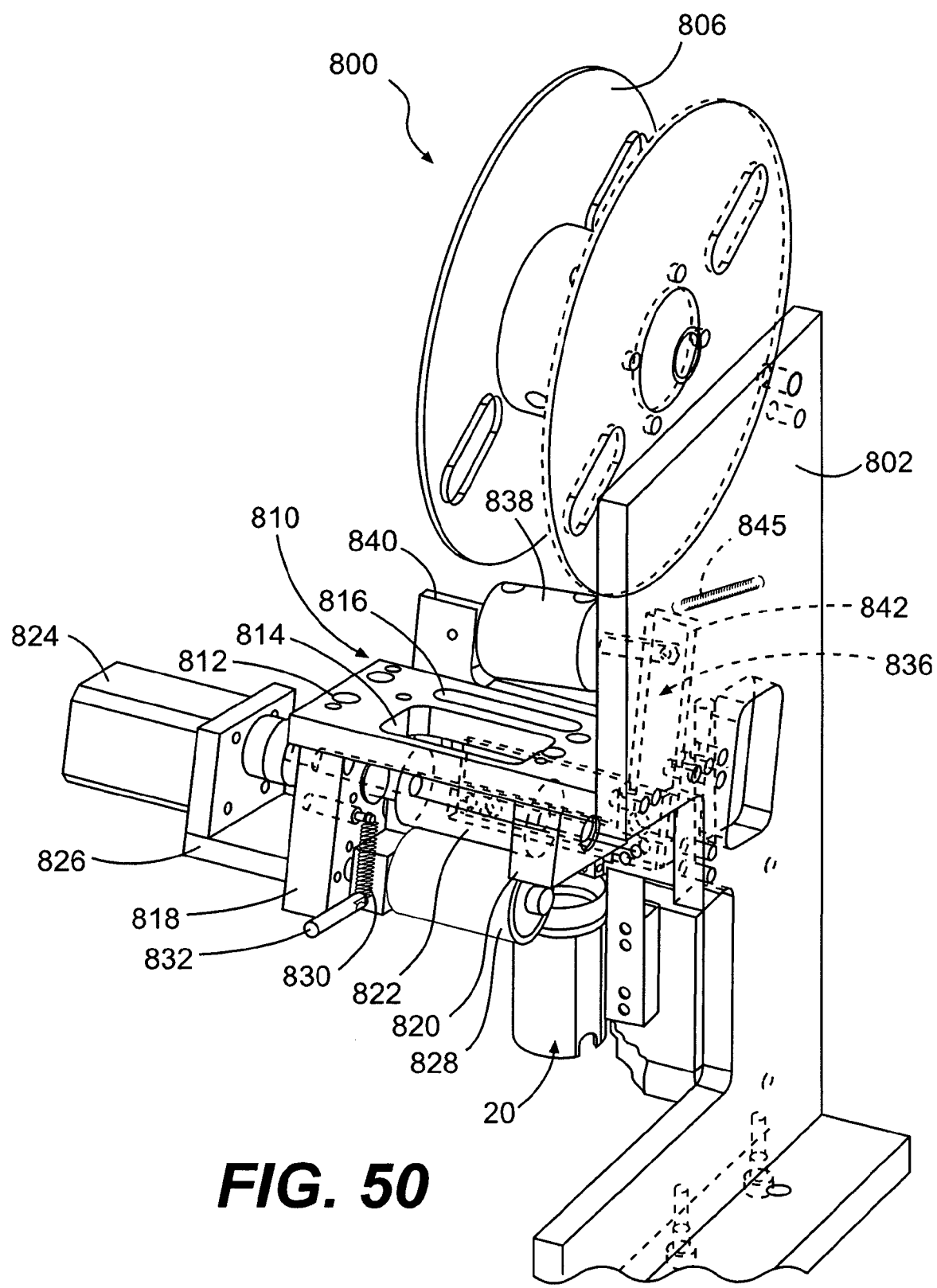
FIG. 50 is a front perspective view of the re-capping station of the LBP device.
Figure 52:
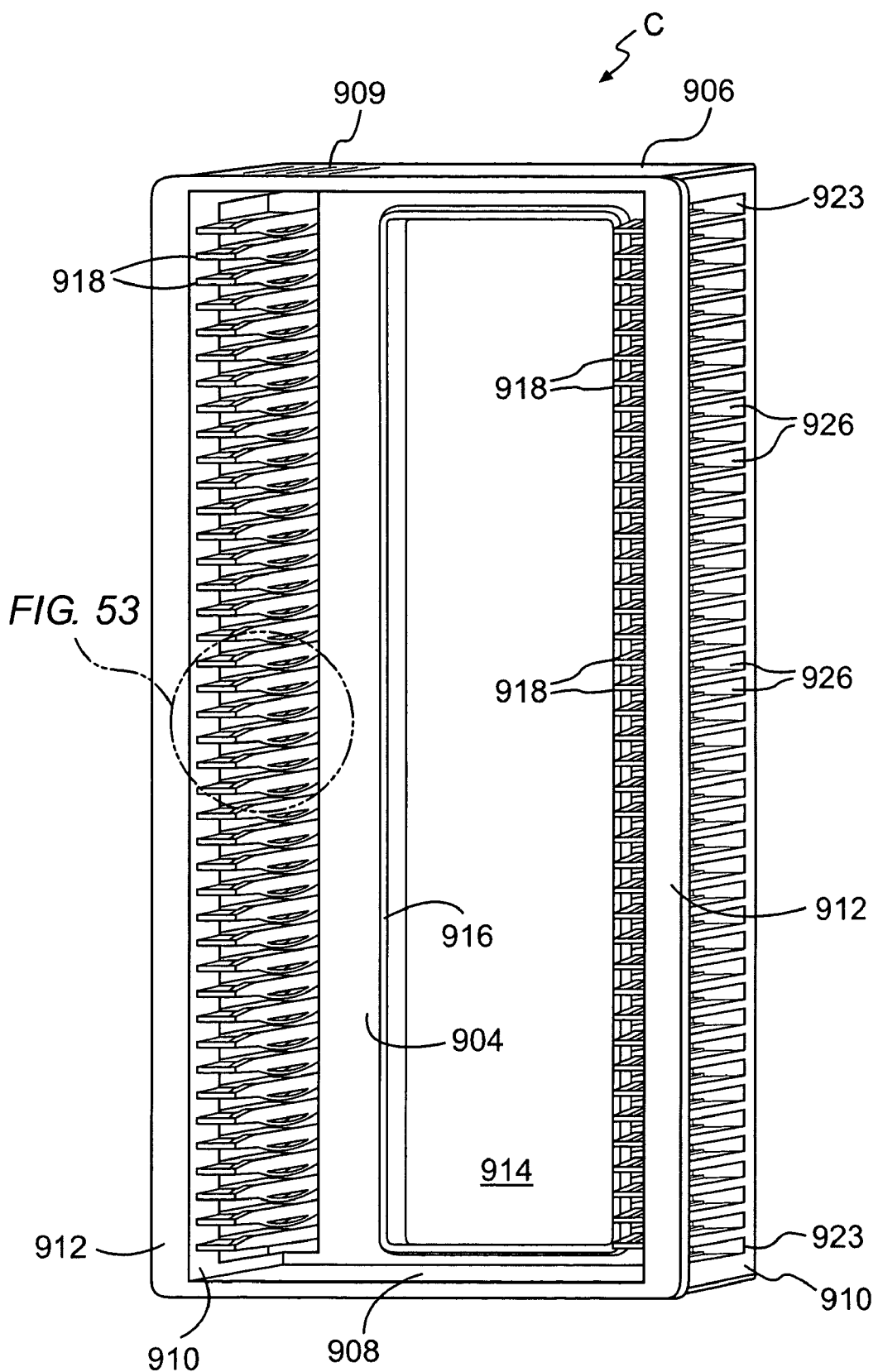
FIG. 52 is a front perspective view of a slide cassette used in the LBP device.
Figure 53:
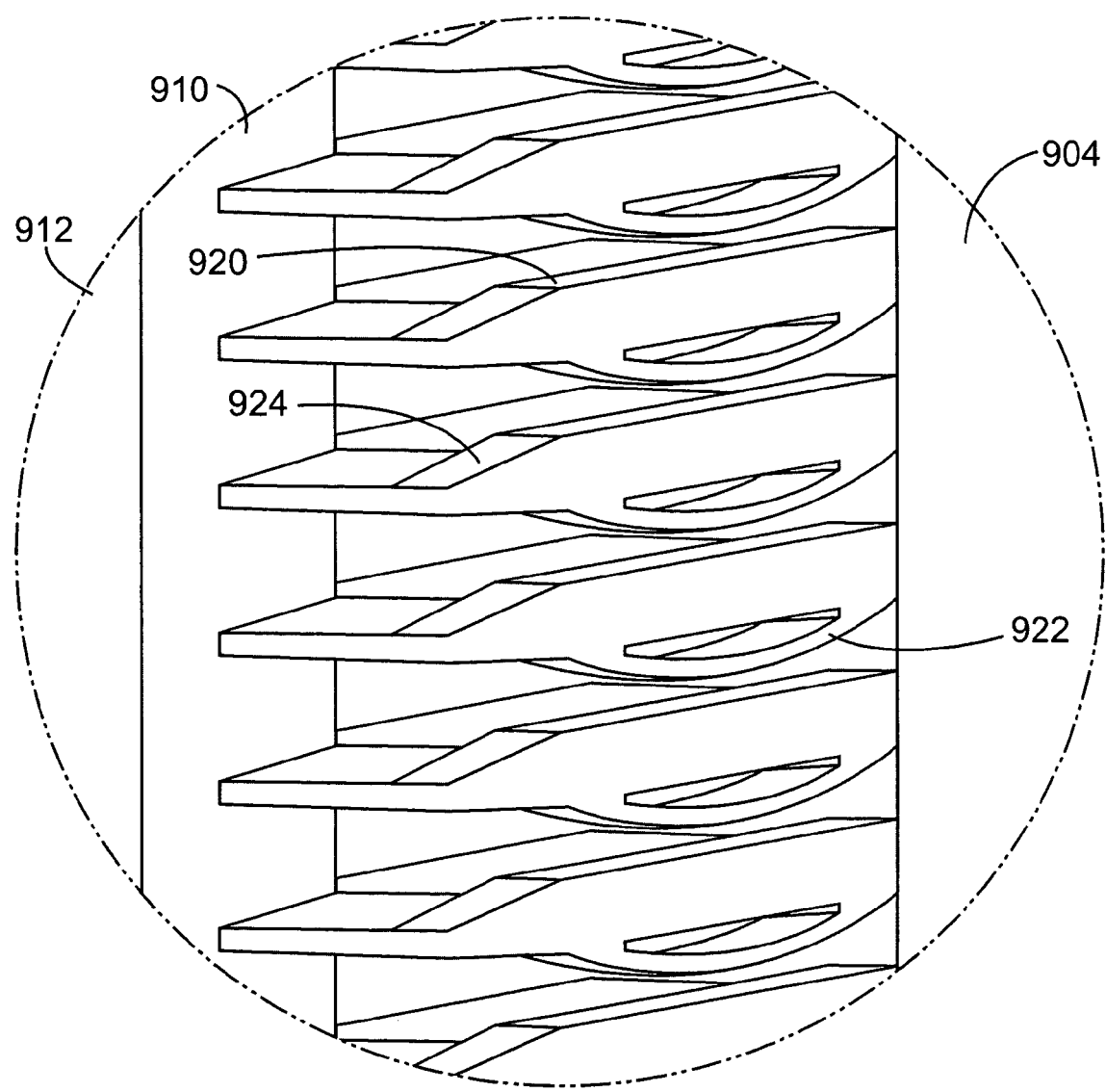
FIG. 53 is a detail perspective view of the slide cassette taken from FIG. 52.

Referring to FIGS. 50 and 52, the re-capping mechanism 800 has a side support plate 802 secured to the machine base plate. The side support plate carries a main frame 810 having a top plate 812 with slots 814, 816, and two side plates 818, 820. A driver capstan 822 is journaled in side plates 818, 820. A foil advance motor 824, mounted on a bracket 826, drives the capstan. A pressure roller 828 is pivotally mounted to the main frame 810 and resiliently engages the capstan under the influence of a spring 830. Capstan 822 and pressure roller 828 define between them a throat through which the foil runs, and have resilient surfaces which grip the foil for positive feed. A handle 832 allows the throat to be opened manually to allow the end of the foil to be fed into the throat after first passing through slot 814. A spindle 804, carried side support plate 802, supports a replaceable roll of foil.

Figure 51:
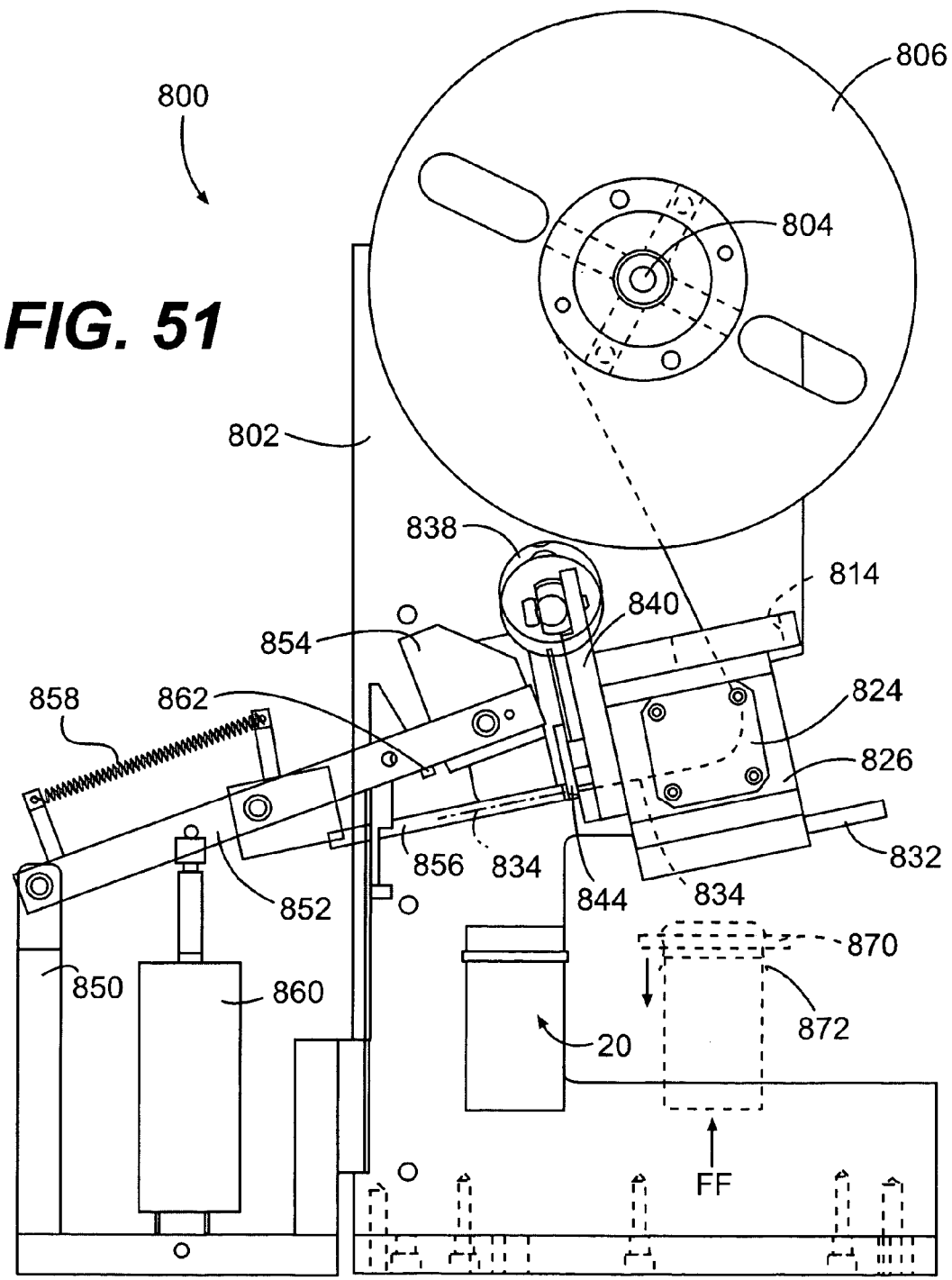
FIG. 51 is a side elevational view of the re-capping station.

FIG. 51 shows the foil path 834 through the throat. An L-shaped cutter 836 is pivoted at its elbow to the rear of main frame 810. One end of a single-acting pneumatic cutter actuator cylinder 838 is mounted on a bracket 840, and the other end of the cylinder is linked to the upper leg 842 of cutter 836. The lower leg of the cutter has a blade 844 that normally rests above the foil path downstream of the throat, held in that position by a spring 845 linked between the upper leg 842 and the support plate 802.

A rear post 850 pivotally supports an arm 852 that extends forwardly toward main frame 810. Arm 852 carries a heated platen 854 and a foil guide fork 856 having two tines that extend toward the throat and are spaced apart so as to allow the platen 854 to pass between them. Arm 852 is kept elevated, in the rest position shown in FIG. 51, by a spring 858. During the re-capping operation a single-acting pneumatic cylinder 860 pulls down on the arm 852 to lower the platen 854 and the guide fork 856. Note the position of a container 20 in a transport receptacle (not shown) beneath the platen 854.

In operation, the foil advance motor turns the capstan 822 to feed a measured length of foil past the cutter blade 844, into the fork 856, and to the position shown by the dashed line in FIG. 51. A photocell 862 detects the leading edge of the foil and signals the motor to stop. Then cylinder 838 is actuated to cut the foil, and cylinder 860 is actuated to pull arm 852 down to the seal position. The cut length of foil is sandwiched between the platen 854 and the container 20, and the container is sealed. After about three seconds cylinder 860 is deactivated and the arm 852 rises, returning to its rest position. A vacuum assist (not shown) optionally may be used to help hold the cut length of foil in position on the platen prior to sealing.

The foil caps applied by the re-capping mechanism are approximately square in shape. The corners of the foil caps can protrude from the vials and interfere with other re-capped vials that are returned to the trays 330. Accordingly, a foil folding ring 870 (seen in phantom lines in FIG. 51) preferably is provided which acts to fold the edges and corners of each foil cap down along the side of the container. The foil folding ring 870 preferably is mounted to act on the vial in the transport position immediately downstream of the re-capping mechanism, i.e., position "FF" in FIG. 51, and may be mounted on the re-capping mechanism itself, e.g., to main frame 810, so that actuation of cylinder 860 serves simultaneously to apply a foil cap to one container and fold the edges and corners of the foil cap of the preceding (downstream) container. Alternatively, the foil folding ring or an equivalent foil folding mechanism can be mounted further downstream of the re-capping mechanism so as to act independently thereof.

Foil folding ring 870 is a metal ring having an inner diameter that is slightly larger than the outside diameter of the threaded portion of the container 20. The ring 870 is mounted on an arm (not shown) that moves downwardly when actuated to lower the ring 870 over the upper end of the container. As the ring encircles the container, it folds the overhanging portions 872 of the foil cap against the side of the container. When the ring rises after folding the foil, the container is held in position in its transport receptacle by a pin (not shown) that is mounted on a leaf spring (not shown) and is situated in the center of the ring 870. The leaf spring is carried by the arm that holds the ring, so the pin resiliently presses down against the center of the foil cap until the arm and the ring retract fully.

The foil seals applied to the processed containers are easily punctured by a syringe or a pipette to obtain further liquid specimen samples. The seals are very durable, however, withstanding rough handling and preventing leakage in low ambient pressure conditions, e.g., in aircraft flying as high as 40,000 ft. Further, the appearance of the foil seal makes it readily distinguishable from the cover of an unprocessed vial, making handling by low-skilled operators virtually foolproof. To avoid the potential of puncturing the foil seal inadvertently, the re-sealed container can be capped with an unused screw-on cover of a distinct color.

Slide Handling And Presentation

The LBP device can use 30 and 40 slide plastic magazines (cassettes), which can accept standard 25 mm×75 mm×1 mm and 1×3×0.040 in. slides. Metric and inch based slides can be used interchangeably. FIGS. 52-55 show a 40-slide cassette C suitable for use in the LBP device. The slide cassette is in some respects similar to that disclosed in U.S. Pat. No. 5,690,892 (incorporated herein by reference), but is specially adapted for use in other devices as well, such as an automated stainer, an automated image analyzer, and a pathology work station, so that the slides do not have to be unloaded and reloaded into different magazines for use in those devices. Machine-readable indicia on the cassette, such as a bar code or an embedded microchip, provides cassette information that can be linked by the DMS to the bar codes on the slides in the cassette so that the location and status of any cassette and any slide in that cassette can be tracked in a laboratory system. The cassettes are stackable for compact storage and easy retrieval.

Specifically, the slide cassette is molded of plastic and has a generally rectangular shape with an open front 902, a rear wall 904, a top wall 906, a bottom wall 908 and side walls 910. The top wall 906 bears bar-coded information 909. A guide flange 912 extends laterally outwardly from each side wall. Rear wall 904 has a rectangular central opening 914 through which a slide shuttle can pass (see below) to extract and return one slide at a time. An inwardly projecting ridge 916 around the central opening acts as a stop against which the slides abut when they are inserted into the cassette. The preferred material for the cassette is ABS plastic; alternative choices include polyurethane, thermoplastic polyester, and polypropylene. The open front face is sized to accommodate the rear of another like cassette so as to be stackable.

The slides are supported on shelves 918 at each side of the cassette. In the illustrated embodiment there are 41 pairs of left and right shelves, and each pair (except for the top pair) supports one slide that spans the space between the shelves. Referring to the detailed view in FIG. 53, each shelf (except for the top and bottom shelves) has a raised top ledge 920 on which the slide rests and an underside beam spring 922 for applying a force to pinch and thereby frictionally restrain the slide against the top ledge directly beneath it. This arrangement keeps the slides from falling out of the cassette, even when the cassette is held face down, yet enables each slide to be moved out of and back into the cassette by the slide presentation apparatus, described below, without blocking, scratching or interfering with the slide-mounted specimens. Each shelf 918 also has a lead-in ramp 924 which guides the slide during insertion into the cassette. Each shelf 918 (including spring 922) preferably is integrally molded into the cassette and is attached to both the rear wall 904 and a side wall 910. However, separately fabricated springs, plastic or metal, may be inserted between the shelves instead.

Each side wall is provided with multiple drainage ports 926 which allow fluid to drain from the cassette after removal from a staining bath. The last (top and bottom) drainage ports 923 on each side also cooperate with a hanger assembly of a stainer for moving the cassette from one staining bath to another. During the staining operation the cassette is oriented generally on its side, hung from the last two drainage ports on the upper side. An all-plastic construction makes the cassette compatible with acid baths and all types of staining bath compositions.

Figure 54:
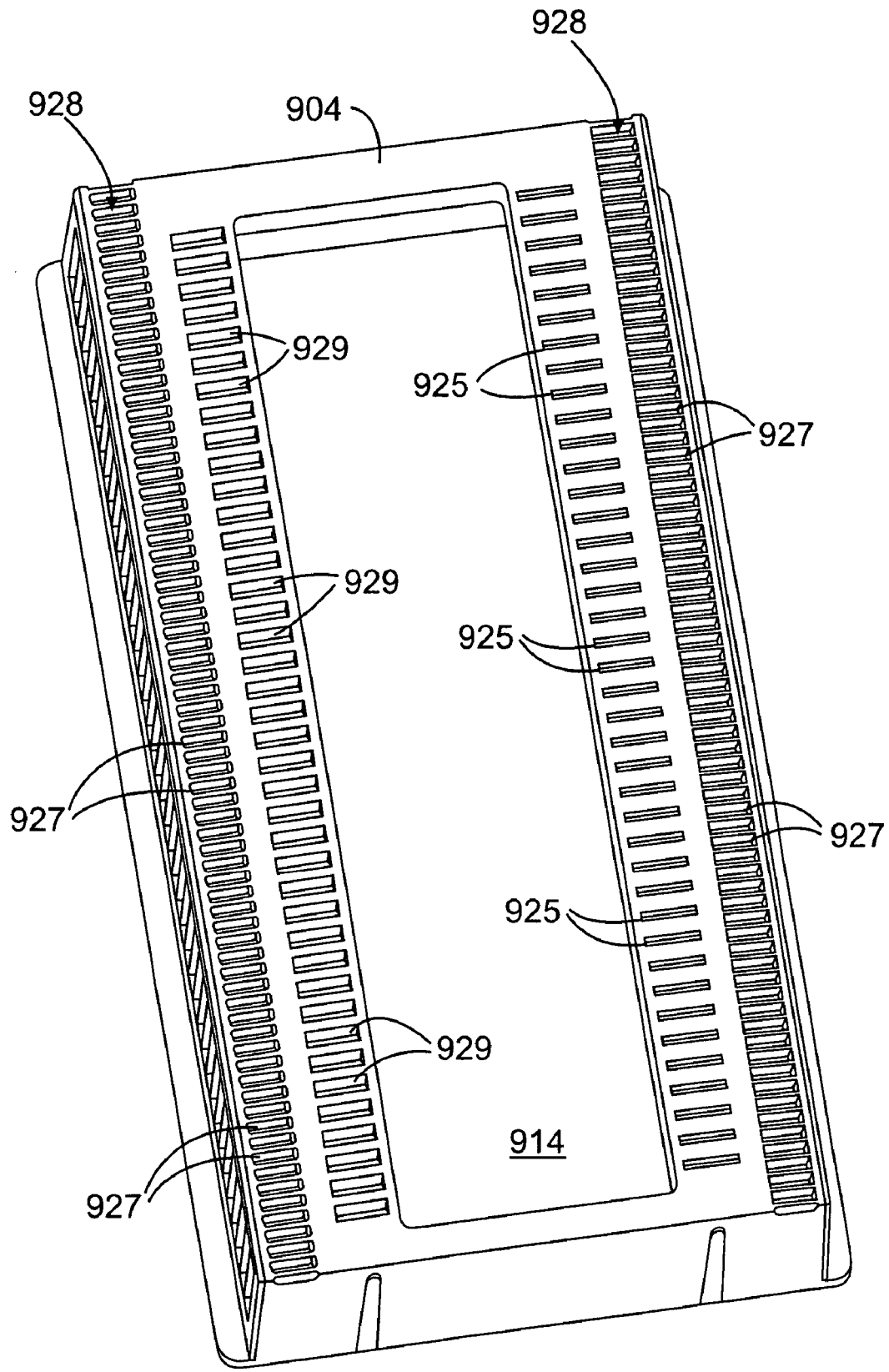
FIG. 54 is a rear perspective view of the slide cassette.
Figure 55:
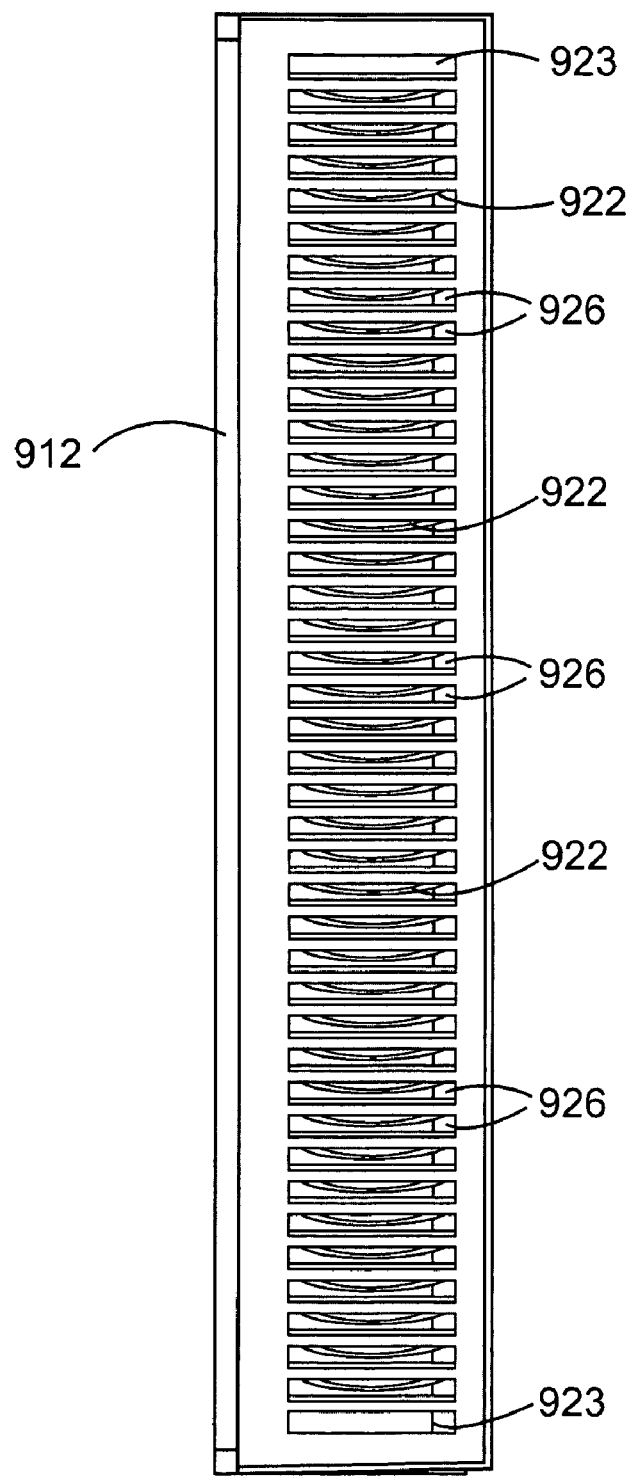
FIG. 55 is a side elevational view of the slide cassette.

Referring to FIG. 54, rear wall 904 has two rows of apertures 927 that form two integrally molded gear racks 928, which are adapted to engage pinion gears 936 (see below) for moving the cassette longitudinally so that each slide can be accessed by the slide shuttle. Two spaced parallel racks and two pinion gears enhance the smoothness and accurate positioning of the cassette, as compared to a single rack and single pinion. Also integral with the rear wall is a row of 40 cassette position sensing slots 929 extending through the rear wall and coincident with the positions of the slides to allow for optical sensing of each slide. Further, rear wall 904 has a row of 40 blind recesses 925 (these do not extend completely through the rear wall) that allow for accurate sensing of cassette position when it is driven via the gear racks 928.

The molded cassette preferably is supplied wrapped in sealed plastic for cleanliness, with slides installed. It is therefore well suited for shipping, relatively low in cost, disposable yet reusable. It has a high storage capacity and is stackable with others, thus providing high density storage for specimen samples.

Slide cassettes populated with slides are manually loaded into the LBP device in an elevated in-feed track 930 (see FIG. 11) located behind the filter loading station 600 and the specimen acquisition station 700. No latching is required to enter cassettes into the system. Up to ten unprocessed cassettes can be loaded in the LBP device at any one time, but only in a single orientation. The cassettes can be marked with a top indicator, and will not be accepted if they are installed backwards or upside down. The cassettes are loaded with their open fronts facing to the right as seen in FIG. 11, with the lead cassette between vertical rails 932.

The lead cassette moves down incrementally whenever a new slide is to be withdrawn from the cassette for specimen printing. This is accomplished by a stepper motor (not shown) driving pinion gears 936 that engages the racks 928 on the back of the cassette C (see FIG. 54). When all slides in the cassette have been processed, the cassette descends all the way to outfeed track 940, and a stepper motor/lead screw pusher 938 moves the cassette to the right into outfeed track 940, and then retracts. Then the next cassette in the infeed track 930 is advanced by a motor/lead screw pusher (not shown) to the front position between vertical rails 932, where it is engaged by the pinion gears 936 and moved downwardly until the first (lowest) slide comes into position for extraction. Each of the feed tracks can have a home sensor, which can be Omron self-contained shutter type, and a cassette full sensor, which can be Keyence fiber optic.

Figure 56:
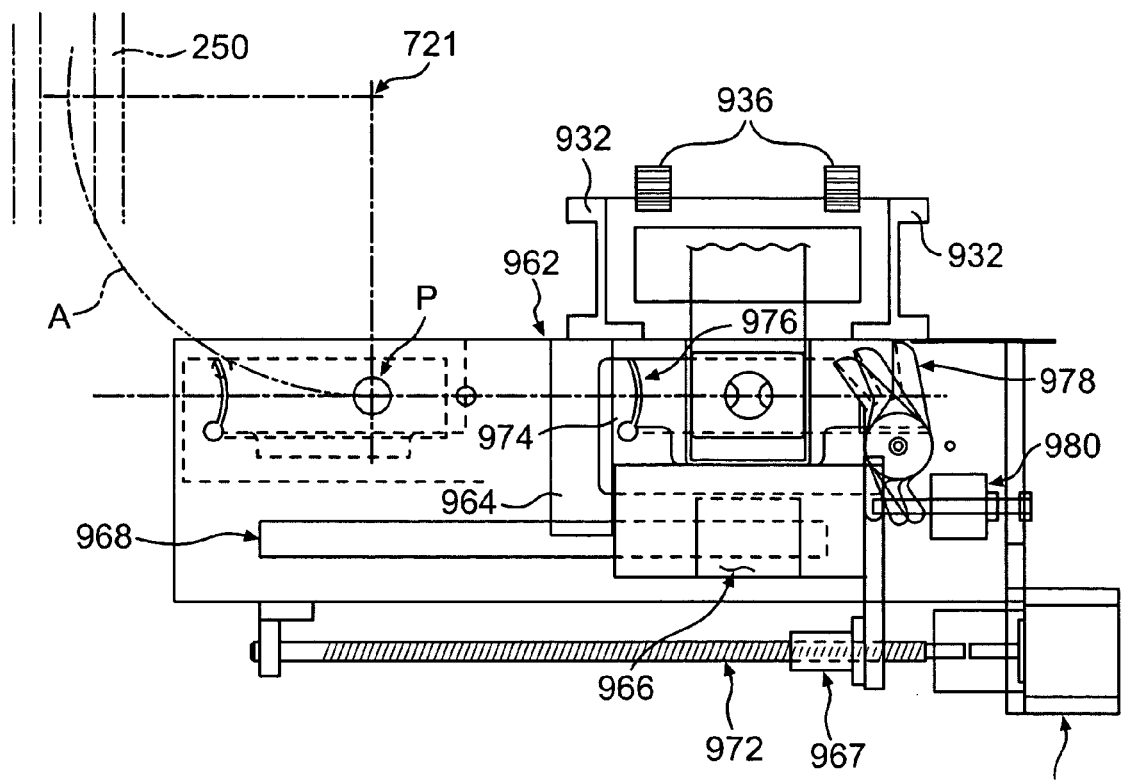
FIG. 56 is a top plan view of the slide presentation system of the LBP device.
Figure 57:
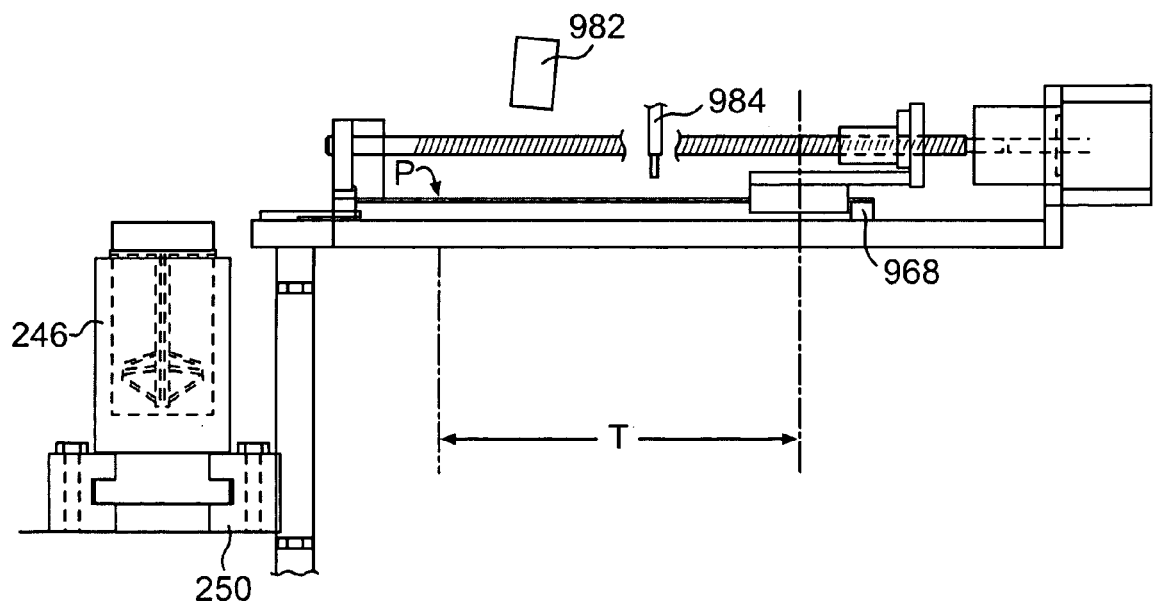
FIG. 57 is a side elevational view of the slide presentation system.

FIGS. 11, 56 and 57 show the slide presentation system, which uses a slide shuttle feed system 960, e.g. AM Part No. 5000-1, for extracting one slide at a time from the cassette along the X-axis and placing it on a Y-axis handler, which moves the slide to the pressing (print) position. The aforementioned U.S. Pat. No. 5,690,892 discloses a similar slide cassette and shuttle arrangement used in a pathology work station (microscope). The Y-axis handler 962 has a slide platen 964 secured to a follower 966, 967. The handler is driven by a stepper motor 970 and a lead screw 972, guided along a rail 968. A slide is held to the platen under a fixed shoulder 974 (against a spring 976) and a pivoted arm 978 which is spring-biased in the counterclockwise direction as seen in FIG. 56.

When the handler 962 moves to the left, arm 978 moves off an adjustable stop 980 and rotates over the slide. The full Y-axis slide travel (shown as "T" in FIG. 57) brings the center of the slide to the print position "P" (note the dashed line position of the slide and the handler in FIG. 56). On its way to the print position the bar code number on the slide is acquired by a bar code reader 982 and transmitted to the host data base. When the print position is reached the suction head 702, which has pivoted along arc "A" about axis 721, lowers the filter assembly F into contact with the slide, as described above, depositing (printing) the specimen on the slide. Vacuum on the filter is maintained throughout the printing cycle to prevent over-hydration of the sample and unintentional dripping.

After printing the slide moves back to the right, pausing under a fixative dispensing head 984. Here a solenoid-driven pump (not shown), such as Lee LPL X 050AA, 24V, 20 microliter per pulse, yielding 12 microliters per pulse (maximum of 2 pulse/second), applies fixative to the specimen. The total volume can be determined by the number of solenoid cycles. The total fixative volume dispensed is programmable in 20 microliter increments. It can have a flexible connection to a dispensing sapphire jet nozzle with a 0.030 in. orifice. The liquid can be gravity-fed from a reservoir to the pump. The reservoir can be a tank and can have a "fluid low" sensor connected to the operating system. More than one fixative dispenser can be employed to provide alternative fixatives as determined by processing protocols.

After the specimen is fixed, the completed slide moves all the way to the right, where it is transferred by the slide shuttle mechanism back to its original position in the cassette. When the cassette is fully processed, the entire cassette is ejected into the outfeed track 940, as described above.

A Complete Laboratory System

The present LBP device does not require that specimens be pre-processed before loading, and can automate every step of the slide preparation process. Moreover, the device does not require the operator to open any of the specimen containers—an important operator safety feature. The LBP device can automatically prepare high quality cytology slides from all specimen types, including mucous-containing GYN and non-GYN specimens, using the integral high-speed, high-shear mixing station that facilitates mucous disaggregation. The incorporated dual-flow filter system allows production of slides with optimal cell separation, cell concentration, cell dispersion, and optimal preservation of antigens, DNA, and morphologic characteristics to enhance the performance of subsequent testing. The slide cassettes, containing up to 40 slides each, will be utilized in the follow-on laboratory processing devices to avoid the labor-intensive need to transfer slides to different racks before continuing with slide processing. Data on the patient, the specimen, the vial, the cassette and the slide can be transferred automatically to the LIS over the user's network, via a DMS software interface.

The present LBP device can provide eight hours of unattended operation. Thus, if the operator re-loads the device before leaving for the day, a single-shift laboratory can produce two shifts of output per day without added personnel or equipment costs. The total throughput can exceed 160,000 slides per year, at a per-test cost significantly below that of the current leading LBP system.

The LBP device also has the capability to process specimens for current and future molecular diagnostic tests including quantitative DNA analyses, and tests utilizing markers & probes. Features built into the device include the capacity to employ multiple fixative dispensers in order to provide non-routine fixatives that may be required for special molecular diagnostic tests.

The complete laboratory system, illustrated, e.g., in FIG. 21*a*, includes a pathology review station, a computer-aided microscopy work station used by pathologists to review specimen slides and sign out cytology cases. As with all components of the laboratory system, the pathology review stations are networked to the DMS and thereby to all other devices on the system, for rapid access to patient data and specimen processing information. The pathology review station accepts slide cassettes for automated loading and review of specimen slides. Computerized, fully automated image analyzers will perform quantitative analyses of DNA and molecular diagnostic tests, receiving their operating instructions and reporting their results via specimen bar codes using the integral DMS. See, for example, AccuMed/MDI U.S. Pat. Nos. 5,963,368; 6,091,842; and 6,148,096, which are incorporated herein by reference.

The laboratory system will also include, for example, slide autostainers and autocoverslippers (and/or combination automated stainer/coverslipper devices) controlled via the DMS that utilize the same slide cassette as the present LBP device. Cassettes containing processed slides can be utilized directly in these additional devices without the need to unload slides and reload them into separate racks.

The inter-connectivity and high degree of automation of the processing and analytical devices making up the laboratory system will enable high-quality, high-throughput specimen processing and analysis at relatively low cost.

INDUSTRIAL APPLICABILITY

The above disclosure presents a safe, effective, accurate, precise, reproducible, inexpensive, efficient, fast and convenient vial-based system and method for collecting, handling and processing liquid-based cellular specimens, providing fully integrated specimen and information management in a complete diagnostic cytology laboratory system.

The invention claimed is:

1. An apparatus for engaging and moving a mixer disposed in an uncovered, upstanding specimen container, the top of the mixer having a cavity defined by an upstanding annular wall, the apparatus comprising:
   a holder mounted above the uncovered, upstanding specimen container for vertical movement relative to the specimen container and adapted to releasably engage the upstanding annular wall of the mixer, which is disposed loosely in the specimen container when not engaged by the holder;
   a clamping actuator adapted to selectively cause the holder to engage or release the annular wall of the mixer, which is disposed in and remains in the specimen container;
   a vertical actuator adapted to move the holder along a vertical axis toward and away from the mixer disposed in the upstanding specimen container, and to elevate the mixer relative to the specimen container when the mixer is engaged by the holder;
   a mixing actuator adapted to effect movement of the holder to cause the engaged mixer to mix the specimen in the upstanding specimen container.

2. An apparatus according to claim 1, wherein the holder comprises a collet having flexible fingers, and the clamping actuator selectively moves the fingers radially to expand or contract the collet into or out of engagement with the annular wall of the mixer.

3. An apparatus according to claim 2, wherein the collet fingers fit within the cavity of the mixer and are expandable to engage the inner surface of the annular wall.

4. An apparatus according to claim 3, wherein the holder is rotatable about the vertical axis to mix the specimen.

5. An apparatus according to claim 1, wherein the holder comprises radially movable members adapted to grip the upstanding annular wall of the mixer.

6. An apparatus according to claim 5, wherein the holder is rotatable about the vertical axis to mix the specimen.

7. An apparatus according to claim 1, wherein the mixing actuator is adapted to effect movement of the holder to cause the engaged mixer to mix the specimen only when the mixer is elevated by the holder relative to the upstanding specimen container.

8. An apparatus according to claim 7, wherein the holder is rotatable about the vertical axis to mix the specimen.

* * * * *